United States Patent
Wang et al.

(10) Patent No.: US 11,890,599 B2
(45) Date of Patent: Feb. 6, 2024

(54) CATALYST FOR OXIDATIVE OLEFIN GENERATION FROM PARAFFINS

(71) Applicant: ExxonMobil Technology and Engineering Company, Annandale, NJ (US)

(72) Inventors: Kun Wang, Branchburg, NJ (US); Yi Du, Coopersburg, PA (US); Bradley D. Wooler, Allentown, PA (US); Jonathan E. Mitchell, Easton, PA (US); Christine E. Kliewer, Clinton, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 150 days.

(21) Appl. No.: 17/451,185

(22) Filed: Oct. 18, 2021

(65) Prior Publication Data
US 2023/0119666 A1 Apr. 20, 2023

(51) Int. Cl.
| | | |
|---|---|---|
| *B01J 27/25* | (2006.01) | |
| *B01J 37/04* | (2006.01) | |
| *B01J 37/03* | (2006.01) | |
| *C07C 5/48* | (2006.01) | |

(52) U.S. Cl.
CPC .......... *B01J 27/25* (2013.01); *B01J 37/031* (2013.01); *B01J 37/04* (2013.01); *C07C 5/48* (2013.01)

(58) Field of Classification Search
CPC ........... B01J 27/25; B01J 37/031; B01J 37/04
USPC .................. 502/300, 344–346, 318, 319
See application file for complete search history.

(56) References Cited

U.S. PATENT DOCUMENTS 5,879,645 A * 3/1999 Park .................. B01D 53/9418
423/239.1

FOREIGN PATENT DOCUMENTS

| KR | 1011830 B1 * | 1/2011 | ......... B01D 53/9418 |
| KR | 20110032929 * | 3/2011 | .............. B01J 23/72 |
| WO | WO-2017182893 A1 * | 10/2017 | .............. B01J 23/80 |

OTHER PUBLICATIONS

Nauert, et al., "Role of support Lewis acid strength in copper-oxide-catalyzed oxidative dehydrogenation of cyclohexane", ACS Catalysis, 2018, 8, 7598-7607.
Gayan et al., "Effect of gas composition in chemical-looping combustion with copper-based oxygen carriers: fate of light hydrocarbons", International Journal of Green House Gas Control, 2010, 4, 13-22.
Yan et al., "Synthesis of Cu0.5Mg1.5Mn0.5Al0.5Ox mixed oxide from layered double hydroxide precursor as highly efficient catalyst for low-temperature selective catalytic reduction of NOx with NH3", Journal of Colloid and Interface Science, 2018, 526, 63-74.
Wang, et al., "Large-scale synthesis of highly dispersed layered double hydroxide powders containing delaminated single layer nanosheets", Chem. Comm., 2013, 49, 6301-6303.

* cited by examiner

*Primary Examiner* — Patricia L. Hailey
(74) *Attorney, Agent, or Firm* — Shook, Hardy & Bacon L.L.P.

(57) ABSTRACT

The present disclosure provides an active material comprising a mixed metal oxide in a hydrotalcite derived rocksalt structure, a processes to convert paraffins to corresponding olefins and or heavier hydrocarbons using the active material, and a method of preparing the active material.

28 Claims, 20 Drawing Sheets

CATALYST FOR OXIDATIVE OLEFIN GENERATION FROM PARAFFINS

FIELD

The present disclosure provides catalyst compositions for the conversion of light paraffins to olefins and distillates. The present disclosure provides methods of making said catalyst compositions. The present disclosure further provides processes to convert light paraffins to olefins and distillates.

BACKGROUND

As the production of shale and tight oils is increasing in the United States of America, light paraffins (e.g., $C_3$ to $C_9$), such as Liquefied Petroleum Gas ("LPG"), Natural Gas Liquids ("NGL"), are becoming increasingly abundant and at lower costs. Ethane to light naphtha range paraffins are largely fed to steam crackers or dehydrogenated to make olefins. For example, ethane is steam-cracked to make ethylene, and light naphtha (b.p. 15.5° C.-71° C.) is steam cracked to make ethylene, propylene, and small volumes of dienes.

Short-chain alkanes (e.g., $C_2$-alkanes to $C_5$-alkanes) can also be converted to their corresponding olefin using dehydrogenation technologies. Dehydrogenation of short-chain alkanes (e.g., $C_2$ to $C_5$) commonly uses one of two types of catalysts: platinum-based catalyst(s) or chromium oxide catalyst(s). The dehydrogenation process is typically carried out at temperatures>450° C., and under ambient or sub-ambient pressure, mainly due to the fact that paraffin dehydrogenation to olefins, or dehydrogenative coupling to heavier paraffins, are both thermodynamically unfavored and conversion is equilibrium limited. Hence, the free energy of the dehydrogenation reaction only becomes favorable at temperatures of at least 600° C. To manage the frequency of a catalyst regeneration process due to coking, reactors such as moving-bed, cyclic swing-bed, or fluidized bed reactors are employed. On the other hand, heavy naphtha (b.p. 71° C.-182° C.) is typically fed to catalytic reformers in order to produce aromatics and hydrogen, but no catalyst/process that selectively dehydrogenates naphthenes to mono-olefins has been described.

Conversion of light paraffins to distillate is typically performed using the following technologies: 1) steam cracking or catalytic dehydrogenation of paraffins to generate olefins, followed by olefin oligomerization; 2) converting the feed to syngas via partial oxidation, followed by Fischer-Tropsch or methanol to hydrocarbons synthesis. However, these approaches involve high temperatures (e.g. >400° C.) and are energy intensive.

As the reformers reach capacity, coupled with the limited growth in demand for aromatics, there is a continuous need to convert heavy naphtha, particularly heavy virgin naphtha (HVN), to large volume, higher value products. Furthermore, global transportation fuels outlook suggests that the long-term demand for automotive gas (e.g., gasoline) will decrease, while the demand for octane is expected to grow with the increasing use of high-compression engines. Conversely, global fast growing demands for distillate (e.g., jet, diesel) favors the conversion of heavy naphtha (low-octane gasoline; e.g., Research Octane Number ("RON") and Motor Octane Number ("MON") for cyclohexane are 83.0 and 77.2, respectively; RON and MON for n-heptane are zero) to distillate range liquids.

Furthermore, the excess in supply of light alkanes and olefins due to shale gas and hydraulic fracturing (also referred to as "fracking"), in addition to traditional light cuts (e.g., $C_5$ of the Fluid Catalytic Cracking, "FCC"), has limited new uses. Hence, growing the molecular weight of light alkanes and olefins into fuel/lubricant ranges would be valuable, particularly due to the lower value of light alkanes, and the higher value of fuels, and lubricant range hydrocarbons.

Metal oxide materials have found use as oxygen carriers for catalytic upgrading of chemical species via cyclic catalytic conversion, or chemical looping combustion of natural gas and methane, especially for the production of syngas. Accordingly, metal oxides and mixed metal oxides have wide applications, such as catalyst, adsorbents, superconductors, semiconductors, ceramics, antifungal agents. Despite the energy saving role of such process, high temperatures are still required (e.g. about 700° C. to about 900° C.), and often need additional solvent in the feed. These processes often require the use of metal oxides, such as $CrO_x$ and $Ga_2O_3$, as catalysts for paraffin dehydrogenation where $H_2$ is present (either as co-feed or product) in those systems which produces a high content of hydrogen in the dehydrogenated products. Conversion for dehydrogenation process is limited by the thermodynamic equilibrium and requires significant amount of energy input to get acceptable conversions. Paraffin oxidative dehydrogenation, on the other hand, is not constrained by thermodynamic conversions thus has the advantage of significant energy savings. However, an inherent challenge in paraffin oxidative dehydrogenation is that the product olefin is more reactive than feed (except for ethane to ethylene conversion), limiting per pass olefin yield. Consequently, it is highly desirable to have catalytic materials that can improve olefin yield in an oxidative dehydrogenation environment.

Therefore, there remains a need for processes that provide a highly efficient and economical conversion of light hydrocarbons to light distillates and or mid-distillates, and or as distillate range liquids, under mild conditions. Furthermore, there is a need for processes to convert heavy naphtha, particularly naphthene-rich heavy virgin naphtha, to distillate range products.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

This invention provides for a new catalyst with improved mechanical and chemical stability that is useful in a process to convert paraffin to olefin.

In one aspect, the invention provides an active material, comprising:

a mixed metal oxide of the formula:

$$A_a(M1)_x(M2)_{y-x}(M3)_zO_{y+3/2z} \quad (I)$$

wherein:
A is an alkali metal;
M1 is a divalent metal;
M2 is a divalent metal;
M3 is a trivalent metal;
a is 0.01≤a≤4;
x is 0.01≤x≤4;
y is an integer from 2≤y≤4;
z is 0.25y≤z≤0.5y; and
the ratio a/x is from 0.1 to 1.0;
and an optional support material.

In some embodiments of the active material of the invention, A is selected from the group consisting of Na, Li, K, Rb, and Cs. In particular embodiments, A is Na.

In other embodiments of the active material of the invention, M1 is selected from the group consisting of Mn, Fe, Co, Ni, and Cu. In particular embodiments, M1 is Fe, Co, Ni, or Cu. In other particular embodiments, M1 is Cu.

In still other embodiments of the active material of the invention, M2 is selected from the group consisting of Mg, Ca, Sr, Ba, Zn, Co, Cu, Ni, and Fe. In particular embodiments, M2 is Mg, Co, or Ni. In other particular embodiments, M2 is Mg.

In yet other embodiments of the active material of the invention, M3 is selected from the group consisting of Ga, Fe, Co, Mn, Cr, and Al. In particular embodiments, M3 is Al.

In other embodiments of the active material of the invention, z is chosen to satisfy charge neutralization.

In some embodiments of the active material of the invention, the active material has a structure having X-Ray diffraction peaks at d-spacing corresponding to three characteristic features of an M2O rocksalt phase, d1, d2 and d3, wherein the three characteristic d-spacing are:

$$2.41 \text{ Å} < d1 < 2.49 \text{ Å},$$

$$2.09 \text{ Å} < d2 < 2.15 \text{ Å},$$

$$1.48 \text{ Å} < d3 < 1.52 \text{ Å};$$

And wherein the structure is substantially free of X-Ray diffraction peaks at d-spacing corresponding to an M1O phase.

In other embodiments of the active material of the invention, the active material according has the formula:

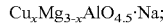
$$Cu_xMg_{3-x}AlO_{4.5}\cdot Na;$$

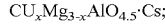
$$Cu_xMg_{3-x}AlO_{4.5}\cdot Cs;$$

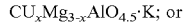
$$Cu_xMg_{3-x}AlO_{4.5}\cdot K; \text{ or}$$

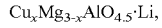
$$Cu_xMg_{3-x}AlO_{4.5}\cdot Li,$$

wherein x is $0.01 \leq x \leq 3$.

In certain embodiments of the active material of the invention, the support material is a non-acidic oxide, a non-acidic clay, a basic oxide, a zeolite, an organo clay, or a combination thereof. In particular embodiments, the support material is selected from zeolites, organoclays, $Al_2O_3$, $ZrO_2$, $SiO_2$, $SiO_2/Al_2O_3$, $SiO_2/TiO_2$, silica clay, silicon oxide/clay, or mixtures thereof.

In another aspect, the invention provides a process for upgrading a hydrocarbon feed, comprising:
introducing at a temperature of from about 50° C. to about 500° C. a hydrocarbon feed comprising paraffins and introducing an oxidizing agent to an active material according to the invention;
obtaining a product mixture comprising one or more $C_3$-$C_{50}$ cyclic olefin, one or more $C_2$-$C_{50}$ acyclic olefin, one or more $C_5$-$C_{200}$ hydrocarbon, or a mixture thereof, wherein the product mixture comprises less than 1000 ppm $H_2$.

In some embodiments of the process of the invention the oxidizing agents is air. In still other embodiments of the process of the invention introducing the oxidizing agent is performed: at a temperature of from about 50° C. to about 1,000° C.; at a pressure of from about 15 psig to about 500 psig; and at a residence time of about 1 milli-second to about 48 hours.

In other embodiments of the process of the invention, the product mixture comprises less than 10 ppm $H_2$.

In certain embodiments of the process of the invention, the hydrocarbon feed is a naphtha feed comprising one or more $C_2$-$C_{50}$ cyclic alkanes, one or more $C_2$-$C_{50}$ acyclic alkanes, or a mixture thereof. In particular embodiments, the feed comprises one or more $C_2$-$C_{50}$ cyclic alkanes selected from cyclopropane, cyclobutane, cyclopentane, cyclohexane, cycloheptane, cyclooctane, or mixtures thereof. In still other embodiments, the hydrocarbon feed consists of cyclohexane. In particular embodiments, the feed comprises a $C_2$-$C_{50}$ acyclic alkane selected from propane, n-butane, iso-butane, n-pentane, iso-pentane, neo-pentane, n-hexane, iso-hexane, neo-hexane, n-heptane, iso-heptane, neo-heptane, n-octane, iso-octane, neo-octane, or mixtures thereof. In particular embodiments, the feed comprises a mixture of n-pentane, iso-pentane, cyclo-pentane, and neo-pentane. In other particular embodiments, the hydrocarbon feed consists of n-heptane. In still other embodiments, the hydrocarbon feed consists of propane.

In certain embodiments of the process of the invention, wherein the hydrocarbon feed comprises one or more $C_2$-$C_{50}$ cyclic alkane and one or more $C_2$-$C_{50}$ acyclic alkane, and a molar ratio of cyclic alkane to acyclic alkane is from about 1:250 to about 250:1; or from about 1:10 to about 10:1.

In some embodiment of the process of the invention, the active material further comprises a support material. In particular embodiments, the active material further includes a support material is selected from zeolites, organoclays, $Al_2O_3$, $ZrO_2$, $SiO_2$, $SiO_2/Al_2O_3$, $SiO_2/TiO_2$, silica clay, silicon oxide/clay, or mixtures thereof.

In certain embodiments of the process of the invention, the active material has an oxygen capacity of from about 1 wt % to about 50 wt %, based on the weight of the mixed metal oxide. In particular embodiments, the active material has an oxygen capacity of from about 3 wt % to about 30 wt % based on the weight of the mixed metal oxide.

In some embodiments of the process of the invention, introducing the hydrocarbon feed to the active material is performed: at a mixed metal oxide/paraffin molar ratio of from 1,000:1 to 1:1,000; at a pressure of from about 15 psig to about 2,000 psig; and at a residence time of about 1 milli-second to about 48 hours.

In other embodiments of the process of the invention, introducing the hydrocarbon feed to the active material is performed: at a mixed metal oxide/paraffin molar ratio of from 100:1 to 1:100; at a temperature of about 100° C. to about 350° C.; at a pressure of from about 15 psig to about 1,000 psig; and at a residence time of about 1 milli-second to about 48 hours.

In still other embodiments of the process of the invention, introducing the hydrocarbon feed to the active material is performed: at a mixed metal oxide/paraffin molar ratio of from 10:1 to 1:10; at a temperature of about 150° C. to about 275° C.; at a pressure of from about 15 psig to about 200 psig; and at a residence time of about 1 milli-second to about 48 hours.

In some embodiments of the process of the invention, the process provides mono-olefin products at a selectivity of about 50% or greater; or at a selectivity of about 70% or greater.

In other embodiments of the process of the invention, the hydrocarbon feed comprises propane and the process provides a $C_2$-$C_{50}$ acyclic olefin that is propylene.

In another aspect, the invention provides a method of preparing an active material according to the invention comprising the steps of:
preparing an aqueous solution of one or more metal oxides or metal nitrates;
adjusting the pH with an alkali component to precipitate a mixed metal oxide; and
aging the mixed metal oxide in to obtain the active material.

In some embodiments of the preparation method of the invention, the aqueous solution comprises two or more metal oxides or metal nitrates or a mixture thereof. In particular embodiments, three or more metal oxides or metal nitrates or a mixture thereof.

In other embodiments of the preparation method of the invention, the alkali component is capable of adjusting the pH to pH 10.

In still other embodiments of the preparation method of the invention, the alkali material comprises Na, Li, K, Rb, and Cs. In particular embodiments, the alkali material is NaOH, $Na_2CO_3$, $LiNO_3$, or a combination thereof.

In yet other embodiments of the preparation method of the invention, the metal nitrates include one or more of $Al(NO_3)_3$, $Co(NO_3)_2$, $Mg(NO_3)_2$, $Cu(NO_3)_2$, or hydrates thereof.

In some embodiments of the preparation method of the invention, the method further comprises a step of filtering the mixed metal oxide to provide a wet filtrate after the aging step. In certain embodiments, the filtering of the mixed metal oxide is performed with an amount of water, optionally including acetone, sufficient to prevent the filtrate from becoming substantially dry.

In other embodiments of the preparation method of the invention, the method further comprises a step of drying the wet filtrate.

In still other embodiments of the preparation method of the invention, the method further comprises a second step of aging the wet filtrate in a solution of water, optionally including acetone, an alcohol, or both after the step of filtering the mixed metal oxide to provide a wet filtrate after the aging step.

In yet other embodiments of the preparation method of the invention, the method further comprises a step of calcining the mixed metal oxide after the aging step.

In still yet other embodiments of the preparation method of the invention, the method further comprises a step of calcining the mixed metal oxide after the second aging step.

DETAILED DESCRIPTION

Figure 1:
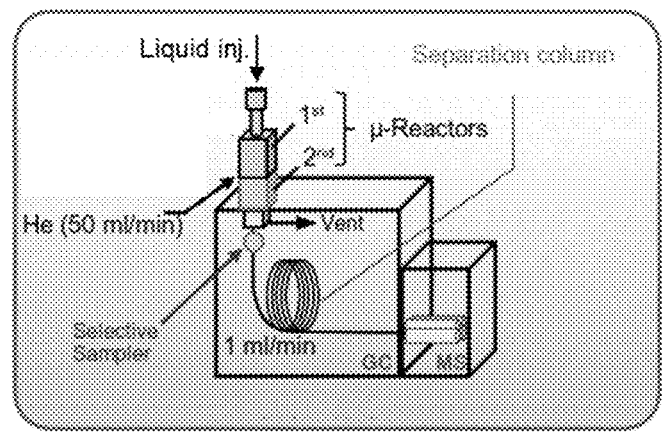
FIG. 1 depicts schematics of the tandem micro-reactor used for materials testing.

Throughout the entire specification, including the claims, the following terms shall have the indicated meanings. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than the broadest meaning understood by skilled artisans, such a special or clarifying definition will be expressly set forth in the specification in a definitional manner that provides the special or clarifying definition for the term or phrase.

For example, the following discussion contains a non-exhaustive list of definitions of several specific terms used in this disclosure (other terms may be defined or clarified in a definitional manner elsewhere herein). These definitions are intended to clarify the meanings of the terms used herein. It is believed that the terms are used in a manner consistent with their ordinary meaning, but the definitions are nonetheless specified here for clarity.

A/an: The articles "a" and "an" as used herein mean one or more when applied to any feature in embodiments and implementations of this disclosure described in the specification and claims. The use of "a" and "an" does not limit the meaning to a single feature unless such a limit is specifically stated. The term "a" or "an" entity refers to one or more of that entity. As such, the terms "a" (or "an"), "one or more" and "at least one" can be used interchangeably herein.

About: As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussion below regarding ranges and numerical data. All numerical values within the detailed description and the claims herein are modified by "about" or "approximately" the indicated value, and take into account experimental error and variations that would be expected by a person having ordinary skill in the art.

And/or: The term "and/or" placed between a first entity and a second entity means one of (1) the first entity, (2) the second entity, and (3) the first entity and the second entity. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements). As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of".

Comprising: In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. Any device or method or system described herein can be comprised of, can consist of, or can consist essentially of any one or more of the described elements.

Ranges: Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 200 should be interpreted to include not only the explicitly recited limits of 1 and about 200, but also to include individual sizes such as 2, 3, 4, etc. and sub-ranges such as 10 to 50, 20 to 100, etc. Similarly, it should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds). In the figures, like numerals denote like, or similar, structures and/or features; and each of the illustrated structures and/or features may not be discussed in detail herein with reference to the figures. Similarly, each structure and/or feature may not be explicitly labeled in the figures; and any structure and/or feature that is discussed herein with reference to the figures may be utilized with any other structure and/or feature without departing from the scope of the present disclosure.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

The term "active" refers to substance having an element or compound that participates as a reactant in a chemical reaction and may optionally have catalytic characteristics.

The term "alkane" means substantially saturated compounds containing hydrogen and carbon only, e.g., those containing ≤1% (molar basis) of unsaturated carbon atoms. The term alkane encompasses $C_2$ to $C_6$ linear, iso, and cyclo alkanes.

The term "$C_n$" hydrocarbon wherein n is a positive integer, e.g., 1, 2, 3, 4, or 5, means hydrocarbon having n carbon atom(s) per molecule.

The term "$C_{n+}$" hydrocarbon wherein n is a positive integer, e.g., 1, 2, 3, 4, or 5, means hydrocarbon having at least n carbon atom(s) per molecule.

The term "$C_{n-}$" hydrocarbon wherein n is a positive integer, e.g., 1, 2, 3, 4, or 5, means hydrocarbon having no more than n number of carbon atom(s) per molecule.

The term "cycle time" means the time from a first interval to the next first interval, including (i) intervening second, third, and/or fourth intervals and (ii) any dead-time between any pair of intervals.

The term "flow-through reactor" refers to a reactor design in which one or more reagents enter a reactor, typically an elongated channel or stirred vessel, at an inlet, flow through the reactor, and then a product mixture (including any unreacted reagents) is continuously or semi-continuously collected at an outlet. Flow-through reactors include continuous reactors, as well as semi-continuous reactors in which one phase flows continuously through a vessel containing a batch of another phase, e.g., fixed-bed reactors where a fluid phase passes through a solid phase of catalyst, reactant, active material, etc.

With respect to flow-through reactors, the term "region" means a location within the reactor, e.g., a specific volume within the reactor and/or a specific volume between a flow-through reactor and a second reactor, such as a second flow-through reactor. With respect to flow-through reactors, the term "zone", refers to a specific function being carried out at a location within the flow-through reactor. For example, a "reaction zone" or "reactor zone" is a volume within the reactor for conducting at least one of oxidative coupling, oxydehydrogenation and dehydrocyclization. Similarly, a "quench zone" or "quenching zone" is a location within the reactor for transferring heat from products of the catalytic hydrocarbon conversion, such as $C_{2+}$ olefin.

The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The term "oxidant" means any oxygen-bearing material which, under the conditions in the reaction zone, yields oxygen for transfer to the oxygen storage material, for storage with and subsequent release from the oxygen storage material to the oxidative coupling and/or oxydehydrogenation. While not wishing to be limited to theory, molecular oxygen atoms may be provided as a reactive gas in a gaseous zone and/or atomic oxygen may be provided from a catalyst surface as, for instance, reacted, adsorbed forms.

The terms "oxidized state" and "reduced state" refer to relative states of oxidation and reduction with respect to a reference state. For example, in compositions of the formulae $Mn^{+2}_{A1}Mn^{+3}_{B1}O_x$ and $Mn^{+2}_{A2}Mn^{+3}_{B2}O_y$, where x<y, A1>A2, and B1<B2, $Mn^{+2}_{A1}Mn^{+3}_{B1}O_x$ is the reduced state compound and $Mn^{+2}_{A2}Mn^{+3}_{B2}O_y$ is the oxidized state compound.

The term "oxydehydrogenation" means oxygen-assisted dehydrogenation of an alkane, particularly a $C_{2+}$ alkane, to produce an equivalent alkene and water.

The term "reaction stage" or "reactor stage" means at least one flow-through reactor, optionally including means for conducting one or more feeds thereto and/or one or more products away therefrom.

The term "residence time" means the average time duration for non-reacting (non-converting by oxidative coupling) molecules (such as He, $N_2$, Ar) having a molecular weight in the range of 4 to 40 to traverse the reactor or a defined zone within the reactor, such as a reaction zone of a oxidative coupling reactor.

The term "spinel" refers to the cubic crystalline structure of the spinel class of minerals typified by the mineral spinel, $MgAl_2O_4$, or a material having such a structure. A spinel has the general formula $AB_2X_4$, where X is an anion such as chalcogen, e.g., oxygen or sulfur, arranged in a cubic close-packed lattice, and A and B are cations, which may be different or the same, occupying some or all of the octahedral and tetrahedral sites in the lattice, also including the so-called inverse spinels where the B cations may occupy some or all of the typical A cation sites and vice versa. Although the charges of A and B in the prototypical spinel structure are +2 and +3, respectively, i.e., $A^{2+}B^{3+}_2X^{2-}_4$, other combinations incorporating divalent, trivalent, or tetravalent cations, including manganese, aluminum, magnesium, zinc, iron, chromium, titanium, silicon, and so on, are also possible.

The term "unsaturated" means a $C_n$ hydrocarbon containing at least one carbon atom directly bound to another carbon atom by a double or triple bond.

The present disclosure provides processes to convert paraffins to corresponding olefins and or heavier hydrocarbons under mild conditions (e.g., low temperature≤400° C.) using metal oxides. Furthermore, the present disclosure provides a process for upgrading a hydrocarbon feed, the process including: 1) introducing, at a temperature of from about 50° C. to about 500° C., a hydrocarbon feed comprising paraffins to a catalytic reduction unit and a first metal oxide comprising one or more group 1 to group 17 metal and one or more oxygen; ii) and obtaining a product mixture including one or more $C_3$-$C_{50}$ cyclic olefin, one or more $C_2$-$C_{50}$ acyclic olefin, one or more $C_5$-$C_{200}$ hydrocarbon, such as one or more $C_5$-$C_{100}$ heavier hydrocarbon, or a mixture thereof. Commercially valuable products, such as ethylene and propylene, can be formed using processes of the present disclosure.

As used herein, and unless otherwise indicated, a "metal oxide" refers to a metal oxide reagent/reactant that is reduced during a dehydrogenation process of the present disclosure. In comparison, a metal oxide catalyst would be regenerated to its original form (e.g. oxidation state) during a chemical reaction. Metal oxide reagents/reactants of the present disclosure can be regenerated from their reduced forms by treating the reduced form of the metal oxide to an oxidizing agent, as described in more detail below.

Dehydrogenation can reduce the first metal oxide to form a second metal oxide, also referred to as "a reduced metal oxide". Methods may include: i) introducing the reduced metal oxide to a catalytic oxidation unit; ii) and regenerating the first metal oxide in the catalytic oxidation unit by contacting the second metal oxide with an oxidizing agent (e.g., air).

In at least one embodiment, the conversion of paraffins (e.g., isoparaffins, normal-paraffins, neoparaffins, cyclic paraffins, or mixtures thereof) to one or more $C_3$-$C_{50}$ cyclic olefins, one or more $C_2$-$C_{50}$ acyclic olefins, one or more $C_5$-$C_{200}$ hydrocarbons, such as one or more $C_5$-$C_{100}$ hydrocarbons, or a mixture thereof (and the product mixture is substantially free of H$_2$ (e.g., <10 ppm, such as <5 ppm), is performed using a metal oxide, also referred to as metal oxide, is represented by Formula (I):

$$A_a(M1)_x(M2)_{y-x}(M3)_zO_{y+3/2z} \quad (I)$$

wherein:
A is an alkali metal;
M1 is a divalent metal;
M2 is a divalent metal;
M3 is a trivalent metal;
a is 0.01≤a≤4;
x is 0.01≤x≤4;
y is an integer from 2≤y≤4;
z is 0.25y≤z≤0.5y; and
the ratio a/x is from 0.01 to 1.0.

In at least one embodiment of the material of formula (I), A is selected from the group consisting of Na, Li, K, Rb, and Cs. In particular embodiments, A is Na.

In at least one embodiment of the material of formula (I), M1 is selected from the group consisting of Mn, Fe, Co, Ni, and Cu. In particular embodiments, M1 is Fe, Co, Ni, or Cu. In still other embodiments, M1 is Co and Cu. In other embodiments, M1 is Cu.

In at least one embodiment of the material of formula (I), M2 is selected from the group consisting of Mg, Ca, Sr, Ba, Zn, Co, Cu, Ni, and Fe. In particular embodiments, M2 is Mg, Co, or Ni. In still other embodiments, M2 is Mg.

In at least one embodiment of the material of formula (I), M3 is selected from the group consisting of Ga, Al, Fe, Co, Mn and Cr. In particular embodiments, M3 is Al.

In at least one embodiment of the material of formula (I), M2 is selected from the group consisting of Mg, Ca, Sr, Ba, Zn, Co, Cu, Ni, and Fe. In particular embodiments, M2 is Mg, Co, or Ni. In still other embodiments, M2 is Mg.

In at least one embodiment of the material of formula (I), z is chosen to satisfy charge neutralization.

Processes of the present disclosure may provide the following advantages: 1) reduction of the metal oxides can provide significant driving force to overcome thermodynamic limitations for paraffin conversions to olefins or heavier hydrocarbons, thus the reaction can be performed at significantly lower temperatures (e.g., <400° C.) than conventional approaches (e.g., steam cracking or dehydrogenation), resulting in reduction of greenhouse gas (GHG) emissions; 2) high selectivity for the formation of mono-olefins, such as cyclic olefins, can be obtained (such as a selectivity of 50% or greater), thus reducing or eliminating the formation of aromatics (e.g., benzene); 3) little or no direct contact of O$_2$ with hydrocarbons, thus avoiding undesired reactions of free O$_2$ with radical species that lead to over oxidation and improving selectivity vs. direct oxidation; 4) pure O$_2$ is not needed as the reduced metal oxides, instead air oxidation may be used. Olefins generated from a process of the present disclosure can be isolated as chemical intermediates, polymerized (e.g., oligomerized) to chemicals, fluids, or distillate products. For example, olefins generated from a process of the present disclosure can be used as monomers for polymers production (e.g., polyolefins production via metathesis).

All numerical values within the detailed description and the claims herein are modified by "about" or "approximately" the indicated value, and take into account experimental error and variations that would be expected by a person of ordinary skill in the art.

For purposes herein, the numbering scheme for the Periodic Table Groups is used as described in Chemical and Engineering News, 63(5), pg. 27 (1985). For example, a "Group 4 metal" is an element from Group 4 of the Periodic Table, e.g., Hf, Ti, or Zr.

Unless otherwise indicated, room temperature is 23° C.

A "polymer" has two or more of the same or different monomer ("mer") units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers.

As used herein, the term "base stock" means a hydrocarbon liquid useable as a major component of a lubricating oil. As used herein, the term "base oil" refers to a blend of base stocks useable as a major component of a lubricating oil. As used herein, the term "major component" means a component present in a lubricating oil in an amount of about 50 weight percent (wt %) or greater. As used herein, the term "minor component" means a component (e.g., one or more lubricating oil additives) present in a lubricating oil in an amount less than about 50 wt %.

The term "continuous" means a system that operates without interruption or cessation. For example a continuous process to produce an olefin and or a hydrocarbon product would be one where the reactants are continually introduced into one or more reactors and the olefin and or the hydrocarbon product can be continually withdrawn during a conversion process (e.g., dehydrogenation process; dehydrogenative coupling).

For purposes of this disclosure and claims thereto, the term "substituted" means that a hydrogen atom in the compound or group in question has been replaced with a group or atom other than hydrogen. The replacing group or atom is called a substituent. Substituents can be, e.g., a substituted or unsubstituted hydrocarbyl group, a heteroatom, and the like. For example, a "substituted hydrocarbyl" is a group made of carbon and hydrogen where at least one hydrogen therein is replaced by a non-hydrogen atom or group. A heteroatom can be nitrogen, sulfur, oxygen, halogen, etc.

The term "alkenyl" means a straight-chain, branched-chain, or cyclic hydrocarbon radical having one or more double bonds. These alkenyl radicals may be optionally substituted. Examples of suitable alkenyl radicals can include ethenyl, propenyl, allyl, 1,4-butadienyl cyclopropenyl, cyclobutenyl, cyclopentenyl, cyclohexenyl, cyclooctenyl, and the like, including their substituted analogues.

The term "alkoxy" or "alkoxide" means an alkyl ether or aryl ether radical where the term alkyl is as defined above. Examples of suitable alkyl ether radicals can include methoxy, ethoxy, n-propoxy, iso-propoxy, n-butoxy, iso-butoxy, sec-butoxy, tert-butoxy, phenoxyl, and the like.

The term "aryl" or "aryl group" means a six carbon aromatic ring and the substituted variants thereof, such as phenyl, 2-methyl-phenyl, xylyl, 4-bromo-xylyl. Likewise, heteroaryl means an aryl group where a ring carbon atom (or two or three ring carbon atoms) has been replaced with a heteroatom, such as N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

Reference to an alkyl, alkenyl, alkoxide, or aryl group without specifying a particular isomer (e.g., butyl) expressly discloses all isomers (e.g., n-butyl, iso-butyl, sec-butyl, and tert-butyl).

For purposes of the present disclosure, "alkoxides" include those where the alkyl group is a $C_1$ to $C_{10}$ hydrocarbyl. The alkyl group may be straight chain, branched, or cyclic. The alkyl group may be saturated or unsaturated. In at least one embodiment, the alkyl group may include at least one aromatic group.

The terms "hydrocarbyl radical," "hydrocarbyl," and "hydrocarbyl group," are used interchangeably. Likewise, the terms "group," "radical," and "substituent" are also used interchangeably. For purposes of this disclosure, "hydrocarbyl radical" is defined to be $C_1$ to $C_{100}$ radicals, that may be linear, branched, or cyclic, and when cyclic, aromatic or non-aromatic. Examples of such radicals can include methyl, ethyl, n-propyl, isopropyl, n-butyl, isobutyl, sec-butyl, tert-butyl, pentyl, iso-amyl, hexyl, octyl, cyclopropyl, cyclobutyl, cyclopentyl, cyclohexyl, cyclooctyl, and the like including their substituted analogues.

The term "aralkyl" means a univalent radical derived from an alkyl radical by replacing one or more hydrogen atoms by one or more aryl groups.

The term "alkaryl" means an aryl-substituted alkyl radical (e.g., propyl-phenyl), such as a radical in which an aryl group is substituted for a hydrogen atom of an alkyl group.

The term "alkynyl" (also referred to as "ynyl") means a univalent aliphatic hydrocarbon radical derived from an alkyne.

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom-substituted ring.

The term "olefin" refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched linear, or cyclic.

The term "alpha-olefin" refers to an olefin having a terminal carbon-to-carbon double bond in the structure thereof ((RaRb)—C=CH$_2$, where Ra and Rb can be independently hydrogen or any hydrocarbyl group; such as Ra is hydrogen and Rb is an alkyl group). A "linear alpha-olefin" is an alpha-olefin defined in this paragraph wherein Ra is hydrogen, and Rb is hydrogen or a linear alkyl group.

For the purposes of the present disclosure, ethylene shall be considered an alpha-olefin.

The term "vinyl" means an olefin having the following formula:

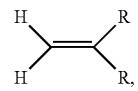

wherein R is a hydrocarbyl group, such as a saturated hydrocarbyl group.

The term "vinylidene" means an olefin having the following formula:

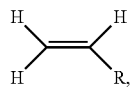

wherein each instance of R is independently a hydrocarbyl group, such as a saturated hydrocarbyl group.

The term "vinylene" or "1,2-di-substituted vinylene" means (i) an olefin having the following formula (which is a "cis-" conformation):

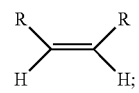

or (ii) an olefin having the following formula (which is a "trans-" conformation):

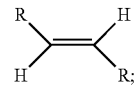

or (iii) a mixture of (i) and (ii) at any proportion thereof, wherein each instance of R is independently a hydrocarbyl group, such as saturated hydrocarbyl group.

The term "internal olefin" includes olefins that are vinylenes.

The term "tri-substituted vinylene" means an olefin having the following formula:

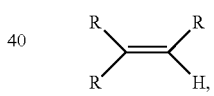

wherein each instance of R is independently a hydrocarbyl group, such as a saturated hydrocarbyl group.

An internal olefin (e.g., monomers) of the present disclosure can be a linear or branched $C_4$-$C_{50}$ olefin having one or more carbon-carbon double bonds along the olefin backbone (also referred to as "internal unsaturation") instead of, or in addition to, a carbon-carbon double bond at a terminus of the olefin (also referred to as "terminal unsaturation"). Linear or branched $C_4$-$C_{50}$ internal olefins may be referred to as $C_4$-$C_{50}$ internal-olefins. In addition to internal unsaturations, a $C_4$-$C_{50}$ internal olefin may additionally have one or more terminal unsaturations. An internal olefin can have one or more cis-conformations or one or more trans-conformations.

In at least one embodiment, an internal olefin is selected from a cis-configuration, trans-configuration, or mixture thereof of one or more of 2-butene, 2-pentene, 2-hexene, 3-hexene, 2-heptene, 3-heptene, 2-octene, 3-octene, 4-octene, 2-nonene, 3-nonene, 4-nonene, 2-decene, 3-decene, 4-decene, and 5-decene. Internal olefins of the present disclosure can be obtained from commercial sources (such as Sigma Aldrich or TCI) and/or may be obtained from refined hydrocarbon feeds such as fluid catalytic cracking (FCC) gasoline or coker naphtha.

Dehydrogenation and Dehydrogenative Coupling Processes and the Metal Oxide Regeneration Process The present disclosure provides processes for converting a hydrocarbon feedstock (e.g., heavy naphtha, biomass, light paraffins, etc.) or a mix of two or more hydrocarbon feedstocks, comprising contacting the feedstock with one or more metal oxide $A_a(M1)_x(M2)_{y-x}(M3)_zO_{y+3/2z}$ (I), and further obtaining a product mixture including one or more $C_3$-$C_{50}$ cyclic olefin, one or more $C_2$-$C_{50}$ acyclic olefin, one or more $C_5$-$C_{200}$ hydrocarbon, such as one or more $C_5$-$C_{100}$ hydrocarbon, or a mixture thereof. In at least one embodiment, the product mixture is substantially free of H2 (e.g., <1000 ppm, <500 ppm, such as <100 ppm, such as <10 ppm, such as <5 ppm, such as <1 ppm). The hydrocarbon feedstock can be one or more $C_3$-$C_{50}$ cyclic alkanes, one or more $C_2$-$C_{50}$ acyclic alkanes (e.g., iso-, linear, normal, and or branched (substituted) alkanes).

Processes of the present disclosure may be performed via a cyclic process (chemical looping or pulsed feed) based on a circulating fluidized bed process and system, or a switched (between air and the hydrocarbon feedstock) feed fluidized bed system, or switched feed fixed bed system, in which air and the hydrocarbon feedstock are alternated. Fine droplets or vapor of the hydrocarbon feedstock and air can be introduced over the metal oxide bed along with the oxygen carrier (e.g., metal oxide (I)), for example.

A process can be operated in a cyclic mode without moving the solids, thus by cycling through a paraffin conversion process and an oxide regeneration process (e.g., in a reverse-flow reactor), or in a pulse fashion (as shown in FIG. 1) by moving the solids through the paraffin conversion unit and oxide regeneration unit (e.g., moving solid beds, fluidized beds). Alternatively, the metal oxide can be shaped into one or more membrane reactor(s), planar or tubular, providing continuous operations with paraffin conversion and metal oxide regeneration, which can occur on separate sides of the membrane.

In addition to the reactivity toward paraffins and the capability to regenerate the first metal oxide (by oxidizing the second metal oxide (also referred to as "spent material" or "reduced material")) via air flow, the active oxygen content, also referred to as the "oxygen capacity", can be another important parameter in selecting the metal oxides. The oxygen capacity of the metal oxides will be discussed further.

Processes may include: i) contacting a first metal oxide (e.g., metal oxide $A_a(M1)_x(M2)_{y-x}(M3)_zO_{y+3/2z}$ (I)) with a reducing substance (e.g., paraffins); ii) reducing the metal oxide, such as metal oxide with the reducing substance (e.g., paraffins) to a reduced metal oxide $A_a(M1)_x(M2)_{y-x}(M3)_zO_{y+3/2z-1}$ and iii) regenerating the first metal oxide (e.g., $A_a(M1)_x(M2)_{y-x}(M3)_zO_{y+3/2z}$ (I) using an oxidizing agent (e.g., air) at a partial pressure of about 1 psig to about 100 psig (e.g., metal oxide (I)).

The reducing substance (e.g., paraffins) can be one or more gas, liquid, or solid substance, or a mixture thereof. For example, when the reducing substance (e.g., paraffins) is gas, the reducing substance may be introduced to the catalytic reduction unit at a partial pressure of from about 15 psig to about 2000 psig, such as from about 15 psig to about 1,000 psig, such as from about 15 psig to about 200 psig. In at least one embodiment, contacting the metal oxide $A_a(M1)_x(M2)_{y-x}(M3)_zO_{y+3/2z}$ (I) includes cyclically exposing a fixed bed containing the metal oxide $A_a(M1)_x(M2)_{y-x}(M3)_zO_{y+3/2z}$ (I) to the reducing substance (e.g., paraffins) and to the oxidizing gas (e.g., air). In an alternate embodiment, contacting the metal oxide $A_a(M1)_x(M2)_{y-x}(M3)_zO_{y+3/2z}$ (I) includes cyclically exposing the fixed bed containing the metal oxide $A_a(M1)_x(M2)_{y-x}(M3)_zO_{y+3/2z}$ (I) to a continuous feed of the oxidizing gas (e.g., air) and intermittently feeding the reducing substance (e.g., paraffins). In another alternative embodiment, contacting the metal oxide $A_a(M1)_x(M2)_{y-x}(M3)_zO_{y+3/2z}$ (I) includes cyclically exposing the fixed bed containing the metal oxide $A_a(M1)_x(M2)_{y-x}(M3)_zO_{y+3/2z}$ (I) to a continuous feed of the reducing substance (e.g., paraffins) and intermittently feeding the oxidizing gas (e.g., air).

Furthermore, contacting the metal oxide $(A_a(M1)_x(M2)_{y-x}(M3)_zO_{y+3/2z}$ (I) may include: i) circulating the metal oxide $A_a(M1)_x(M2)_{y-x}(M3)_zO_{y+3/2z}$ (I) in a fluidized bed system during the cyclic contacting of the metal oxide (I), with a reducing substance (e.g., paraffins); ii) introducing the second metal oxide $A_a(M1)_x(M2)_{y-x}(M3)_zO_{y+3/2z-1}$ to an oxidizing agent (e.g., oxidizing gas, such as air). Contacting the metal oxide $A_a(M1)_x(M2)_{y-x}(M3)_zO_{y+3/2z}$ (I) a may also include circulating the metal oxide(s) in a fluidized bed system wherein the metal oxide(s) (I) can be reduced in a reactor and can be circulated to a regeneration unit for contacting the second metal oxide (also referred to as the reduced metal oxide(s) $A_a(M1)_x(M2)_{y-x}(M3)_zO_{y+3/2z}$) with the oxidizing gas (e.g., air).

In at least one embodiment, the process includes separating the $C_3$-$C_{50}$ cyclic olefins, $C_2$-$C_{50}$ acyclic olefins, and or $C_5$-$C_{200}$ hydrocarbon products, such as $C_5$-$C_{100}$ heavier hydrocarbon products via distillation.

Accordingly, the present disclosure can provide a process for a cyclic catalytic partial oxidation of a hydrocarbon feedstock which may include: (i) as an oxidation process, passing air over one or more second metal oxide(s) (e.g., $A_a(M1)_x(M2)_{y-x}(M3)_zO_{y+3/2z-1}$) comprising a metal or metal oxide that can be configured to capture oxygen from the air to produce an oxidized metal oxide, such as (I), and producing an effluent including oxygen-reduced air; (ii) passing the hydrocarbon feedstock over the oxidized metal oxide(s), such as (I), in a reduction process to create a product gas comprising olefins and or heavier hydrocarbons, wherein the oxidized metal oxide(s), such as (I), can become reduced or partially reduced, thus creating a second metal oxide (e.g., $A_a(M1)_x(M2)_{y-x}(M3)_zO_{y+3/2z-1}$); and (iii) repeating (i) to oxidize the reduced metal oxide(s) (e.g., $A_a(M1)_x(M2)_{y-x}(M3)_zO_{y+3/2z-1}$). For example, air can be passed continuously over the oxygen carrying (or oxygen storing) metal oxide(s) (e.g., $A_a(M1)_x(M2)_{y-x}(M3)_zO_{y+3/2z-1}$), and pulses of hydrocarbon feedstock can be delivered periodically, by co-feeding with the air flow. In a cyclic (chemical looping or pulsed feed) mode, fine droplets or vapor of the hydrocarbon feedstock and air can be introduced over the oxygen carrying bed along with an oxygen carrying (or oxygen storing) metal oxide(s) (e.g., $A_a(M1)_x(M2)_{y-x}(M3)_zO_{y+3/2z-1}$). The feed to the bed can be switched between this mixture and air (or other oxidant). Alternatively, air can be fed continuously to the bed and the hydrocarbon feed (such as a liquid hydrocarbon feed) can be delivered to the reactor (as droplets or vapor, for example).

The hydrocarbon feedstock may include, in whole or in part, a gas oil (e.g., light, medium, or heavy gas oil) having an initial boiling point above 200° C., a 50% point of at least 260° C. and an end point of at least 350° C. The feedstock may also include vacuum gas oils, thermal oils, residual oils, cycle stocks, whole top crudes, tar sand oils, shale oils, synthetic fuels, heavy hydrocarbon fractions derived from the destructive hydrogenation of coal, tar, pitches, asphalts, hydrotreated feedstocks derived from any of the foregoing. The hydrocarbon feed can be, isoparaffins, normal-paraffins, neoparaffins, cyclic paraffins, or mixtures thereof, such as a naphtha feed comprising one or more $C_3$-$C_{50}$ cyclic alkanes (e.g., cyclopropane, cyclobutane, cyclopentane, cyclohexane, cycloheptane, cyclooctane, or mixtures thereof), one or more $C_2$-$C_{50}$ acyclic alkanes (e.g, n-propane, n-butane, iso-butane, n-pentane, iso-pentane, neo-pentane, n-hexane, iso-hexane, neo-hexane, n-heptane, iso-heptane, neo-heptane, n-octane, iso-octane, neo-octane, or mixtures thereof), or a mixture thereof (e.g., n-pentane, iso-pentane, cyclo-pentane, and or neo-pentane).

Heavy naphtha may include both paraffins and naphthenes (e.g., coal, shale, or petroleum). For example, a naphtha may include from about 15 wt % to about 30 wt % paraffins, from about 5 wt % to about 20 wt % cyclo-paraffins, from about 10 wt % to about 30 wt % olefins, from about 1 wt % to about 10 wt % cycloolefins, and from about 10 wt % to about 40 wt % aromatics. Heavy naphtha can be converted to olefins, such as mono-olefins, using dehydrogenation. The heavy naphtha feed can be processed "as-is", or optionally separated into paraffin and naphthene fractions, or further fractionated to individual carbon number. Dehydrogenation processes of the present disclosure include the dehydrogenation of $C_2$-$C_{50}$ acyclic alkanes and $C_3$-$C_{50}$ cyclic alkanes in a heavy naphtha range (e.g., coker naphtha; catalytic naphtha), including paraffins and or naphthenes, to form $C_2$-$C_{50}$ acyclic olefins and $C_3$-$C_{50}$ cyclic olefins. The paraffins can be in a gaseous and or a liquid state. In at least one embodiment, the hydrocarbon feed comprises one or more $C_3$-$C_{50}$ cyclic alkane and one or more $C_2$-$C_{50}$ acyclic alkane, and a molar ratio of cyclic alkane to acyclic alkane is from about 1:250 to about 250:1, such as from 1:10 to 10:1.

FIG. 1 illustrates a chemical looping process for dehydrogenation and or dehydrogenative coupling, and regeneration of the metal oxide(s) using air. The chemical looping process in which a metal oxide $A_a(M1)_x(M2)_{y-x}(M3)_zO_{y+3/2z}$ (I) can be cyclically reduced to form a second metal oxide that is then oxidized while a paraffin feed can be converted via dehydrogenation to a corresponding olefin and or converted via dehydrogenative coupling to heavier hydrocarbon products. In the cyclic (chemical looping or pulsed feed) mode, fine droplets or vapor of the fuel and air can be introduced over the metal oxide bed along with a carrier gas. The feed to the bed can be switched between the resulting mixture and any suitable oxidizing agent (e.g., air). Alternatively, air can be fed continuously to the bed and the liquid feed can be delivered to the reactor (as droplets or vapor) intermittently (as pulsed feed), for example. Finally, the liquid feed may be continuously or semi-continuously fed into a reactor containing the metal oxide(s) (e.g., $A_a(M1)_x(M2)_{y-x}(M3)_zO_{y+3/2z}$ (I)), such as a catalytic reduction unit, which continuously circulates between the reactor (e.g., catalytic reduction unit) and a regenerator in which the second metal oxide(s) $A_a(M1)_x(M2)_{y-x}(M3)_zO_{y+3/2z}$ (I) can be oxidized (e.g., catalytic oxidation unit). Furthermore, the feed to the reactor can be switched between air and a gaseous fuel (natural gas, or other hydrocarbons). Alternatively, the fuel may be fed to a reactor (e.g., catalytic reduction unit) in which one or more metal oxide(s) (e.g., $A_a(M1)_x(M2)_{y-x}(M3)_zO_{y+3/2z}$ (I)) can be continuously circulated between a fuel partial oxidation reactor and a regenerator (e.g., catalytic oxidation unit).

In at least one embodiment, the hydrocarbon feedstock conversion, such as the paraffin conversion, to $C_3$-$C_{50}$ cyclic olefins, $C_2$-$C_{50}$ acyclic olefins, and or $C_5$-$C_{200}$ hydrocarbon products, such as $C_5$-$C_{100}$ heavier hydrocarbon products, is performed at an metal oxide (e.g., $A_a(M1)_x(M2)_{y-x}(M3)_zO_{y+3/2z}$ (I))/paraffin molar ratio of from 1,000:1 to 1:1,000, such as from 100:1 to 1:100, such as from 50:1 to 1:50, such as from 10:1 to 1:10.

The hydrocarbon feedstock conversion, such as the paraffin conversion, to $C_3$-$C_{50}$ cyclic olefins, $C_2$-$C_{50}$ acyclic olefins, and or $C_5$-$C_{200}$ hydrocarbon products, such as $C_5$-$C_{100}$ hydrocarbon products, can be performed at a temperature of from about 50° C. to about 500° C., such as from about 75° C. to about 450° C., such as from about 100° C. to about 400° C., such as from about 150° C. to about 300° C. (e.g., 250° C.).

In at least one embodiment, the hydrocarbon feedstock conversion, such as the paraffin conversion, to $C_3$-$C_{50}$ cyclic olefins, $C_2$-$C_{50}$ acyclic olefins, and or $C_5$-$C_{200}$ hydrocarbon products, such as $C_5$-$C_{100}$ hydrocarbon products, is performed at a pressure of from about 15 psig to about 2,000 psig, such as from about 15 psig to about 1,000 psig, such as from about 15 psig to about 500 psig.

The hydrocarbon feedstock conversion, such as the paraffin conversion, to $C_3$-$C_{50}$ cyclic olefins, $C_2$-$C_{50}$ acyclic olefins, and or $C_5$-$C_{200}$ hydrocarbon products, such as $C_5$-$C_{100}$ hydrocarbon products, can be performed at a residence time of about 1 milli-second to about 48 hours, such as about 10 milli-seconds to about 24 hours, such as about 5 minutes to about 20 hours.

In at least one embodiment, the metal oxide(s) (e.g., $A_a(M1)_x(M2)_{y-x}(M3)_zO_{y+3/2z}$ (I) regeneration process is performed at a temperature of from about 50° C. to about 1,000° C., such as from about 75° C. to about 750° C., such as from about 100° C. to about 500° C., such as from about 150° C. to about 300° C. (e.g., 250° C.); at a pressure of from about 15 psig to about 2,000 psig, such as from about 50 psig to about 1,500 psig, such as from about 100 psig to about 1,000 psig; at a residence time of about 1 milli-second to about 48 hours, such as about 10 milli-seconds to about 24 hours, such as about 5 minutes to about 20 hours.

The hydrocarbon feed may contain one or more hydrocarbon feeds described above. A dehydrogenation process, and or a dehydrogenative coupling process, can involve contacting a $C_3$-$C_{50}$ cyclic alkane and or a $C_2$-$C_{50}$ acyclic alkane feed with one or more metal oxide(s) (e.g., $A_a(M1)_x(M2)_{y-x}(M3)_zO_{y+3/2z}$ (I)) including platinum group metals, alloys, oxides, carbides, nitrides, and or sulfides of individual transition metal and or a mixed metal compound. The metal oxide(s) (e.g., $A_a(M1)_x(M2)_{y-x}(M3)_zO_{y+3/2z}$ (I)) can be bulk and or supported. Suitable supports include non-acidic oxides including silica, theta-alumina, zirconia, titania, ceria, non-acidic clays, or basic oxides (such as magnesia, hydrotalcites, or lanthanum oxide) In at least one embodiment, the dehydrogenation process, and or a dehydrogenative coupling process, of $C_3$-$C_{50}$ cyclic alkane and or a $C_2$-$C_{50}$ acyclic alkane, is mediated using one or more metal oxide(s) selected from $CuO$, $CuO_2$, $Ag_2O$, $Na_2O_2$, $ZnO$, $ZnO_2$, $NiO$, $Ni_2O_3$, $CrO_z$, $VO_z$, $FeO_z$, $Fe_2O_3$, $CoO_z$, $Co_2O_3$, $Co_3O_4$, $MnO_z$, $BaO_2$, $CuO/SiO_2$, $CuO/Al_2O_3$ $VO_z/Al_2O_3$, $YMnO_4$, $YMnO_{3.5}$, and or $MgO_2$. The $C_2$-$C_{50}$ acyclic olefins products, $C_3$-$C_{50}$ cyclic olefins products, and or $C_5$-$C_{200}$ hydrocarbon products, such as $C_5$-$C_{100}$ hydrocarbon products, can be substituted and or non-substituted olefins products. In at least one embodiment, the product mixture is substantially free of $H_2$ (e.g., <1000 ppm, <500 ppm, such as <100 ppm, such as <10 ppm, such as <5 ppm, such as <1 ppm)).

In a dehydrogenation process, and or a dehydrogenative coupling process, a feed stream including at least 2 wt % of $C_2$ to $C_{50}$ cyclic alkanes and or $C_2$ to $C_{50}$ acyclic alkanes can be contacted with a metal oxide suitable for a dehydrogenation process and or a dehydrogenative coupling process, with or without the presence of a solvent, such as the hydrocarbons including $C_2$ to $C_{50}$ cyclic alkanes and or $C_2$ to $C_{50}$ acyclic alkanes of the feed stream can be used directly as solvent.

Optionally one or more solvent(s) can be used for a process of the present disclosure. The solvent may be a saturated hydrocarbon or an aromatic solvent such as n-hexane, n-heptane, cyclohexane, benzene, toluene, xylenes, or a mixture thereof. Contacting the metal oxide with a feed stream comprising the $C_2$ to $C_{50}$ alkanes may be carried out in an atmosphere inert under the process conditions, such as in nitrogen, argon, or a mixture thereof. Naphtha, including both paraffins and naphthenes, may include various ranges of cyclic and acyclic alkanes. For example, $C_3$-$C_{50}$ cyclic alkanes can be cyclopentane, cyclobutane, cyclopentane, cyclohexane, cycloheptane, cyclooctane. Examples of $C_2$-$C_{50}$ acyclic alkanes can be n-propane, n-butane, iso-butane, n-pentane, iso-pentane, neo-pentane, n-hexane, iso-hexane, neo-hexane, n-heptane, iso-heptane, neo-heptane, n-octane, iso-octane, neo-octane, or mixtures thereof.

A molar ratio of one or more cyclic alkanes to acyclic alkanes can be from about 1:1,000 to about 1,000:1, such as from about 1:700 to about 700:1, such as from about 1:500 to about 500:1, such as from about 1:250 to about 250:1, such as from about 1:100 to about 100:1, such as from about 1:50 to about 50:1, such as from about 1:10 to about 10:1.

In at least one embodiment, a dehydrogenation process, and or a dehydrogenative coupling process, is performed at a temperature of 500° C. or less, such as from about 100° C. to about 450° C., such as from about 150° C. to about 350° C. (e.g., 275° C.). A dehydrogenation process, and or a dehydrogenative coupling process, of the present disclosure may be carried out by mixing a solution of $C_3$-$C_{50}$ cyclic alkanes and $C_2$-$C_{50}$ acyclic alkanes and one or more metal oxide(s), cooling the solution, and optionally allowing the mixture to increase in temperature.

In at least one embodiment, the process for the production of one or more $C_3$-$C_{50}$ cyclic olefins, one or more $C_2$-$C_{50}$ acyclic olefins, one or more $C_5$-$C_{200}$ hydrocarbons (such as $C_5$-$C_{100}$ heavier hydrocarbons), or a mixture thereof, includes: dehydrogenating, and or dehydrogenating coupling process, at least one $C_2$-$C_{50}$ acyclic alkane and at least one $C_3$-$C_{50}$ cyclic alkane by contacting the at least one $C_2$-$C_{50}$ acyclic alkane and the at least one $C_2$-$C_{50}$ cyclic alkane with one or more metal oxide(s) (e.g., $A_a(M1)_x(M2)_{y-x}(M3)_zO_{y+3/2z}$ (I)) in at least one solution dehydrogenation/dehydrogenative coupling reactor at a reactor pressure of from about 15 psig to about 2,000 psig, and or a reactor temperature of from about 100° C. to about 450° C. The $C_2$-$C_{50}$ acyclic olefins, $C_3$-$C_{50}$ cyclic olefins products, and or $C_5$-$C_{200}$ hydrocarbons (such as $C_5$-$C_{100}$ heavier hydrocarbons) can be recovered and analyzed by GC.

Metal Oxides for Dehydrogenation and Dehydrogenative Coupling Processes

In at least one embodiment, the conversion of paraffins (e.g., isoparaffins, normal-paraffins, neoparaffins, cyclic paraffins, or mixtures thereof) to one or more $C_3$-$C_{50}$ cyclic olefins, one or more $C_2$-$C_{50}$ acyclic olefins, one or more $C_5$-$C_{200}$ hydrocarbons (such as $C_5$-$C_{100}$ heavier hydrocarbons), or a mixture thereof, is performed using a metal oxide, also referred to as metal oxide, that is represented by Formula (I):

$$A_a(M1)_x(M2)_{y-x}(M3)_zO_{y+3/2z} \qquad (I)$$

wherein:
A is an alkali metal;
M1 is a divalent metal;
M2 is a divalent metal;
M3 is a trivalent metal;
a is $0.01 \leq a \leq 4$;
x is $0.01 \leq x \leq 4$;
y is an integer from $2 \leq y \leq 4$;
z is $0.25y \leq z \leq 0.5y$; and
the ratio a/x is from 0.01 to 1.0.

Suitable examples of metal oxide $A_a(M1)_x(M2)_{y-x}(M3)_zO_{y+3/2z}$ (I) can be, but are not limited to, $CuO/SiO_2$, $CuO/Al_2O_3$, $VO_z/Al_2O_{3.5}$, $YMnO_4$, $YMnO_{3.5}$, where z is in the range of 1 to 2.5. Metal oxide(s) $A_a(M1)_x(M2)_{y-x}(M3)_zO_{y+3/2z}$ (I) of the present disclosure may include platinum group metals (e.g., Pd, Rh, Pt), alloys (e.g., bimetallic Pt—Fe catalysts, Cu—Al alloy catalyst, Pt—Zn alloy nanocluster catalyst), oxides, carbides (e.g., bulk W—Mo mixed carbides, Mo carbide modified nanocarbon catalysts), nitrides (e.g., B—N catalyst), and or sulfides (e.g., Mo-sulfide-alumina catalyst) of individual transition metal and or mixed metal catalyst. The metal oxide(s) (e.g., $A_a(M1)_x(M2)_{y-x}(M3)_zO_{y+3/2z}$ (I)) can be bulk and or supported.

For purposes of the present disclosure, a metal oxide loading % (based on the concentration of the alkanes) can be from about 0.01 mol % to about 50 mol %, such as from about 0.1 mol % to about 25 mol %, such as from about 0.2 mol % to about 10 mol %, such as from about 0.5 mol % to about 5 mol %, such as about 0.2 mol %, for example.

The paraffin dehydrogenation to olefins, as well as the dehydrogenative coupling to heavier paraffins, are thermodynamically unfavored, and conversions are equilibrium limited, i.e. no matter how effective a catalyst is, the best conversion the catalyst can achieve is what the reaction equilibrium will allow. The free energy $\Delta G$ (kcal/mol) for the dehydrogenation reaction can only become favorable when the temperature is at least about 600° C. Consequently, a large amount of energy is needed in order to enable the dehydrogenation reaction and the dehydrogenative coupling. In addition, the catalysts tend to deactivate quickly due to coking, and frequent regeneration can be necessary. In the case of dehydrogenative coupling, the free energy $\Delta G$ (kcal/mol) becomes favorable at very low temperatures (e.g., <0° C.). In contrast, when using a metal oxide (e.g., CuO) for the paraffin dehydrogenation to olefins, as well as the dehydrogenative coupling to heavier paraffins, the free energy becomes much more favorable for dehydrogenation, for example, with a free energy becoming negative (e.g., $\Delta G$ of from about 0 kcal/mol to about −100 kcal/mol, such as from about −5 kcal/mol to about −75 kcal/mol), and or at a temperature range of from 0° C. to 1,000° C., thus eliminating the equilibrium limitation.

Hence, the redox metal oxides can enable the conversion processes of the hydrocarbon feedstocks to be thermodynamically favorable, thus allowing the dehydrogenation reaction, as well as the dehydrogenative coupling, to occur at much lower temperatures than that of conventional processes (e.g., ≤500° C.). Processes of the present disclosure can enable reducing the energy intensity and the greenhouse gas emissions. While similar effects can be achieved using alternative strategies such as oxidative dehydrogenation or selective hydrogen combustion, both of these processes need a co-feed of O2 with hydrocarbons, which can create a combustible air/fuel mix. Additionally, a direct contact of O2 with hydrocarbons can result in undesired radicals and gas phase reactions, leading to over-oxidation and low selectivity of the conventional catalysts to the hydrocarbon feedstock (e.g., selectivity of about 45% or lower).

Metal oxides (e.g., $A_a(M1)_x(M2)_{y-x}(M3)_zO_{y+3/2z}$ (I)) utilized in the processes described herein can be prepared by any suitable technique such as co-precipitation, urea precipitation, or sol-gel synthesis. The metal oxide oxygen carryings (e.g., $A_a(M1)_x(M2)_{y-x}(M3)_zO_{y+3/2z}$ (I)) may take the form of granules, pellets, or monolithic structures. Coal ash may also be used as a support for selected unary (e.g., $Fe_2O_3$, $Fe_3O_4$, $MnO_z$, $CoO_z$, and $NiO_z$) and binary (e.g., $FeTiO_3$, $Mn_{1-x}Cu_yO_z$, and $Mn_{1-x}Fe_yO_z$) metal oxides. The metal oxide materials (e.g., $A_a(M1)_x(M2)_{y-x}(M3)_zO_{y+3/2z}$ (I)) and coal ash may be bound with an inorganic binder such as silica, titania, magnesia, boehmite, or zirconia. As indicated above, fixed beds of the metal oxides (e.g., $A_a(M1)_x(M2)_{y-x}(M3)_zO_{y+3/2z}$ (I)) may be either exposed to alternating air and feed, or to a continuous feed of air and intermittent (pulsed) feed of feedstock. In at least one embodiment, fluidized bed systems comprise one, two, or more fluidized beds. Alternating exposure to air and hydrocarbons feed can be achieved either by means of a set of valves (for a single bed) or in the case of two or more beds by circulation of the oxygen carrier between the reactor and regenerator beds.

The first metal oxides (e.g., $A_a(M1)_x(M2)_{y-x}(M3)_zO_{y+3/2z}$ (I)) can be regenerated by oxidizing the second metal oxides (e.g., $A_a(M1)_x(M2)_{y-x}(M3)_zO_{y+3/2z-1}$), since the metal oxides are oxygen carriers, thus enabling oxidative conversions without directly contacting O2 with the feed. Air can be used for purposes of the present disclosure (instead of pure O2 in the cases of oxidative dehydrogenation and selective hydrogen combustion), which also reduces the cost and energy intensity of the process.

In certain embodiments, the active material has a structure having X-Ray diffraction peaks at d-spacing corresponding to three characteristic features of an M2O rocksalt phase, d1, d2 and d3, wherein the three characteristic d-spacing are:

2.41 Å<$d1$<2.49 Å, 2.09 Å<$d2$<2.15 Å, 1.48 Å<$d3$<1.52 Å;

and wherein the structure is substantially free of X-Ray diffraction peaks at d-spacing corresponding to an M1O phase.

Exemplary d-spacing include, but are not limited to:

CuO: $d1$=2.52 Å(2theta=35.5°), $d2$=2.32 Å(2theta=38.7°), and $d3$=1.87 Å(2theta=48.7°)

MgO: $d1$=2.43 Å(2theta=36.9°), $d2$=2.11 Å(2theta=42.9°), $d3$=1.49 Å(2theta=62.3°)

NiO: $d1$=2.41 Å(2theta=37.2°), $d2$=2.09 Å(2theta=43.3°), $d3$=1.48 Å(2theta=62.9°).

CoO: $d1$=2.46 Å(2theta=36.5°), $d2$=2.13 Å(2theta=42.4°), $d3$=1.51 Å(2theta=61.5°)

FeO: $d1$=2.49 Å(2theta=36.0°), $d2$=2.15 Å(2theta=41.93°), $d3$=1.52 Å(2theta=60.8°)

In addition to the reactivity toward paraffins, and the capability of regeneration via air, the active oxygen content, or oxygen capacity, is another important parameter in selecting the metal oxides (e.g., $A_a(M1)_x(M2)_{y-x}(M3)_zO_{y+3/2z}$ (I)). The oxygen capacity is calculated using the following (using $MOz$ and $MO(z-1)$ to represent the first metal oxide and the second metal oxide, respectively):

$$\text{Oxygen Capacity} = \frac{\text{Oxygen wt\% in } MOz \text{ per mole of metal} - \text{Oxygen wt\% in } MO(z-1) \text{ per mole of metal}}{\text{O wt\% in } MOz \text{ per mole of metal}}$$

In at least one embodiment, the oxygen capacity of metal oxide(s) (e.g., $A_a(M1)_x(M2)_{y-x}(M3)_zO_{y+3/2z}$ (I)) is from about 0.5 wt % to about 50 wt %, based on the weight of the metal oxide, such as from about 2 wt % to about 45 wt %, such as from about 3 wt % to about 35 wt %, such as from about 10 wt % to about 35 wt %, such as from about 15 wt % to about 35 wt %, such as from about 20 wt % to about 30 wt %, such as from about 20 wt % to about 28 wt %, alternatively from about 8 wt % to about 18 wt %, such as from about 10 wt % to about 16 wt %.

Optional Support Materials for Dehydrogenation Metal Oxides

In embodiments herein, the oxygen carrying system may include an inert support material. The supported material can be a porous support material, for example, talc, and inorganic oxides. Suitable supports are non-acidic oxides including silica, theta-alumina, zirconia, titania, ceria, non-acidic clays, or basic oxides (such as magnesia, hydrotalcites, or lanthanum oxide). Other support materials may include zeolites, organoclays, or another organic or inorganic support material, or mixtures thereof.

The support material can be an inorganic oxide in a finely divided form. Suitable inorganic oxide materials for use in oxygen carrying systems herein include groups 2, 4, 10, 11, 12, 13, and 14 metal oxides, such as silica, alumina, MgO, $TiO_2$, $ZrO_2$, rare-earth oxides (e.g., $La_2O_3$, $CeO_2$), and mixtures thereof. Other inorganic oxides that may be employed either alone or in combination with the silica, or alumina, are magnesia, titania, zirconia. Suitable supports may include magnesia, titania, zirconia, montmorillonite, phyllosilicate, zeolites, talc, clays. Also, combinations of these support materials may be used, for example, silica-chromium, silica-alumina, silica-titania. Support materials include $Al_2O_3$, $ZrO_2$, $SiO_2$, and combinations thereof, such as $SiO_2$, $Al_2O_3$, or $SiO_2/Al_2O_3$.

The support material should be dry, that is, free of absorbed water. Drying of the support material can be effected by heating or calcining at about 100° C. to about 1,000° C., such as at least about 600° C. When the support material is silica, it is heated to at least 200° C., such as about 200° C. to about 850° C., such as at about 600° C.; and or for a time of about 1 minute to about 100 hours, from about 12 hours to about 72 hours, or from about 24 hours to about 60 hours. The calcined support material must have at least some reactive hydroxyl (OH) groups to produce supported metal oxide systems of the present disclosure. The calcined support material is then contacted with at least one metal oxide (e.g., $A_a(M1)_x(M2)_{y-x}(M3)_zO_{y+3/2z}$ (I)).

The support material, having reactive surface groups, such as hydroxyl groups, can be slurried in a non-polar solvent and the resulting slurry can be contacted with a solution of a metal oxide(s). In at least one embodiment, the slurry of the support material is first contacted with a metal oxide, such as $A_a(M1)_x(M2)_{y-x}(M3)_zO_{y+3/2z}$ (I)) metal oxides, for a period of time in the range of from about 0.5 hours to about 24 hours, from about 2 hours to about 16 hours, or from about 4 hours to about 8 hours.

One or more metal oxide(s) (e.g., $A_a(M1)_x(M2)_{y-x}(M3)_zO_{y+3/2z}$ (I)) and support can be heated to about 0° C. to about 70° C., such as about 23° C. to about 60° C., such as at room temperature. Contact times may range from about 0.5 hours to about 24 hours, from about 2 hours to about 16 hours, or from about 4 hours to about 8 hours.

Suitable non-polar solvents can be materials in which all of the reactants used herein, e.g., the first metal oxide and the second metal oxide are at least partially soluble and which are liquid at reaction temperatures. Non-polar solvents can be alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Dehydrogenation Products

The present disclosure relates to compositions of matter produced by the methods described herein. Furthermore, commercially valuable products such as ethylene and propylene can be formed using processes of the present disclosure.

In at least one embodiment, a process described herein produces $C_2$-$C_{50}$ acyclic olefins of Formula (III) (such as propene, butene, pentene, hexene, heptene, octene, etc., and any isomers thereof), and $C_3$-$C_{50}$ cyclic olefins of Formula (IV) (such as cyclopentene, methyl-cyclopentene, cyclohexene, cycloheptene, cyclooctene, norbornene, etc., and any isomers thereof).

In at least one embodiment, an acyclic olefin is represented by formula (III):

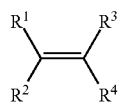

(III)

wherein:
$R^1$, $R^2$, $R^3$, and $R^4$ are independently hydrogen, $C_1$-$C_{40}$ hydrocarbyl (e.g., $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), $C_1$-$C_{40}$ substituted hydrocarbyl (e.g., substituted $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), a heteroatom or a heteroatom-containing group, such as each of $R^1$, $R^2$, $R^3$, and $R^4$ is independently selected from hydrogen, methyl, ethyl, propyl, butyl, pentyl, hexyl, heptyl, octyl, nonyl, decyl, undecyl, dodecyl, phenyl, substituted phenyl, biphenyl or an isomer thereof, which may be halogenated (such as bromopropyl, bromopropyl, bromobutyl, (bromomethyl)cyclopropyl, chloroethyl, 2,3,5,6-tetrafluorobenzyl, perfluoropropyl, perfluorobutyl, perfluoroethyl, perfluoromethyl), substituted hydrocarbyl radicals and isomers of substituted hydrocarbyl radicals such as trimethylsilylpropyl, trimethylsilylmethyl, trimethylsilylethyl, phenyl, or isomers of hydrocarbyl substituted phenyl such as methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, and dipropylmethylphenyle.

In at least one embodiment, $R^2$ and $R^3$ are independently hydrogen or $C_1$-$C_{40}$ hydrocarbyl (e.g., $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), such as methyl, ethyl, propyl, butyl, pentyl, hexyl, heptyl, octyl, nonyl, decyl, undecyl, dodecyl, phenyl, substituted phenyl, biphenyl or an isomer thereof, such as perfluoropropyl-, perfluorobutyl-, perfluoroethyl-, or perfluoromethyl-substituted hydrocarbyl radicals and isomers of substituted hydrocarbyl radicals such as trimethylsilylpropyl, trimethylsilylmethyl, trimethylsilylethyl, or phenyl, and isomers of hydrocarbyl substituted phenyl such as methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, and dipropylmethylphenyl; and $R^1$ and $R^4$ are independently selected from hydrogen, methyl, ethyl, propyl, butyl, pentyl, hexyl, heptyl, octyl, nonyl, decyl, undecyl, dodecyl, phenyl, substituted phenyl, biphenyl or an isomer thereof, which may be halogenated (such as bromopropyl, bromopropyl, bromobutyl, (bromomethyl)cyclopropyl, chloroethyl, 2,3,5,6-tetrafluorobenzyl, perfluoropropyl, perfluorobutyl, perfluoroethyl, perfluoromethyl), substituted hydrocarbyl radicals and isomers of substituted hydrocarbyl radicals such as trimethylsilylpropyl, trimethylsilylmethyl, trimethylsilylethyl, phenyl, or isomers of hydrocarbyl substituted phenyl such as methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, and dipropylmethylphenyl.

In at least one embodiment, $R^2$ and $R^3$ are hydrogen and $R^1$ and $R^4$ are independently selected from hydrogen, methyl, ethyl, propyl, butyl, pentyl, hexyl, heptyl, octyl, nonyl, decyl, undecyl, dodecyl, phenyl, substituted phenyl, biphenyl or an isomer thereof, which may include oxygen, nitrogen, and or sulfur (such as methoxypropyl, methoxybutyl, methoxypentyl methoxyhexyl, methoxyheptyl, methoxyoctyl, methoxydodecyl, ethoxyethyl, ethoxypropyl, ethoxybutyl, ethoxypentyl ethoxyhexyl, ethoxyheptyl, ethoxyoctyl, ethoxyldecyl, ethoxydodecyl, ethoxyphenyl, 1-aminoalkyl (e.g., 1-aminobutyl), 2-aminoalkyl (e.g., 2-aminopentyl), 1-alkylaminoalkyl (e.g., 1-methylaminopropyl), dialkylaminoalkyl (e.g., dimethylaminoethyl) or isomers of hydrocarbyl substituted phenyl such as methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, and dipropylmethylphenyl.

For example, the acyclic olefin represented by formula (III) can be a vinylenes, such as an olefin with a "cis-" conformation, such as an olefin with "trans-" conformation, or a mixture thereof, thus at any proportion thereof. Furthermore, the acyclic olefin can be a tri-substituted vinylene. Traces of tetra-substituted vinylene may be present in the reaction mixture.

In at least one embodiment, a cyclic olefin compound is represented by formula (IV):

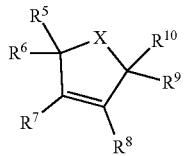

wherein:
X is a one-atom to five-atom linkage (with a "one-atom" linkage referring to a linkage that provides a single, optionally substituted atom between the two adjacent carbon atoms, and a "five-atom" linkage, similarly, referring to a linkage that provides five optionally substituted atoms between the two adjacent carbon atoms); In at least one embodiment, and when the cyclic olefin is bicyclic (e.g., when $R^5$ and $R^{10}$ are linked), then X is a one-atom or two-atom linkage, such as a linkage that has one or two optionally substituted atoms between the two carbon atoms to which X is bound. For example, X can be of the formula —$CR^{11}R^{12}$ (X1)q- wherein q is zero or 1, X1 is $CR^{13}R^{14}$, O, S, or $NR^{15}$, and $R^{11}$, $R^{12}$, $R^{13}$, $R^{14}$ and $R^{15}$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl); When q is 1, suitable examples of linkages can be wherein X1 is $CR^{13}R^{14}$, thus providing a substituted or unsubstituted ethylene moiety to the cyclic olefin of Formula (IV). Accordingly, when $R^{11}$, $R^{12}$, $R^{13}$, and $R^{14}$ are hydrogen, then X is ethylene. When q is zero, the linkage can be substituted or unsubstituted methylene, and a suitable linkage within this group can be methylene (e.g., when $R^{11}$ and $R^{12}$ are both hydrogen);
At least one of $R^7$ and $R^8$ is hydrogen and the other is selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl), or substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl); and
$R^5$, $R^6$, $R^9$, and $R^{10}$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl). Additionally, any two or more of $R^5$, $R^6$, $R^9$, and $R^{10}$ can be taken together to form a cyclic group, which may be, for example, five- or six-membered rings, or two or three five- or six-membered rings, which may be either fused or linked. The cyclic groups may be aliphatic or aromatic, and may be heteroatom-containing and or substituted.

One group of such cyclic olefins are those of formula (IV) wherein $R^6$ and $R^{10}$ are hydrogen, $R^5$ is and $R^9$ combine to form a cyclic ring. In such embodiments, the cyclic olefin is represented by Formula (V):

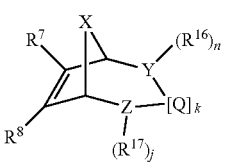

wherein:
X is a one-atom to five-atom linkage. In at least one embodiment, and when the cyclic olefin is bicyclic (e.g., when $R^5$ and $R^{10}$ are linked), then Xis a one-atom or two-atom linkage, such as a linkage that has one or two optionally substituted atoms between the two carbon atoms to which X is bound. For example, X can be of the formula —$CR^{11}R^{12}$—(X1)q- wherein q is zero or 1, X1 is $CR^{13}R^{14}$, O, S, or $NR^{15}$, and $R^{11}$, $R^{12}$, $R^{13}$, $R^{14}$, and $R^{15}$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl); When q is 1, suitable examples of linkages can be wherein X1 is $CR^{13}R^{14}$, thus providing a substituted or unsubstituted ethylene moiety to the cyclic olefin of Formula (V). Accordingly, when $R^{11}$, $R^{12}$, $R^{13}$, and $R^{14}$ are hydrogen, then X is ethylene. When q is zero, the linkage can be substituted or unsubstituted methylene, and a suitable linkage within this group can be methylene (e.g., when $R^{11}$ and $R^{12}$ are both hydrogen);
At least one of $R^7$ and $R^8$ is hydrogen and the other is selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl), or substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl);
Y and Z are independently N, O, or S;
k is zero or 1;
j and n are independently zero or 1;

Q is a one-atom to five-atom linkage. In at least one embodiment, and when the cyclic olefin is bicyclic (e.g., when $R^{16}$ and $R^{17}$ are linked), then Q is a one-atom or two-atom linkage, such as a linkage that has one or two optionally substituted atoms between the two carbon atoms to which Q is bound. For example, Q can be of the formula —$CR^{11'}R12'$-(Q1)q'— wherein q' is zero or 1, Q1 is $CR^{13'}$, $R^{14'}$, O, S, or $NR^{15'}$, and $R^{11'}$, $R^{12'}$, $R^{13'}$, $R^{14'}$, and $R^{15'}$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl); When q' is 1, suitable examples of linkages can be wherein Q1 is $CR^{13'}R^{14'}$, thus providing a substituted or unsubstituted ethylene moiety to the cyclic olefin of Formula (V). Accordingly, when $R^{11'}$, $R^{12'}$, $R^{13'}$, and $R^{14'}$ are hydrogen, then Q is ethylene. When q' is zero, the linkage can be substituted or unsubstituted methylene, and a suitable linkage within this group can be methylene (e.g., when $R^{11'}$ and $R^{12'}$ are both hydrogen);

$R^{16}$ and $R^{17}$ are independently selected from hydrogen, hydrocarbyl, substituted hydrocarbyl, heteroatom-containing hydrocarbyl, substituted heteroatom-containing hydrocarbyl, and amino groups, wherein $R^{16}$ and $R^{'7}$ may be taken together to form a cyclic group;

when Y is 0 or S, then n is zero;
when Z is 0 or S, then j is zero;
when Y is N, then n is 1; and
when Z is N, then j is 1.

In an alternate embodiment, $R^6$ and $R^9$ of formula (V) are hydrogen, in which case the cyclic olefin is represented by formula (VI):

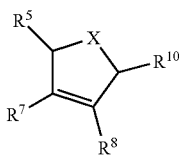

(VI)

wherein:

X is a one-atom to five-atom linkage. In at least one embodiment, and when the cyclic olefin is bicyclic (e.g., when $R^5$ and $R^{10}$ are linked), then X is a one-atom or two-atom linkage, such as a linkage that has one or two optionally substituted atoms between the two carbon atoms to which X is bound. For example, X can be of the formula —$CR^{11}R^{12}$—(X1)q- wherein q is zero or 1, X1 is $CR^{13}R^{14}$, O, S, or $NR^{15}$, and $R^{11}$, $R^{12}$, $R^{13}$, $R^{14}$, and $R^{15}$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, $C_6$-$C_{24}$ aralkyl, $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl). When q is 1, suitable examples of linkages can be wherein X1 is $CR^{13}R^{14}$, thus providing a substituted or unsubstituted ethylene moiety. Accordingly, when $R^{11}$, $R^{12}$, $R^{13}$, and $R^{14}$ are hydrogen, then X is ethylene. When q is zero, the linkage can be substituted or unsubstituted methylene, and a suitable linkage within this group can be methylene (e.g., when $R^{11}$ and $R^{12}$ are both hydrogen).

In at least one embodiment, one of $R^7$ and $R^8$ is hydrogen and the other is selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl), or substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{20}$ aryl, $C_6$-$C_{24}$ alkaryl, and $C_6$-$C_{24}$ aralkyl).

In at least one embodiment, $R^5$, $R^6$, $R^9$, and $R^{10}$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$heteroaryl, heteroatom-containing $C_5$-$C_{30}$ aralkyl, or heteroatom-containing $C_5$-$C_{30}$ alkaryl), substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl). Additionally, two or more of $R^5$, $R^6$, $R^9$, and $R^{10}$ can be taken together to form a cyclic group, which may be, for example, five- or six-membered rings, or two or three five- or six-membered rings, which may be either fused or linked. The cyclic groups may be aliphatic or aromatic, and may be heteroatom-containing and or substituted.

The $C_2$ to $C_{50}$ cyclic olefins may be strained or unstrained, monocyclic or polycyclic, and may optionally include heteroatoms and or one or more functional groups. Exemplary monocyclic olefins represented by Formula (IV) (e.g., olefins wherein $R^5$ and $R^{10}$ are not linked) may include, but are not limited to, cyclopentene, 3-methylcyclopentene, 4-methylcyclopentene, 3-t-butyldimethyl silyloxycyclopentene, 4-t-butyl-dimethyl silyloxycyclopentene, cyclohexene, 3-methylcyclohexene, 4-methyl-cyclohexene, 3-t-butyldimethylsilyloxycyclohexene, 4-t-butyldimethyl silyloxycyclohexene, cycloheptene, 3-methylcycloheptene, 4-methylcycloheptene, 5-methylcycloheptene, 3-t-butyldimethyl silyloxycycloheptene, 4-t-butyldi ethyl silyloxycycloheptene, 5-t-butyldimethylsilyloxycycloheptene, cyclooctene, 3-methylcyclooctene, 4-methylcyclooctene, 5-methylcyclooctene, 3-t-butyldimethyl-silyloxycyclooctene, 4-t-butyldimethylsilyloxycyclooctene, 5-t-butyldimethylsilyloxycyclooctene, cyclononene, 3-methylcyclononene, 4-methylcyclononene, 5-methylcyclononene, 6-methylcyclo-nonene, 3-t-butyldimethyl silyloxycyclononene, 4-t-butyldimethyl silyloxycyclononene, 5-t-butyl-dimethylsilyloxycyclononene, 6-t-butyldimethyl silyloxycyclononene, cyclodecene, 3-methylcyclo-decene, 4-methylcyclodecene, 5-methylcyclodecene, 6-methylcyclodecene, 3-t-butyldimethylsilyloxycyclodecene, 4-t-butyldimethylsilyloxycyclononene, 5-t-butyldimethylsilyloxycyclodecene, 6-t-butyldimethylsilyloxycyclodecene, cycloundecene, 3-methylcycloundecene, 4-methylcycloundecene, 5-methylcycloundecene, 6-methylcycloundecene, 7-methylcycloundecene, 3-t-butyldimethylsilyloxycycloundecene, 4-t-butyldimethylsilyloxycycloundecene, 5-t-butyldimethylsilyloxy-cycloundecene, 6-t-butyldimethylsilyloxycycloundecene, 7-t-butyldimethylsilyloxycycloundecene, cyclododecene, 3-methylcyclododecene, 4-methylcyclododecene, 5-methylcyclododecene, 6-methyl-cyclododecene, 7-methylcyclododecene, 3-t-butyldimethylsilyloxycyclododecene, 4-t-butyldimethylsilyloxycyclododecene, 5-t-butyldimethylsilyloxycyclododecene, 6-t-butyldimethylsilyloxycyclododecene, and 7-t-butyldimethylsilyloxycyclododecene.

Non-limiting examples of cyclic olefins and di-olefins may include cyclopropene, cyclobutene, cyclopentene, cyclohexene, cycloheptene, cyclooctene, cyclononene, cyclodecene, norbornene, 4-methylnorbornene, 7-oxanorbornene, 2-methylcyclopentene, 4-methylcyclopentene, vinylcyclohexane, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

For example, the cyclic olefin represented by formulae (IV), (V), and (VI) can be a vinylenes, such as an olefin with a "cis-" conformation, such as an olefin with "trans-" conformation, or a mixture thereof, thus at any proportion thereof. Furthermore, the cyclic olefin can be a tri-substituted vinylene. Traces of tetra-substituted vinylene may be present in the reaction mixture.

The $C_2$-$C_{50}$ acyclic olefins of Formula (III) (such as $C_2$-$C_{20}$ acyclic olefins, such as $C_9$-$C_{11}$ acyclic olefins) can be produced with a weight average molecular weight (Mw) of from about 28 g/mol to about 700 g/mol, such as from about 28 g/mol to about 420 g/mol, such as from about 28 g/mol to about 280 g/mol. The $C_3$-$C_{50}$ cyclic olefins of Formula (III) can be produced with a weight average molecular weight (Mw) of from about 40 g/mol to about 698 g/mol, such as from about 40 g/mol to about 418 g/mol, such as from about 40 g/mol to about 278 g/mol.

Selective conversion of alkanes, such as cyclic alkane (e.g., cyclo-paraffins) to mono-olefins, such as cyclic olefins, is very rare, since the cyclic olefins typically tend to further convert to the most thermodynamically stable products, which are aromatic products (e.g., benzene). Conventionally, catalysts oxidize cyclohexane all the way to benzene, for example, since benzene is the most thermodynamically stable product. Selectivity can be defined as moles of mono-olefins divided by moles of the total products formed. In at least one embodiment, metal oxides (I) and or (II) used in processes of the present disclosure have a selectivity for mono-olefins (e.g., cyclic olefins such as cyclohexene) of 50% or greater, such as about 50% to about 100%, such as about 55% to about 99.5%, such as from about 70% to about 95%.

LISTING OF EMBODIMENTS

Accordingly, this disclosure provides the following non-limiting embodiments:

Embodiment 1. An active material, comprising:
a mixed metal oxide of the formula:

$$A_a(M1)_x(M2)_{y-x}(M3)_zO_{y+3/2z} \quad (I)$$

wherein:
A is an alkali metal;
M1 is a divalent metal;
M2 is a divalent metal;
M3 is a trivalent metal;
a is $0.01 \le a \le 4$;
x is $0.01 \le x \le 4$;
y is an integer from $2 \le y \le 4$;
z is $0.25y \le z \le 0.5y$; and
the ratio a/x is from 0.1 to 1.0;
and an optional support material.

Embodiment 2. The active material according to embodiment 1, wherein A is selected from the group consisting of Na, Li, K, Rb, and Cs; preferably Na.

Embodiment 3. The active material according to any one of the above embodiments, wherein M1 is selected from the group consisting of Mn, Fe, Co, Ni, and Cu; preferably Cu.

Embodiment 4. The active material according to any one of the above embodiments, M2 is selected from the group consisting of Mg, Ca, Sr, Ba, Zn, Co, Cu, Ni, and Fe; preferably Mg, Co, or Ni; more preferably Mg.

Embodiment 5. The active material according to any one of the above embodiments, wherein M3 is selected from the group consisting of Ga, Fe, Co, Mn, Cr, and Al, preferably Al.

Embodiment 6. The active material according to any one of the above embodiments, wherein z is chosen to satisfy charge neutralization.

Embodiment 7. The active material according to any one of the above embodiments, wherein the active material has a structure having X-Ray diffraction peaks at d-spacing corresponding to three characteristic features of an M2O rocksalt phase, d1, d2 and d3,
wherein the three characteristic d-spacing are:

2.41 Å<$d1$<2.49 Å, 2.09 Å<$d2$<2.15 Å, 1.48 Å<$d3$<1.52 Å;

And wherein the structure is substantially free of X-Ray diffraction peaks at d-spacing corresponding to an M1O phase.

Embodiment 8. The active material according to any one of the above embodiments, having the formula:
$Cu_xMg_{3-x}AlO_{4.5}$, comprising Na, Cs, K, Li, or mixtures thereof;
where x is $0.01 \le x \le 3$.

Embodiment 9. The active material according to any one of the above embodiments, wherein the support material is a non-acidic oxide, a non-acidic clay, a basic oxide, a zeolite, an organo clay, or a combination thereof, preferably the support material is selected from zeolites, organoclays, $Al_2O_3$, $ZrO_2$, $SiO_2$, $SiO_2/Al_2O_3$, $SiO_2/TiO_2$, silica clay, silicon oxide/clay, or mixtures thereof.

Embodiment 10. A process for upgrading a hydrocarbon feed, comprising:
introducing at a temperature of from about 50° C. to about 500° C. a hydrocarbon feed comprising paraffins and introducing an oxidizing agent to an active material according to any one of embodiments 1 to 9;
obtaining a product mixture comprising one or more $C_3$-$C_{50}$ cyclic olefin, one or more $C_2$-$C_{50}$ acyclic olefin, one or more $C_5$-$C_{200}$ hydrocarbon, or a mixture thereof, wherein the product mixture comprises less than 500 ppm $H_2$.

Embodiment 11. The process of according to embodiment 10, wherein the hydrocarbon feed is a naphtha feed comprising one or more $C_3$-$C_{50}$ cyclic alkanes, preferably cyclopropane, cyclobutane, cyclopentane, cyclohexane, cycloheptane, cyclooctane, or mixtures thereof; one or more $C_2$-$C_{50}$ acyclic alkanes, preferably propane, n-butane, iso-butane, n-pentane, iso-pentane, neo-pentane, n-hexane, iso-hexane, neo-hexane, n-heptane, iso-heptane, neo-heptane, n-octane, iso-octane, neo-octane, or mixtures thereof; or a mixture thereof.

Embodiment 12. The process according to embodiment 10 or 11, wherein the hydrocarbon feed comprises one or more $C_3$-$C_{50}$ cyclic alkane and one or more $C_2$-$C_{50}$ acyclic alkane, and a molar ratio of cyclic alkane to acyclic alkane is from about 1:250 to about 250:1, preferably 1:10 to about 10:1.

Embodiment 13. A method of preparing an active material according to any one of embodiments 1 to 9 comprising the steps of:
preparing an aqueous solution of one or more metal oxides or metal nitrates;
adjusting the pH with an alkali component to precipitate a mixed metal oxide; and
aging the mixed metal oxide in to obtain the active material.

Embodiment 14. The method of preparing an active metal material according to embodiment 13, wherein the aqueous solution comprises two or more metal oxides or metal nitrates or a mixture thereof, preferably three or more metal oxides or metal nitrates or a mixture thereof.

Embodiment 15. The method of preparing an active metal material according to any one of embodiments 13 or 14, further comprising a step of:
filtering the mixed metal oxide to provide a wet filtrate after the aging step;
drying the wet filtrate;
aging the wet filtrate in a solution of water, otionally including acetone, an alcohol, or both after a step of filtering the mixed metal oxide to provide a wet filtrate after the aging step;
calcining the mixed metal oxide after the aging step; and/or
calcining the mixed metal oxide after the second aging step.

EXAMPLES

Materials Synthesis and Characterization

Materials Testing

The materials have been tested for n-hexane oxidative dehydrogenation using a tandem micro-reactor (Schematics for the reactor is shown in FIG. 1). The unit has two reactors connected in tandem, sitting on top of a GC/MS instrument. For this application, the first reactor serves as a vaporizer for the liquid feed and the material to be tested is loaded in the second reactor. The effluent from the second reactor is collected via a micro-jet selective sampler that is cryogenically modulated using liquid nitrogen. After a pre-set sampling time, the collected sample is injected to the GC/MS for analysis. For quantitative hydrocarbon analysis, the mass spectrometer is calibrated with known concentrations of authentic samples. Calibration of $CO_2$ on the MS is achieved using a solution of lauroyl peroxide [$C_{13}H_{27}C(O)O$—OC(O)$C_{13}H_{27}$], which is known to thermally decompose and release $CO_2$ quantitatively.

In a typical run, the material to be tested is sized to 20/40 mesh and loaded in the quartz tube (0.2 cc, neat or diluted with quartz chips) located in the second reactor. The material is pre-treated with flowing air at 650° C. for 2 h before reaction to ensure it is in the oxide form, clean off any contamination and drive off residual moisture. After the pre-treatment, the second reactor is set to desired temperature. Liquid n-hexane (0.05 micro-liter) is injected into the first reactor (held at 200° C.), which quickly vaporizes and is carried with helium flow (3 cc/min) through the first reactor. At the exit of the first reactor, this feed stream is further diluted with 50 cc/min helium and fed to the second reactor. The micro-jet sample collection time for the effluent from the second reactor is set at 5 min before it is analyzed by GC/MS. Different conversions for n-hexane are achieved by varying the temperature for the second reactor. When necessary, the material is regenerated in flowing air at 450 C. for 30 min between injections.

There is no $O_2$ co-feed in this testing; and the stoichiometric oxidation is represented below.

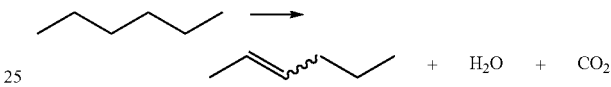

Selectivity is calculated on the carbon base:

Selectivity to hexenes=moles hexenes/[moles of hexenes+(moles of $CO_2$)/6]×100%

Example 1. n-Hexane Oxidative Dehydrogenation Using CuO (Comparative

Figure 2:
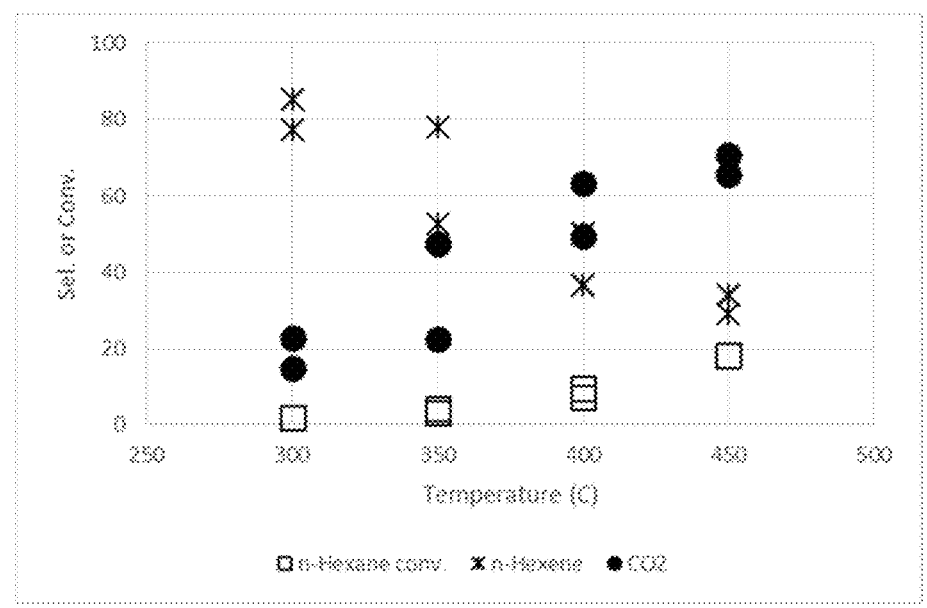
FIG. 2 is a graph depicting n-Hexane conversion and product selectivity for CuO (Example 1). Different data points at each temperature indicate repeated injections.

A commercial sample of CuO (nanopowder, <50 nm particle size) was obtained from Sigma-Aldrich and used as received. Elemental analysis shows the sample contains 0.593 wt % Na. The powder was pressed/sized to 20/40 mesh, diluted with quartz chips (60/80 mesh) (0.1 cc CuO with 0.1 cc quartz) and loaded in the tandem reactor. An amount of 0.05 micro-liter of n-hexane was used for each injection; and the temperature was scanned in the range of 300-450 C. The conversion and selectivity profiles are shown in FIG. 2 (CuO Run 6).

Example 2. n-Hexane Oxidative Dehydrogenation Using CuO/$SiO_2$ (Comparative

Figure 3:
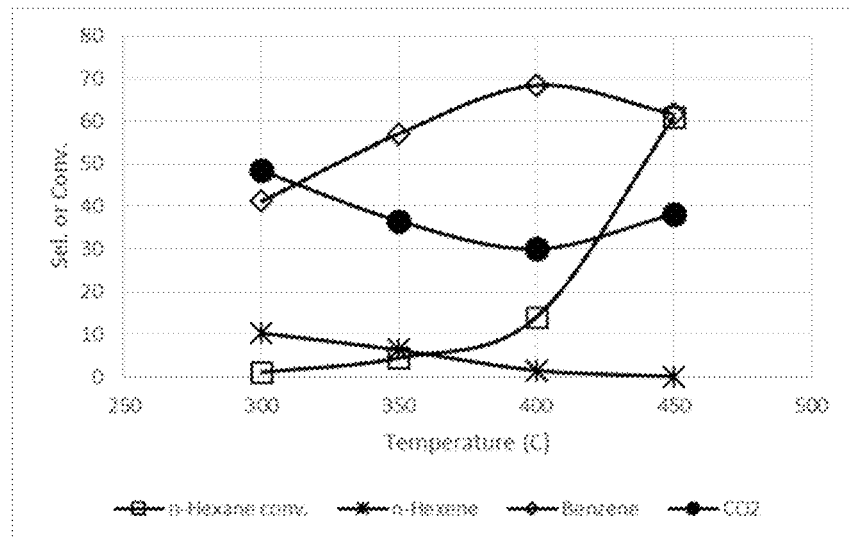
FIG. 3 is a graph depicting n-Hexane conversion and product selectivity for $CuO/SiO_2$ (Example 2)

The material tested in this example is 20 wt % CuO on Davisil 646, prepared via incipient wetness using Cu($NO_3$)$_2$. The conversion and selectivity profiles are shown in FIG. 3.

Example 3. n-Hexane Oxidative Dehydrogenation Using CuO/$Al_2O_3$ (Comparative

Figure 4:
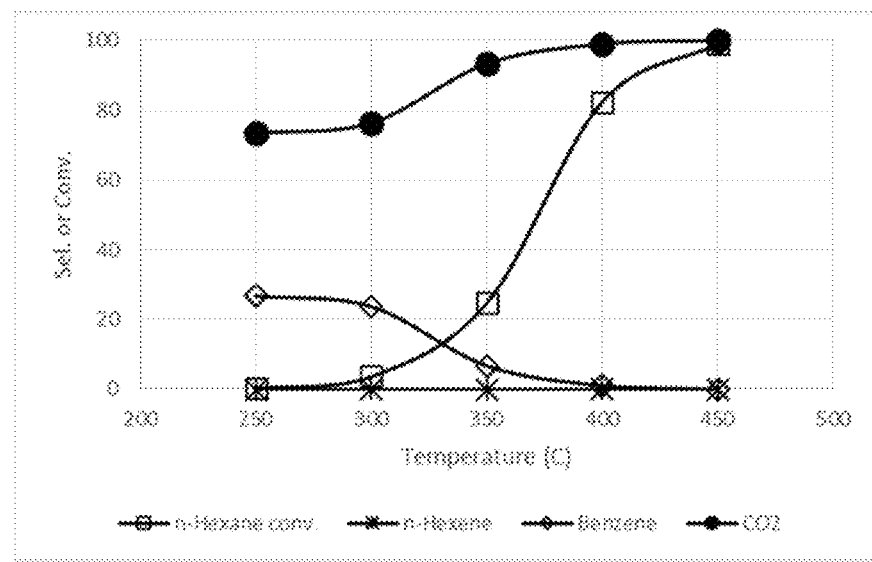
FIG. 4 is a graph depicting n-Hexane conversion and product selectivity for $CuO/Al_2O_3$ (Example 3)

The material tested in this example is 20 wt % CuO on γ-$Al_2O_3$ (Alfa), prepared via incipient wetness using Cu($NO_3$)$_2$. The conversion and selectivity profiles are shown in FIG. 4.

Example 4. n-Heptane Oxidative Dehydrogenation using CuO/MgO (Comparative

Figure 5:
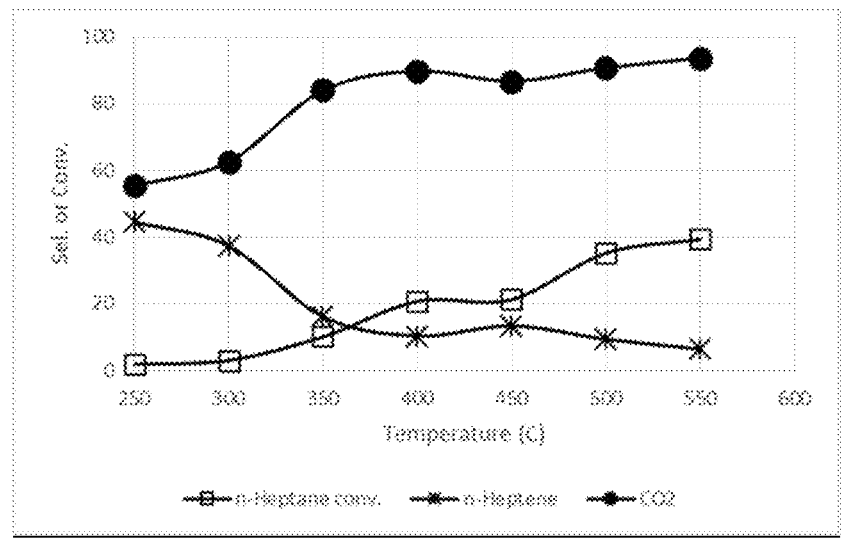
FIG. 5 is a graph depicting n-Heptane conversion and product selectivity for $CuO/Al_2O_3$
(Example 3)

The material tested in this example is 20 wt % CuO on MgO, prepared via incipient wetness using Cu($NO_3$)$_2$. Instead of n-hexane, n-heptane is the feed. The conversion and selectivity profiles are shown in FIG. 5.

Figure 6:
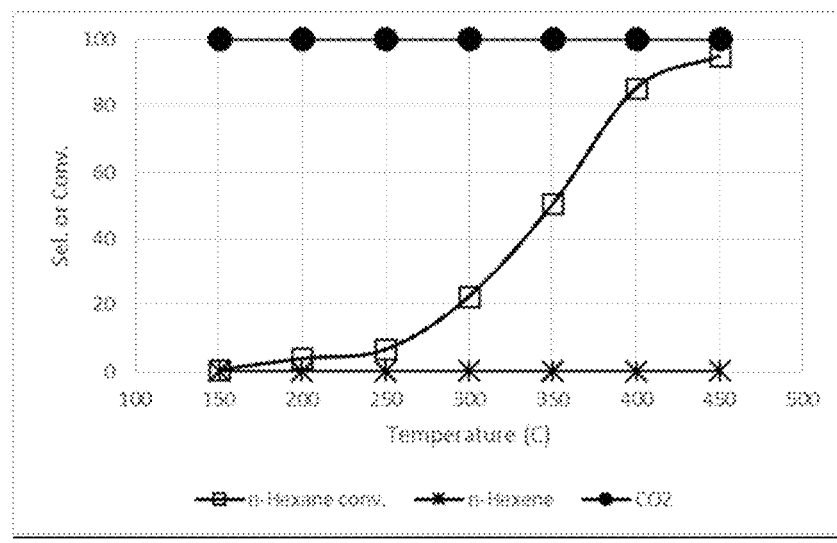
FIG. 6 is a graph depicting n-Hexane conversion and product selectivity for $CuO/TiO_2$ (Example 5)

Example 5. n-Hexane Oxidative Dehydrogenation Using CuO/TiO$_2$ (Comparative The material tested in this example is 6 wt % Cu on TiO$_2$ (P-25), prepared via incipient wetness using Cu(NO$_3$)$_2$. Total combustion of n-hexane is observed on this material, as shown in FIG. 6.

Example 6. n-Hexane Oxidative Dehydrogenation Using Cu$_x$Mg$_{3-x}$AlO$_{4.5}$ [(Mg+Cu)/Al Mole Ratio=3, 15 Mole % Cu] with <0.04 wt % Na (Invention A 100 ml aqueous solution containing 24.62 g Mg(NO$_3$)$_2$.6H$_2$O (0.10 mol), 5.80 g Cu(NO$_3$)$_2$.6H$_2$O (0.025 mol), and 15.00 g Al(NO$_3$)$_3$.9H$_2$O (0.04 mol) was added dropwise to 100 mL aqueous solution containing 5.3 g Na$_2$CO$_3$ (0.05 mol) at room temperature upon stirring. Use 4M NaOH solution to adjust pH to 10.0 before aging at room temperature for 24 hrs. After aging, the slurry became a thick gel and did not settle easily. Filtered and washed with abundant amounts of water and acetone. Never let the material dry during filtration. The wet precipitate was then added to 600 mL ethanol and stirred at room temperature for 4 hrs. Filter and wash with extra ethanol before vacuum drying at room temperature for 18 hrs. Yield 15.3 g fluffy blue powder. Elemental analysis: Mg, 16.0 wt %, Cu, 11.3 wt %, Al, 7.70 wt %, Na<0.045 wt %.

Figure 7:
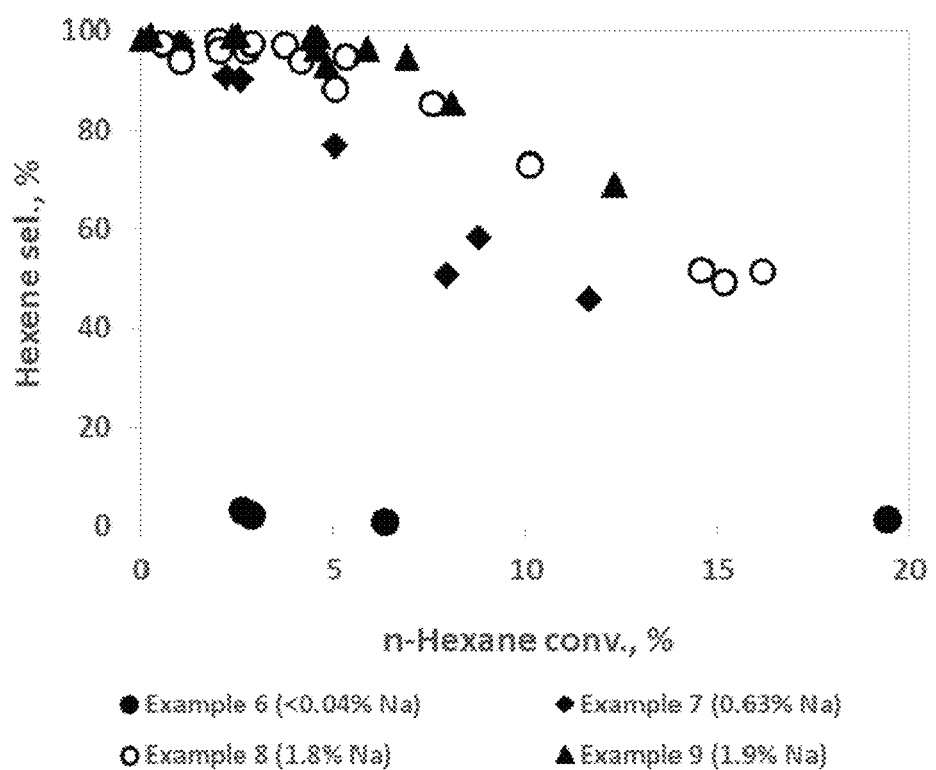
FIG. 7 is a graph depicting n-Hexane conversion and n-hexene selectivity profiles for $Cu_xMg_{3-x}AlO_{4.5}$ (Examples 6-9)
Figure 8:
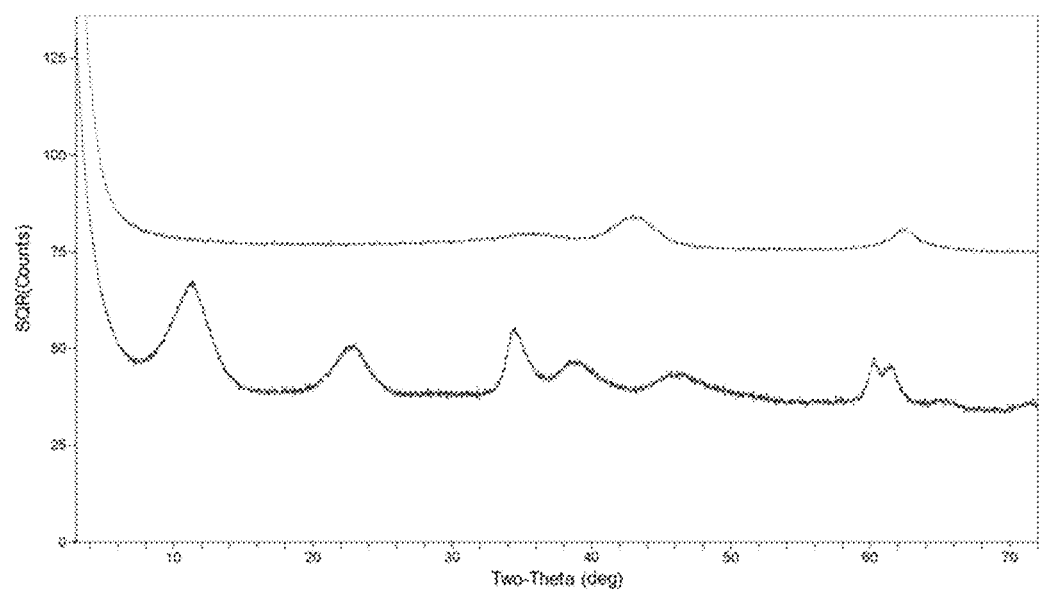
FIG. 8 is an X-Ray Diffractogram (XRD) of Example 6

The as-prepared material (Sample 6) has a BET surface area of 412 m$^2$/g and contains essentially no sodium (<0.04 wt %). It was calcined under static air at 650° C. for 3 h before use. The n-hexene selectivity vs. n-hexane conversion profile is shown in FIG. 7. XRD data is shown in FIG. 8 (bottom, as-synthesized; top, calcined).

Example 7. n-Hexane Oxidative Dehydrogenation Using Cu$_x$Mg$_{3-x}$AlO$_{4.5}$ [(Mg+Cu)/Al Mole Ratio=3, 15 Mole % Cu] with 0.63 wt % Na (Invention A 150 mL aqueous solution containing 30.76 g Mg(NO$_3$)$_2$.6H$_2$O (0.12 mol), 7.24 g Cu(NO$_3$)$_2$.6H$_2$O (0.03 mol), and 18.74 g Al(NO$_3$)$_3$.9H$_2$O (0.05 mol) was added dropwise to 100 mL aqueous solution containing 53.00 g Na$_2$CO$_3$ (0.5 mol) at 60° C. upon stirring. Use 4M NaOH solution to adjust pH to 10.0 before aging at 60° C. for 12 hrs. After aging, the slurry became a thick gel and did not settle easily. 2 L acetone was added to the gel, followed by stirring at room temperature for 14 hrs. Decant all clear supernatant, repeat with 2 L acetone three times. At the end, the resulting precipitate was filtered and washed with acetone and then water, and dried at 60° C. in air for 16 hrs. Yield 58.77 g fluffy blue powder. Elemental analysis: Mg, 16.8 wt %, Cu, 11.5 wt %, Al, 8.02 wt %, Na, 0.638 wt %.

Figure 9:
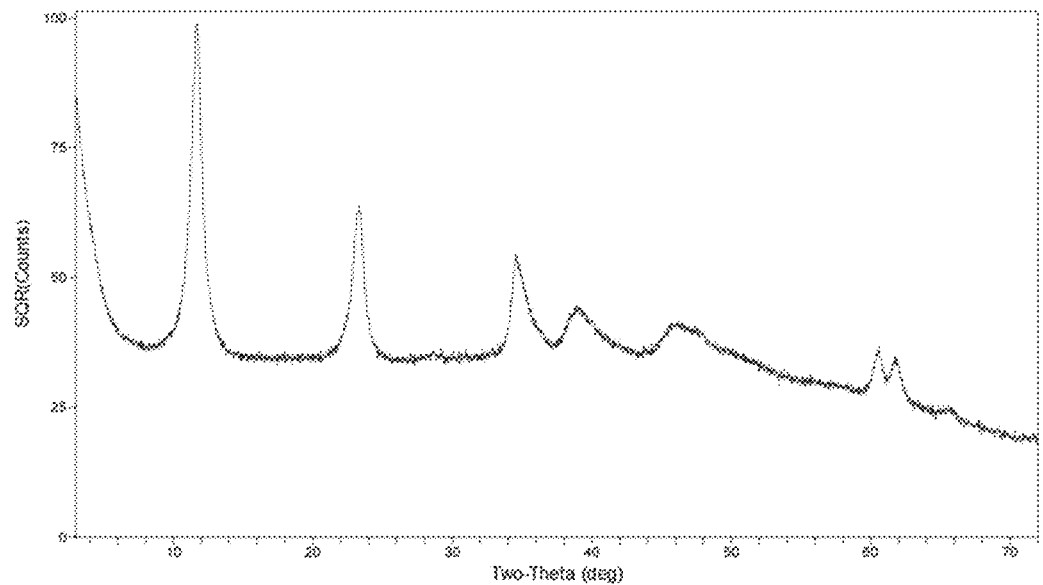
FIG. 9 is an X-Ray Diffractogram (XRD) of Example 7

The as-prepared material (Sample 7) has a BET surface area of 110 m$^2$/g and contains 0.63 wt % of sodium. It was calcined under static air at 650° C. for 3 h before use. The n-hexene selectivity vs. n-hexane conversion profile is shown in FIG. 7. XRD data for the as-synthesized sample is shown in FIG. 9.

Example 8. n-Hexane Oxidative Dehydrogenation Using Cu$_x$Mg$_{3-x}$Al$_{4.5}$ [(Mg+Cu)/Al Mole Ratio=3, 15 Mole % Cu] with 1.8 wt % Na (Invention A 120 mL aqueous solution containing 30.00 g Mg(NO$_3$)$_2$.6H$_2$O (0.12 mol), 7.067 g Cu(NO$_3$)$_2$.6H$_2$O (0.03 mol), and 18.287 g Al(NO$_3$)$_3$.9H$_2$O (0.05 mol) was added dropwise to 120 mL aqueous solution containing 51.67 g Na$_2$CO$_3$ (0.50 mol) at room temperature upon stirring. Use 4M NaOH solution to adjust pH to 10.0 before aging at room temperature for 18 hrs. After aging, the slurry became thick gel and did not settle easily. Filtered and washed with abundant amounts of water and ethanol. Never let the material dry during filtration. The wet precipitate was then added to 600 mL ethanol and stirred at room temperature for 4 hrs. Filter and wash with extra ethanol before vacuum drying at room temperature for 2 days. Yield 22.08 g fluffy blue powder. Chemical Formula is Mg$_{2.4}$Cu$_{0.6}$Al$_1$—HT. Elemental analysis: Mg, 16.2 wt %, Cu, 10.6 wt %, Al, 7.43 wt %, Na, 1.83 wt %.

Figure 10:
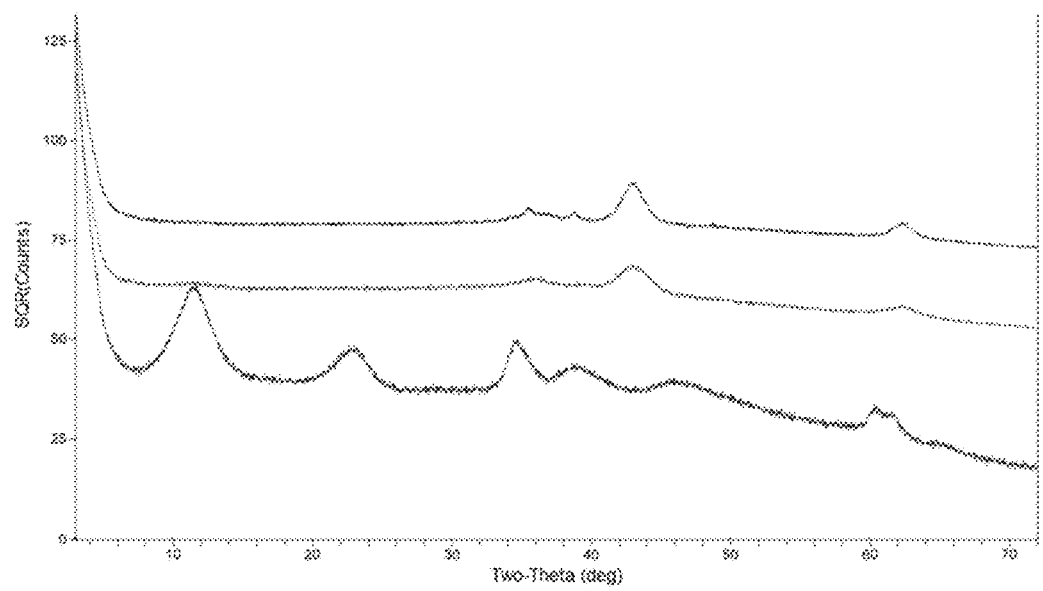
FIG. 10 is an X-Ray Diffractogram (XRD) of Example 8

The as-prepared material (Sample 8) has a BET surface area of 415 m$^2$/g and contains 1.8 wt % of sodium. It was calcined under static air at 650° C. for 3 h before use. The n-hexene selectivity vs. n-hexane conversion profile is shown in FIG. 7. XRD data is shown in FIG. 10 (bottom, as-synthesized; middle, 500° C. calcined; top, 650° C. calcined).

Example 9. n-Hexane Oxidative Dehydorgenation Using Cu$_x$Mg$_{3-x}$Al$_{4.5}$ [(Mg+Cu)/Al Mole Ratio=3, 15 Mole % Cu] with 1.9 wt % Na (Invention A 75 ml aqueous solution containing 15.38 g Mg(NO$_3$)$_2$.6H$_2$O (0.06 mol), 3.62 g Cu(NO$_3$)$_2$.6H$_2$O (0.015 mol), and 9.37 g Al(NO$_3$)$_3$.9H$_2$O (0.025 mol) was added dropwise to 50 mL aqueous solution containing 26.49 g Na$_2$CO$_3$ (0.25 mol) at 60° C. upon stirring. Use 4M NaOH solution to adjust pH to 10.0 before aging at 60° C. for 12 hrs. After aging, the slurry became thick gel and did not settle easily. 2 L water was added to the gel, followed by stirring at room temperature. Decant all clear supernatant, repeat with 2 L water three times. At the end, the resulting wet precipitate was filtered, kept wet, and dispersed into 500 mL acetone, and washed with acetone and dry at 60° C. in air for 3 days. Elemental analysis: Mg, 16.3 wt %, Cu, 11.3 wt %, Al, 7.92 wt %, Na, 1.94 wt %.

Figure 11:
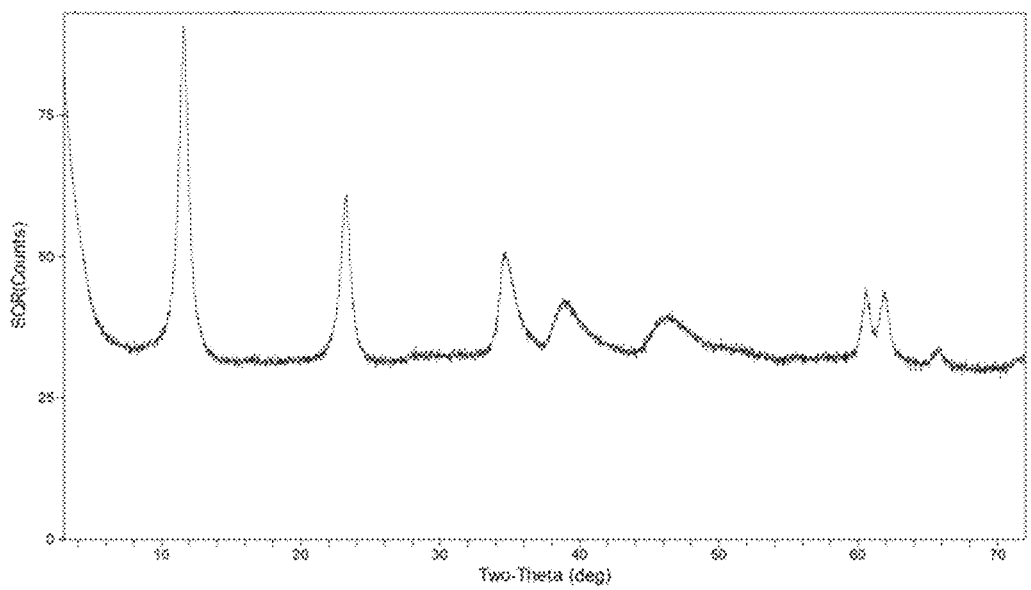
FIG. 11 is an X-Ray Diffractogram (XRD) of Example 9

The as-prepared material (Sample 9) has a BET surface area of 110 m$^2$/g and contains 1.9 wt % of sodium. It was calcined under static air at 650° C. for 3 h before use. The n-hexene selectivity vs. n-hexane conversion profile is shown in FIG. 7. XRD data is shown in FIG. 11.

Example 10. n-Hexane Oxidative Dehydrogenation Using Cu$_x$Mg$_{3-x}$Al$_{4.5}$ [(Mg+Cu)/Al Mole Ratio=3, 15 Mole % Cu] with 0.98 wt % K (Invention The Sample 10 series was made by the following method. A 150 mL aqueous solution containing 36.93 g Mg(NO$_3$)$_2$.6H$_2$O (0.15 mol), 8.7 g Cu(NO$_3$)$_2$.6H$_2$O (0.037 mol), and 22.50 g Al(NO$_3$)$_3$.9H$_2$O (0.06 mol) was added dropwise to 150 ml aqueous solution containing 7.9 g Na$_2$CO$_3$ (0.075 mol) at room temperature upon stirring. Use 4M NaOH solution to adjust pH to 10.0 before aging at room temperature for 18 hrs. After aging, the slurry became a thick gel and did not settle easily. Filtered and washed with abundant amount of water and ethanol. Never let the material dry during filtration. The wet precipitate was then added to 600 mL ethanol and stirred at room temperature for 4 hrs. Filter and wash with extra ethanol before vacuum drying at room temperature for 2 days. Yield 20.43 g fluffy blue powder. 26951-156A6 was made by adding 0.0194 g K$_2$CO$_3$ in 2.1 mL deionized water onto 1.937 g 26951-156A, following by calcination at 650° C. for 2 hrs, yielding 1.089 g K modified $Mg_3Al$ HT.

Figure 12:
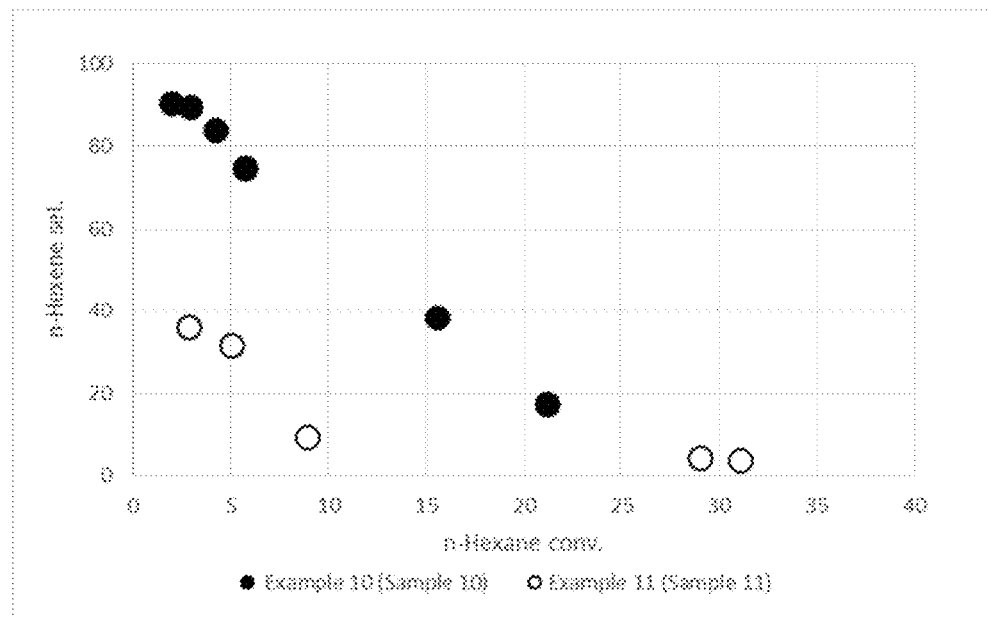
FIG. 12 is a graph depicting n-Hexane conversion and n-hexene selectivity profiles for $Cu_xMg_{3-x}AlO_{4.5}$ (Examples 10-11)
Figure 13:
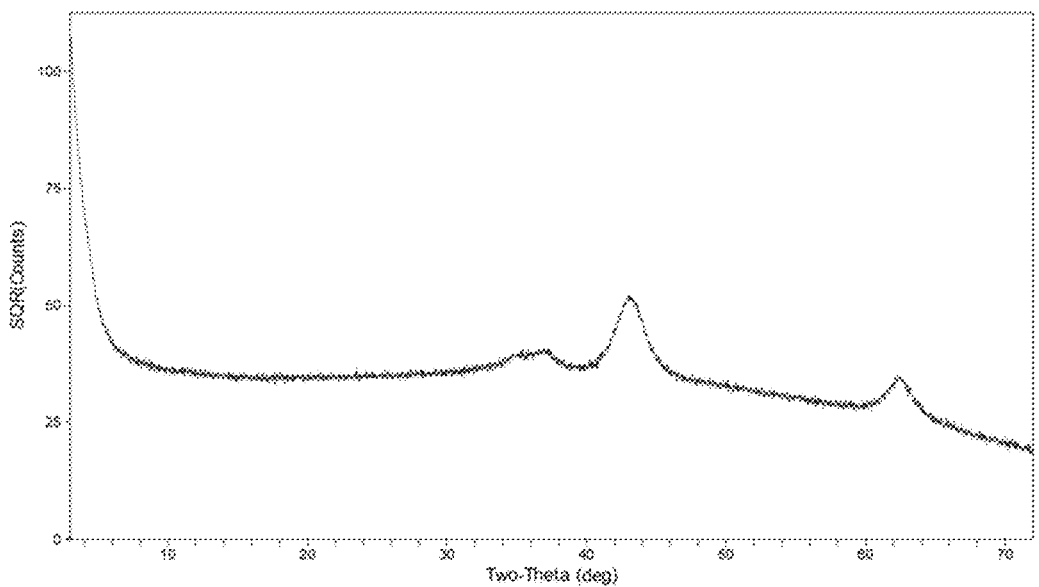
FIG. 13 is an X-Ray Diffractogram (XRD) of Example 10

The as-prepared material (Sample 10) contains 0.98 wt % of potassium. It was calcined under static air at 650° C. for 3 h before use. The n-hexene selectivity vs. n-hexane conversion profile is shown in FIG. 12. XRD data is shown in FIG. 13

Example 11. n-Hexane Oxidative Dehydrogenation Using $Cu_xMg_{3-x}Al_{4.5}$ [(Mg+Cu)/Al Mole Ratio=3, 15 Mole % Cu] with 1.41 wt % Cs (Invention Sample 11 was made by adding 0.0198 g $Cs_2CO_3$ in 2.1 mL deionized water onto 1.985 g 26951-156A, following by calcination at 650° C. for 2 hrs, yielding 1.09 g Cs modified $Mg_3Al$ HT.

Figure 14:
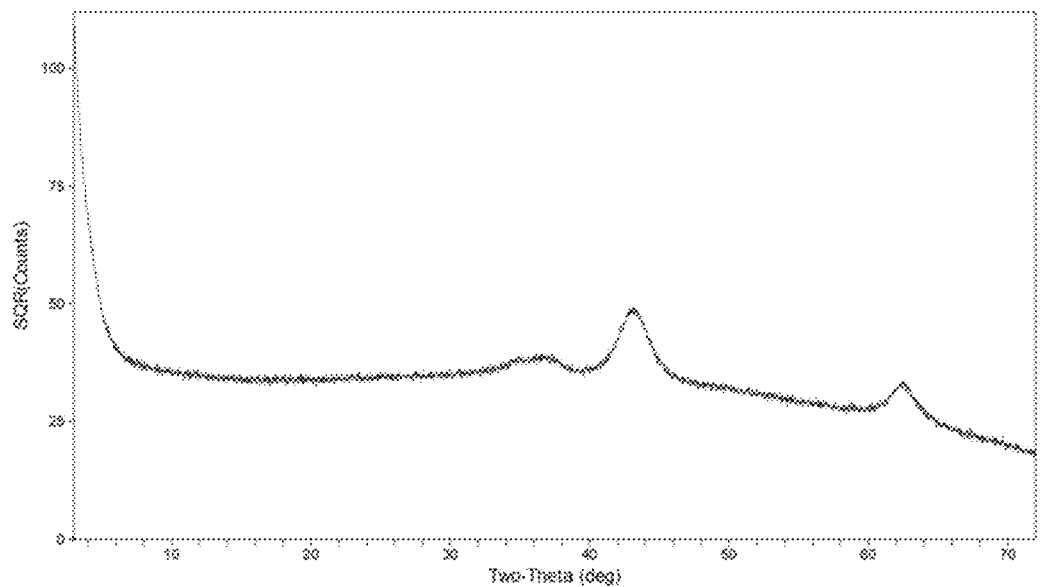
FIG. 14 is an X-Ray Diffractogram (XRD) of Example 11

The as-prepared material (Sample 11) contains 1.41 wt % of cesium. It was calcined under static air at 650° C. for 3 h before use. The n-hexene selectivity vs. n-hexane conversion profile is shown in FIG. 12. XRD data is shown in FIG. 14.

Example 12. n-Hexane Oxidative Dehydrogenation Using $Cu_xMg_{3-x}Al_{4.5}$ [(Mg+Cu)/Al Mole Ratio=2, 13.3 Mole % Cu] with 1.52 wt % Na (Invention A 75 ml aqueous solution containing 9.936 g $Mg(NO_3)_2 \cdot 6H_2O$ (0.040 mol), 2.718 g $Cu(NO_3)_2 \cdot 6H_2O$ (0.0115 mol), and 9.378 g $Al(NO_3)_3 \cdot 9H_2O$ (0.0025 mol) was added dropwise to 75 mL aqueous solution containing 17.22 g $Na_2CO_3$ (0.163 mol) at room temperature upon stirring. Use 4M NaOH solution to adjust pH to 10.0 before aging at room temperature for 18 hrs. After aging, the slurry became a thick gel and did not settle easily. Filtered and washed with abundant amounts of water and ethanol. Never let the material dry during filtration. The wet precipitate was then added to 600 mL ethanol and stirred at room temperature for 4 hrs. Filter and wash with extra ethanol before vacuum drying at room temperature for 2 days. Yield 20.43 g fluffy blue powder. Chemical Formula is $Mg_{1.6}Cu_{0.4}Al_1$-HT. Elemental analysis: Mg, 13.9 wt %, Cu, 11.3 wt %, Al, 9.98 wt %, Na, 1.52 wt %.

Figure 15:
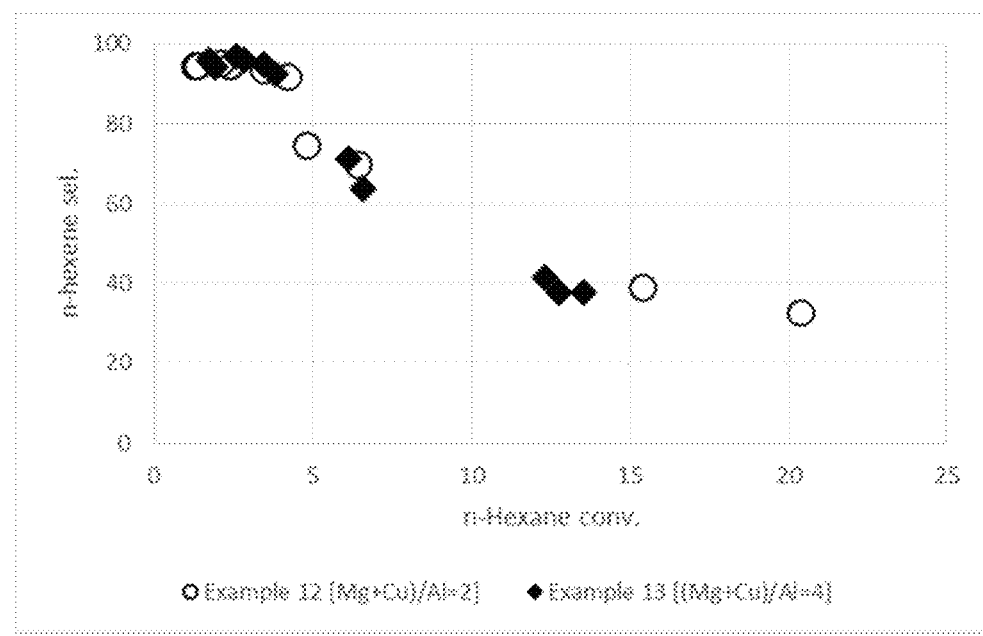
FIG. 15 is a graph n-Hexane conversion and n-hexene selectivity profiles for $Cu_xMg_{3-x}AlO_{4.5}$ (Examples 12-13)
Figure 16:
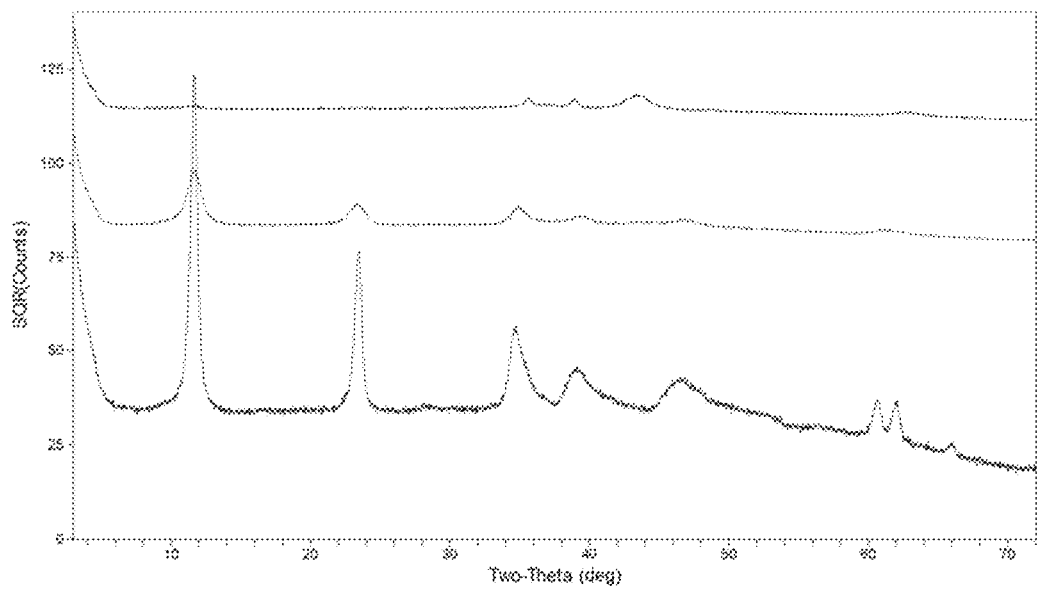
FIG. 16 is an X-Ray Diffractogram (XRD) of Example 12

The as-prepared material (Sample 12) contains 1.52 wt % of sodium. It was calcined under static air at 650° C. for 3 h before use. The n-hexene selectivity vs. n-hexane conversion profile is shown in FIG. 15. XRD data is shown in FIG. 16 (bottom, as-synthesized; middle, 500° C. calcined; top, 650° C. calcined).

Example 13. n-Hexane Oxidative Dehydrogenation Using $Cu_xMg_{3-x}AlO_{4.5}$ [(Mg+Cu)/Al Mole Ratio=4, 16 Mole % Cu] with 2.16 wt % Na (Invention A 75 ml aqueous solution containing 20.00 g $Mg(NO_3)_2 \cdot 6H_2O$ (0.080 mol), 2.718 g $Cu(NO_3)_2 \cdot 6H_2O$ (0.0115 mol), and 9.378 g $Al(NO_3)_3 \cdot 9H_2O$ (0.0025 mol) was added dropwise to 75 mL aqueous solution containing 17.22 g $Na_2CO_3$ (0.163 mol) at room temperature upon stirring. Use 4M NaOH solution to adjust pH to 10.0 before aging at room temperature for 18 hrs. After aging, the slurry became a thick gel and did not settle easily. Filtered and washed with abundant amounts of water and ethanol. Never let the material dry during filtration. The wet precipitate was then added to 600 mL ethanol and stirred at room temperature for 4 hrs. Filter and wash with extra ethanol before vacuum drying at room temperature for 2 days. Chemical Formula is $Mg_{3.2}Cu_{0.8}Al_1$—HT. Elemental analysis: Mg, 16.7 wt %, Cu, 11.8 wt %, Al, 6.73 wt %, Na, 2.16 wt %.

Figure 17:
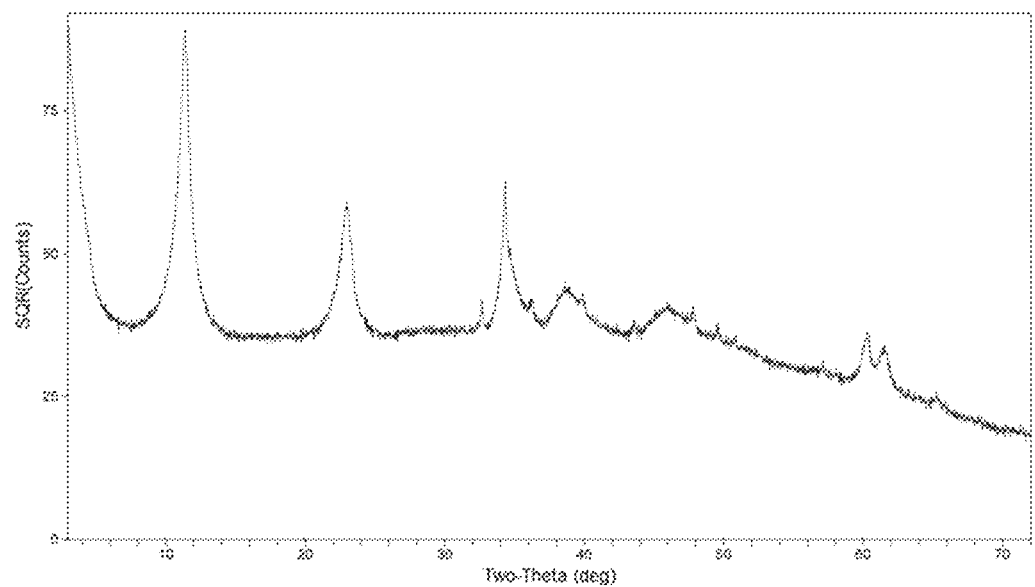
FIG. 17 is an X-Ray Diffractogram (XRD) of Example 13

The as-prepared material (Sample 13) contains 2.16 wt % of sodium. It was calcined under static air at 650° C. for 3 h before use. The n-hexene selectivity vs. n-hexane conversion profile is shown in FIG. 15. XRD data is shown in FIG. 17.

Example 14. Effect of Changing Na Loading (Na to Cu Ratio) and its Corresponding Structure Synthesis detail to Example 14 (Sample 14 series with varying Na content): The Sample 14 series was made by the following method. A 150 mL aqueous solution containing 36.93 g $Mg(NO_3)_2 \cdot 6H_2O$ (0.15 mol), 8.7 g $Cu(NO_3)_2 \cdot 6H_2O$ (0.037 mol), and 22.50 g $Al(NO_3)_3 \cdot 9H_2O$ (0.06 mol) was added dropwise to 150 ml aqueous solution containing 7.9 g $Na_2CO_3$ (0.075 mol) at room temperature upon stirring. Use 4M NaOH solution to adjust pH to 10.0 before aging at room temperature for 18 hrs. After aging, the slurry became a thick gel and did not settle easily. Filtered and washed with abundant amount of water and ethanol. Never let the material dry during filtration. The wet precipitate was then added to 600 mL ethanol and stirred at room temperature for 4 hrs. Filter and wash with extra ethanol before vacuum drying at room temperature for 2 days. Yield 20.43 g fluffy blue powder.

Sample 14-1 was made by adding 0.0099 g $Na_2CO_3$ in 2.1 mL deionized water onto 1.989 g 26951-156A, following by calcination at 650° C. for 4 hrs, yielding 0.05 Na/Cu modified $Mg_3Al$ HT.

Sample 14-2 was made by adding 0.02 g $Na_2CO_3$ in 2.1 mL deionized water onto 1.997 g 26951-156A, following by calcination at 650° C. for 4 hrs, yielding 0.11 Na/Cu modified $Mg_3Al$ HT.

Sample 14-3 was made by adding 0.04 g $Na_2CO_3$ in 2.1 mL deionized water onto 2.000 g 26951-156A, following by calcination at 650° C. for 4 hrs, yielding 0.22 Na/Cu modified $Mg_3Al$ HT.

Sample 14-7 was made by adding 0.08 g $Na_2CO_3$ in 2.1 mL deionized water onto 1.92 g 26951-156A, following by calcination at 650° C. for 4 hrs, yielding 0.44 Na/Cu modified $Mg_3Al$ HT.

Sample 14-8 was made by adding 0.16 g $Na_2CO_3$ in 2.1 mL deionized water onto 1.84 g 26951-156A, following by calcination at 650° C. for 4 hrs, yielding 0.87 Na/Cu modified $Mg_3Al$ HT.

Figure 18:
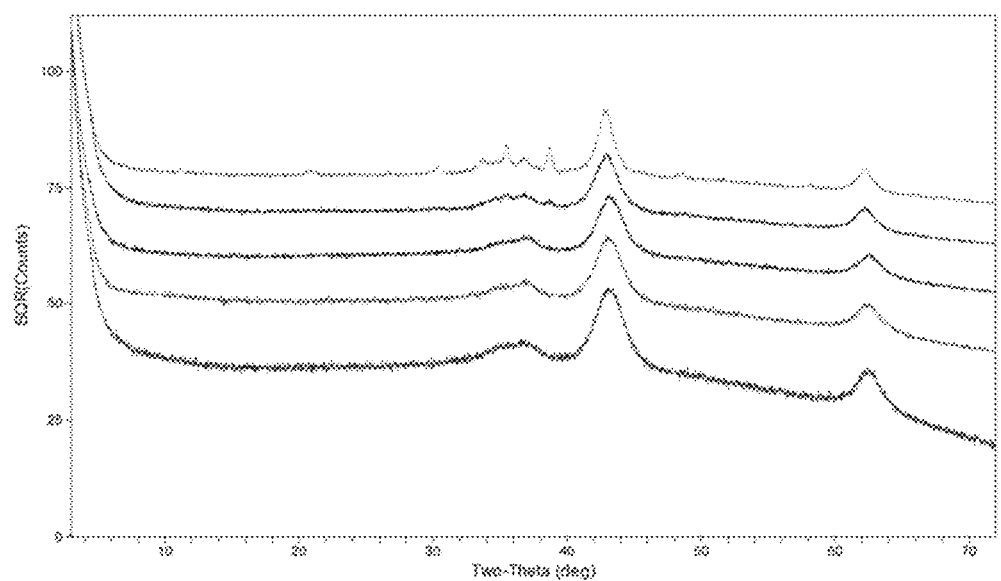
FIG. 18 is an X-Ray Diffractogram (XRD) of Example 14
Figure 19:
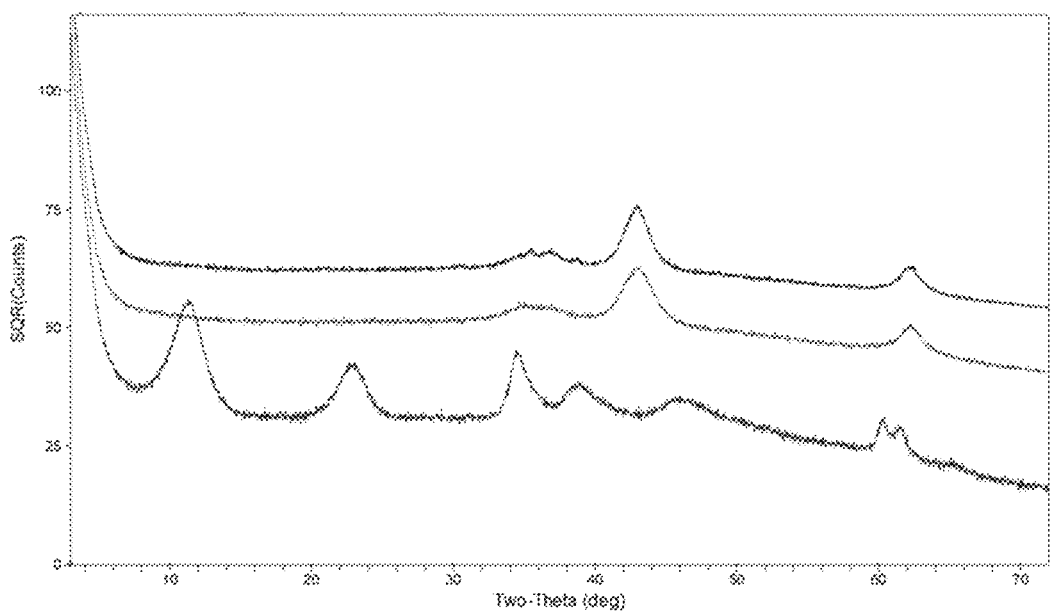
FIG. 19 is an X-Ray Diffractogram (XRD) of Example 14 showing the changes after calcination and Na addition changes.
Figure 20:
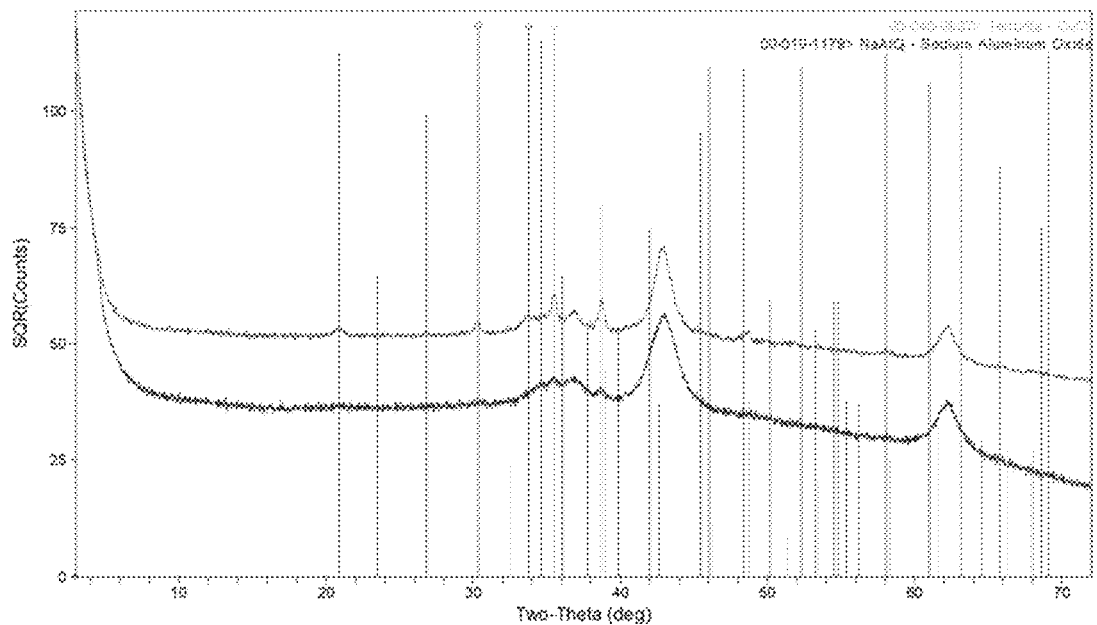
FIG. 20 is an X-Ray Diffractogram (XRD) of Example 14 showing the indexing of impurities.

Corresponding XRD appear in FIGS. 18-20. FIG. 18 from bottom to top: Sample 14-1, 14-2, 14-3, 14-7, and 14-8. FIG. 19: bottom, Sample 14 as-synthesized; middle, Sample 14 calcined at 650° C.; top; Sample 14-7 calcined at 650° C. FIG. 20: bottom, Sample 14-7 calcined at 650° C.; top, Sample 14-8 calcined at 650° C.

Figure 21:
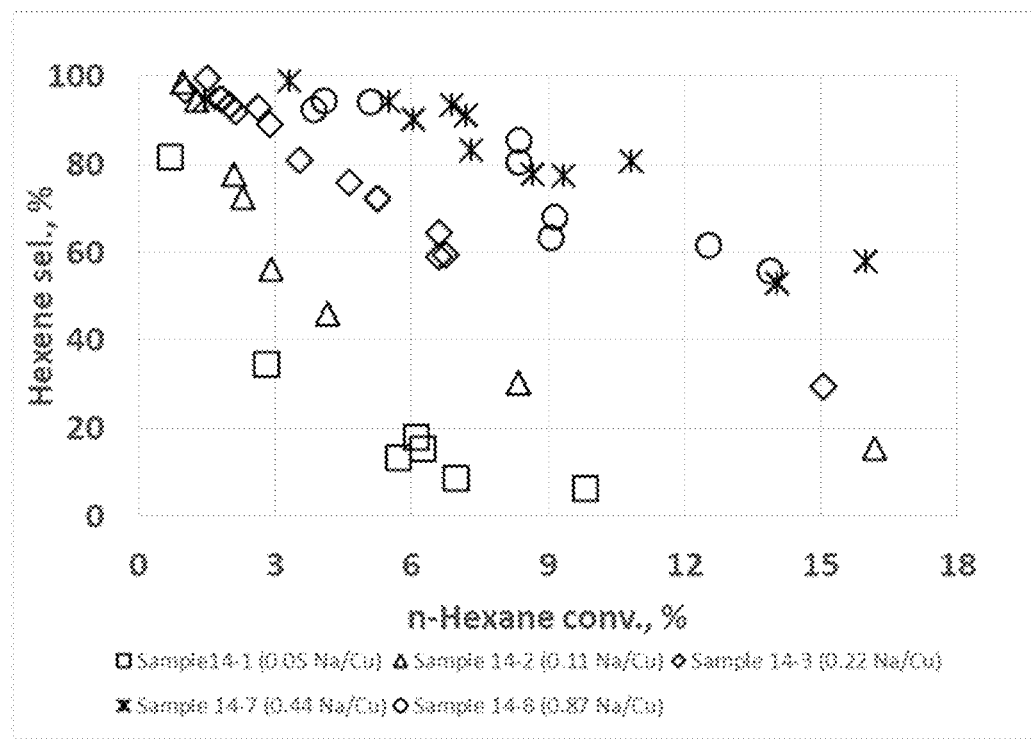
FIG. 21 is a graph depicting n-Hexane conversion and n-hexene selectivity profiles for the 156A series of $Cu_xMg_{3-x}AlO_{4.5}$ (Example 14)

This series of materials contain varying amount of sodium (expressed in the Na/Cu mole ratio). They were calcined under static air at 650° C. for 3 h before use. The n-hexene selectivity vs. n-hexane conversion profile is shown in FIG. 21. Selectivity to hexenes increases with increasing Na/Cu ratio; and the preferred Na/Cu ratio is ~0.4; no additional benefit in selectivity is seen for Na/Cu ratio is >0.8.

Example 15. Effect of Adding Li to the Change of Alkaline Type and its Corresponding Structure Synthesis detail to Example 15 (Sample 15 series): The Sample 15 series was made by the following method. A 150 mL aqueous solution containing 24.62 g $Mg(NO_3)_2 \cdot 6H_2O$ (0.10 mol), 5.80 g $Cu(NO_3)_2 \cdot 6H_2O$ (0.024 mol), and 15.00 g $Al(NO_3)_3 \cdot 9H_2O$ (0.04 mol) was added dropwise to 150 ml aqueous solution containing 5.30 g $Na_2CO_3$ (0.05 mol) at room temperature upon stirring. Use 4M NaOH solution to adjust pH to 10.0 before aging at room temperature for 18 hrs. After aging, the slurry became a thick gel and did not settle easily. Filtered and washed with abundant amount of water and ethanol. Never let the material dry during filtration. The wet precipitate was then added to 600 mL ethanol and stirred at room temperature for 4 hrs. Filter and wash with extra ethanol before vacuum drying at room temperature for 2 days. Yield 12.861 g fluffy blue powder (Sample 15).

Sample 15-3 was made by adding 0.1045 g $LiNO_3$ in 2.4 mL deionized water onto 1.920 g Sample 15, followed by calcination at 650° C. for 4 hrs, yielding 0.44 Li/Cu modified $Mg_3Al$ HT.

Sample 15-4 was made by adding 0.2090 g $LiNO_3$ in 2.4 mL deionized water onto 1.920 g Sample 15, followed by calcination at 650° C. for 4 hrs, yielding 0.88 Li/Cu modified $Mg_3Al$ HT.

Figure 22:
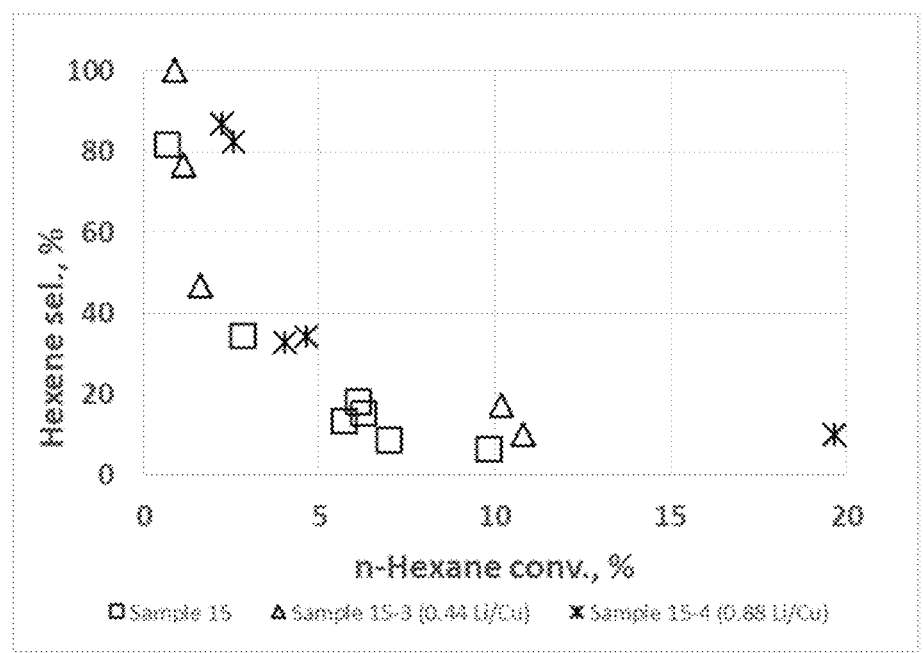
FIG. 22 is a graph depicting n-Hexane conversion and n-hexene selectivity profiles for the 184 series of $Cu_xMg_{3-x}AlO_{4.5}$ (Example 15)

This series of materials contain varying amount of lithium (expressed in the Li/Cu mole ratio). They were calcined under static air at 650° C. for 3 h before use. The n-hexene selectivity vs. n-hexane conversion profile is shown in FIG. 22. It can be seen that presence of lithium has minimal beneficial effect on the selectivity to hexenes.

Figure 23:
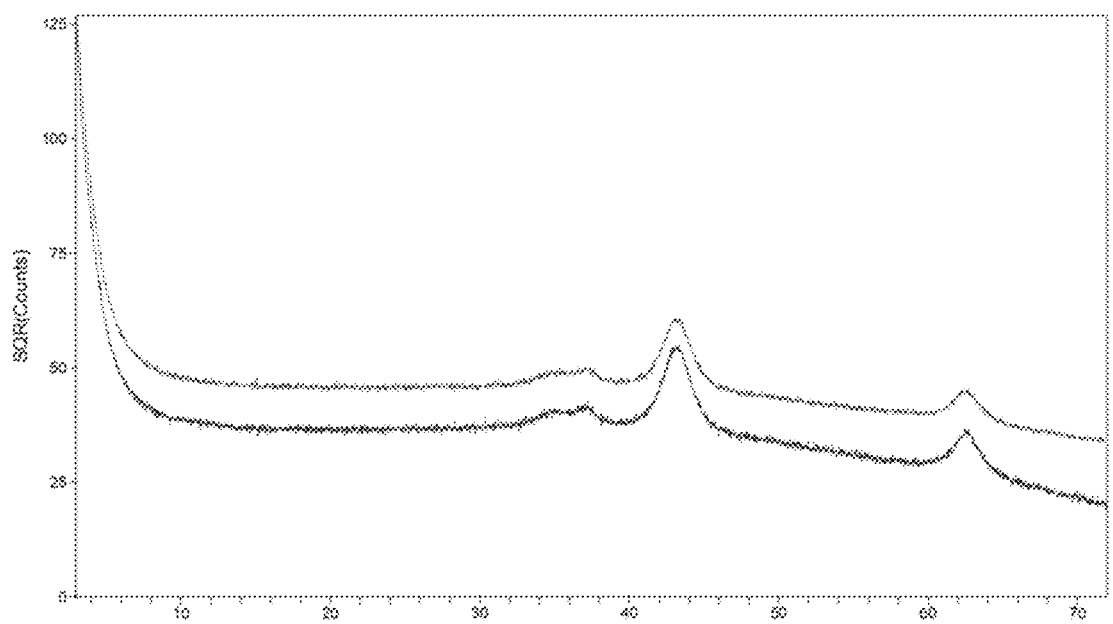
FIG. 23 is an X-Ray Diffractogram (XRD) of Example 15.

Corresponding XRD appear in FIG. 23 (bottom, Sample 15-3; top, Sample 15-4).

Example 16: Effect of Changing Base $Mg_3Al$ HT to $Ni_3Al$ or $Co_3Al$ While Keeping Cu % Constant Synthesis detail to Example 16 (Sample 16 Cu in $Ni_3Al$ HT): This sample was made by the following method. A 60 mL aqueous solution containing 11.632 g $Ni(NO_3)_2 \cdot 6H_2O$ (0.04 mol), 2.416 g $Cu(NO_3)_2 \cdot 6H_2O$ (0.010 mol), and 6.252 g $Al(NO_3)_3 \cdot 9H_2O$ (0.017 mol) was added to a 60 ml aqueous solution containing 7.066 g $Na_2CO_3$ (0.067 mol) at room temperature with stirring. Use 4M NaOH solution to adjust pH to 10.0. Age solution at room temperature for 16 hours, then heat at 60° C. for 8 hours. Filtered and washed with abundant amount of water and acetone. Never let the material dry during filtration. Allow sample to dry in air at room temperature first, then at 100° C. for 4 hours. Yield 6.521 g bluish green powder. Yielded Sample 16. Sample was then calcined at 650° C. for 4 hrs, and is named Sample 16A.

Sample 16B is made by adding 0.08 g $Na_2CO_3$ in 2.1 mL deionized water onto 1.92 g Sample 16, followed by calcination at 650° C. for 4 hrs, yielding 0.44 Na/Cu modified $Ni_3Al$ HT.

Figure 24:
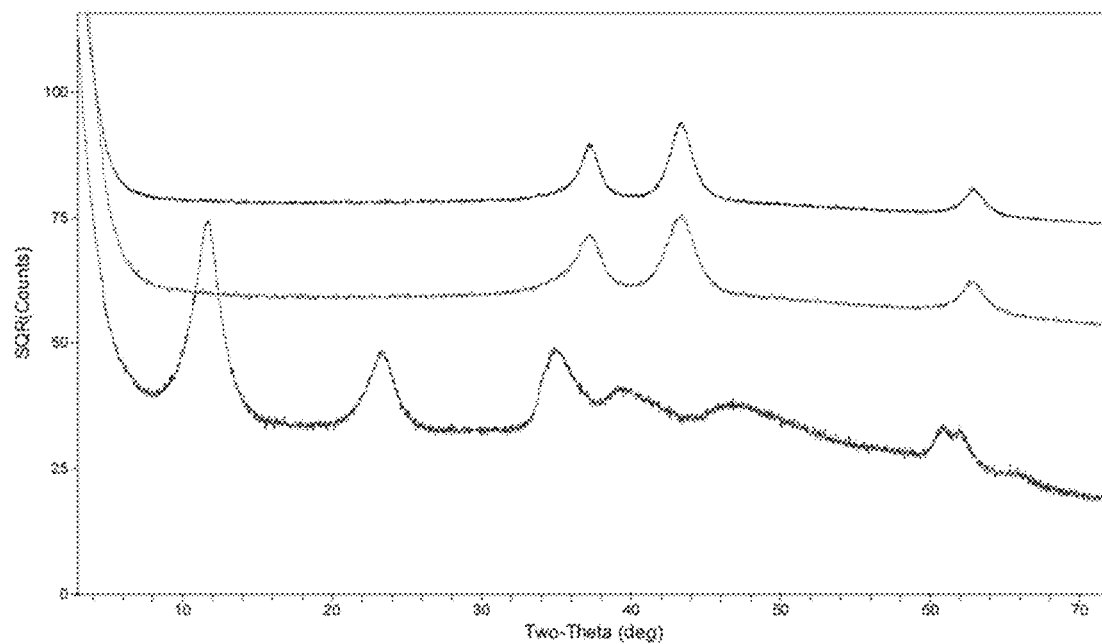
FIG. 24 is an X-Ray Diffractogram (XRD) of Example 16

Corresponding XRD appear in FIG. 24 (bottom, as-synthesized Sample 16, middle Sample 16A; top, Sample 16B).

Figure 25:
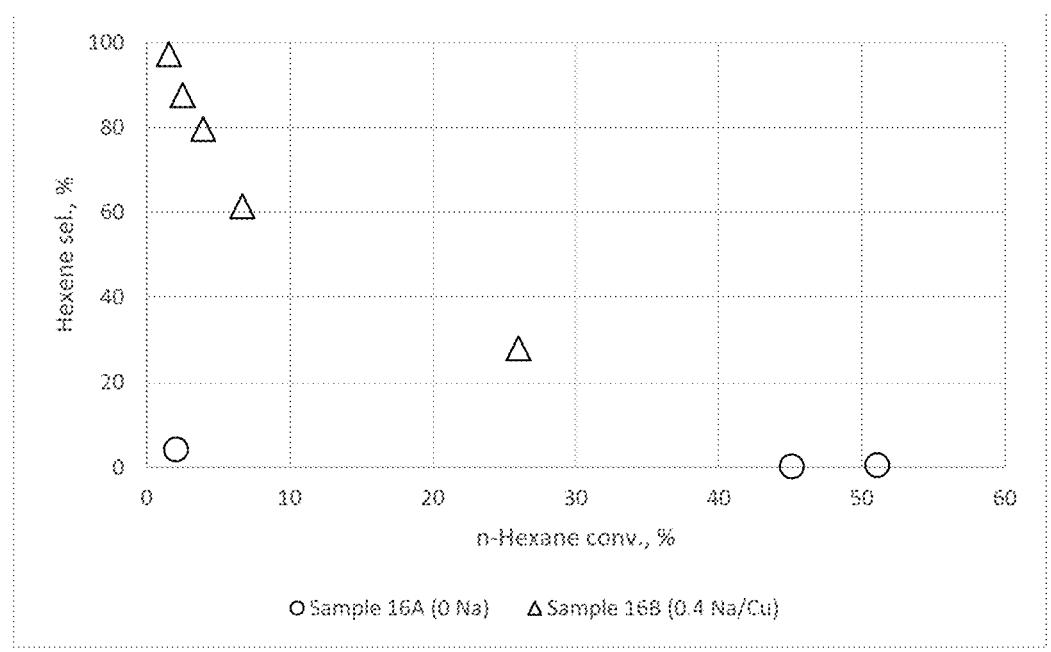
FIG. 25 is a graph depicting n-Hexane conversion and n-hexene selectivity profiles for the 169B-4 series of $Cu_xNi_{3-x}AlO_{4.5}$ (Example 16)

This series of materials have been tested for n-hexane oxidative dehydrogenation to hexenes. The n-hexene selectivity vs. n-hexane conversion profile is shown in FIG. 25. It can be seen that presence of sodium has a beneficial effect on the selectivity to hexenes.

Example 17: Synthesis of CuOx in $Co_3Al$ HT

Synthesis detail to Example 17 (Sample 17 Cu in $Co_3Al$ HT): This sample was made by the following method. A 60 mL aqueous solution containing 11.641 g $Co(NO_3)_2 \cdot 6H_2O$ (0.04 mol), 2.416 g $Cu(NO_3)_2 \cdot 6H_2O$ (0.010 mol), and 6.252 g $Al(NO_3)_3 \cdot 9H_2O$ (0.017 mol) was added to a 60 ml aqueous solution containing 7.066 g $Na_2CO_3$ (0.067 mol) at room temperature with stirring. Use 4M NaOH solution to adjust pH to 10.0. Age solution at room temperature for 16 hours, then heat at 60° C. for 8 hours. Filtered and washed with abundant amount of water and acetone. Never let the material dry during filtration. Allow sample to dry in air at room temperature first, then at 100° C. for 4 hours. Yield 6.606 g grey powder. Yielded Sample 17. Sample was then calcined at 650° C. for 4 hrs, named Sample 17A.

Sample 17B is made by adding 0.08 g $Na_2CO_3$ in 2.1 mL deionized water onto 1.92 g Sample 17, followed by calcination at 650° C. for 4 hrs, yielding 0.44 Na/Cu modified $Co_3Al$ HT. direct XRD comparison is shown below.

Figure 26:
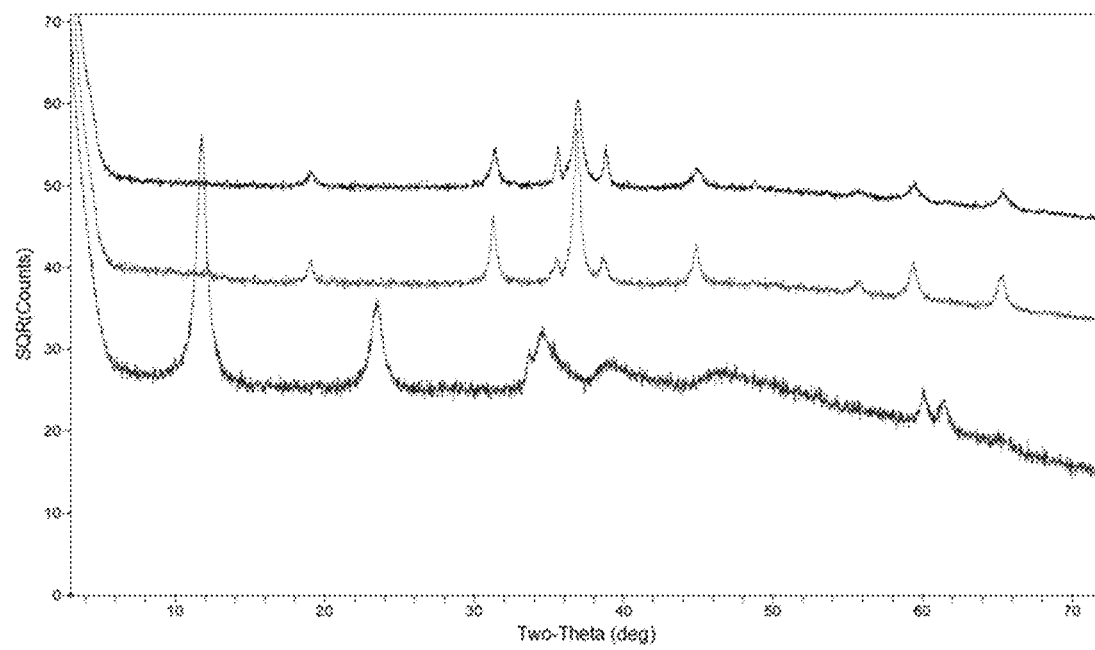
FIG. 26 is an X-Ray Diffractogram (XRD) of Example 17
Figure 28:
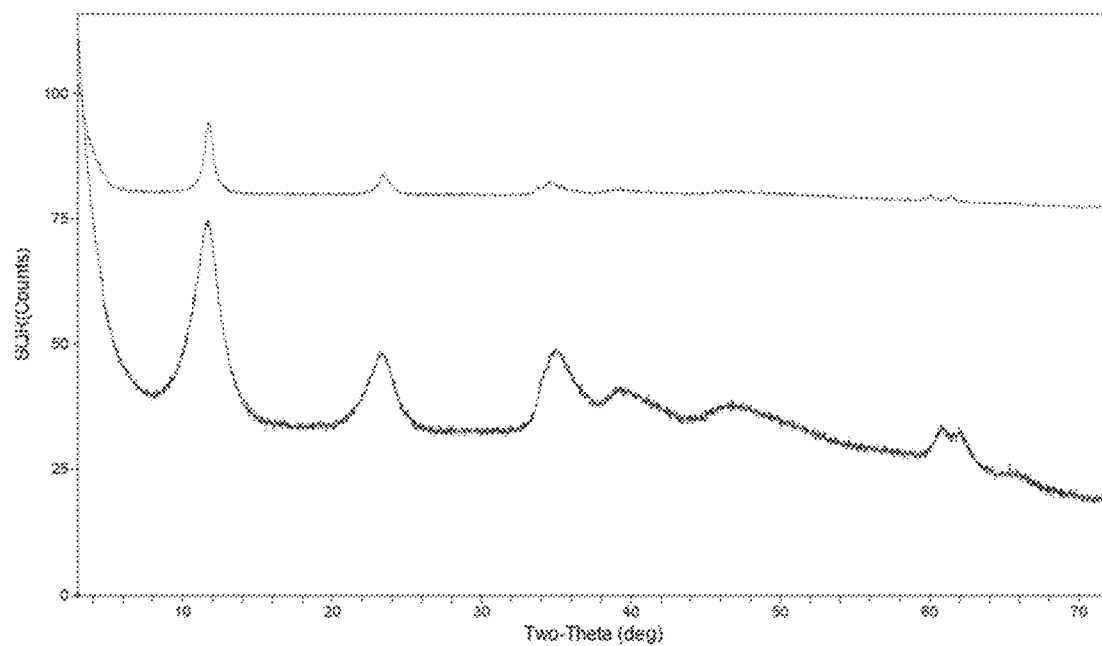
FIG. 28 is an X-Ray Diffractogram (XRD) of Example 17
Figure 29:
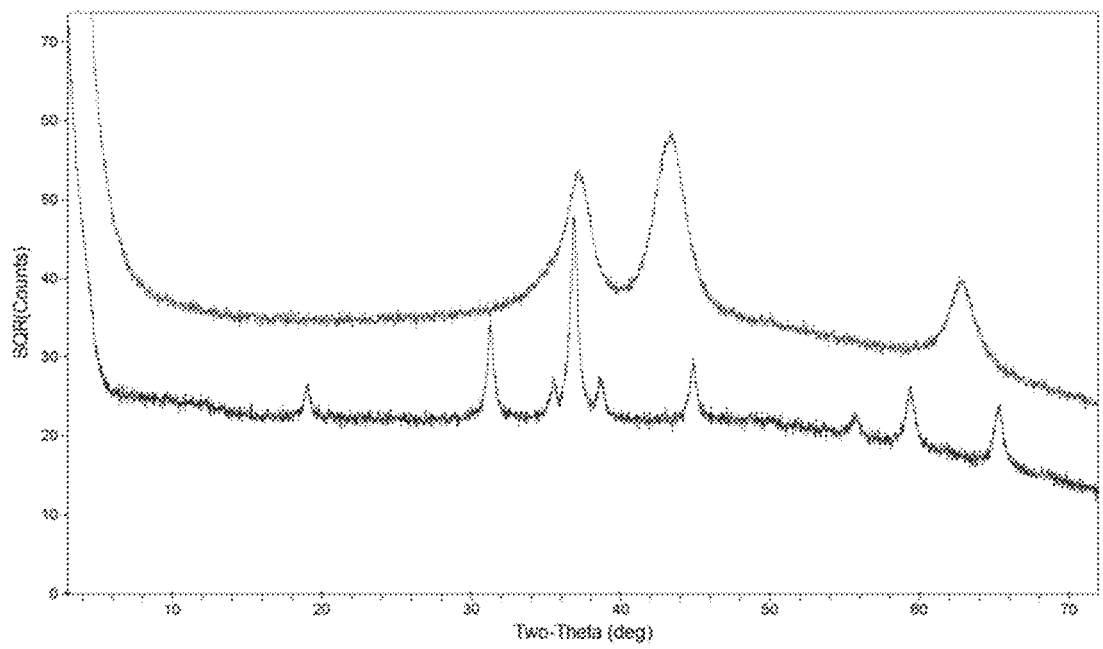
FIG. 29 is an X-Ray Diffractogram (XRD) of Example 17

Corresponding XRD appear in FIGS. 26, 28 and 29. FIG. 26: bottom, as-synthesized Sample 17; middle, Sample 17A; top, Sample 17B. FIG. 28: bottom, as-synthesized Sample 16; top, as-synthesized Sample 17. FIG. 29: bottom, Sample 17A; top, Sample 16A.

Figure 27:
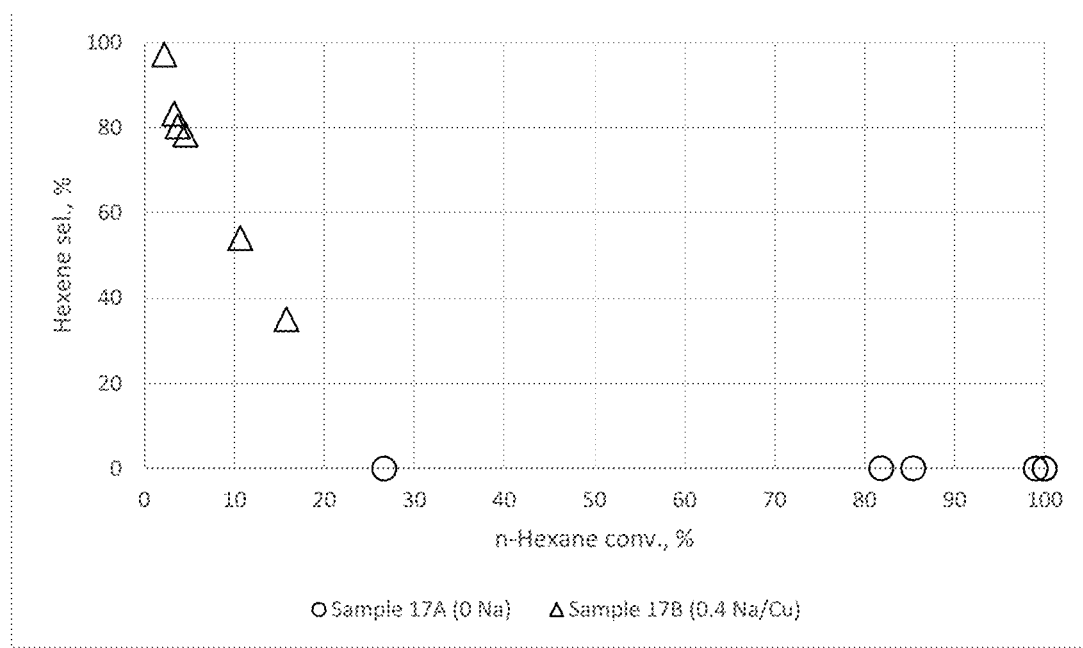
FIG. 27 is a graph depicting n-Hexane conversion and n-hexene selectivity profiles for the 169B-5 series of $Cu_xCo_{3-x}AlO_{4.5}$ (Example 17)

This series of materials have been tested for n-hexane oxidative dehydrogenation to hexenes. The n-hexene selectivity vs. n-hexane conversion profile is shown in FIG. 27. It can be seen that presence of sodium has a beneficial effect on the selectivity to hexenes.

Example 18: Effect of Keeping $Mg_3Al$ Constant but Changing Cu to Co, Ni, Fe Synthesis detail to Example 18 (Sample 18 Ni in $Mg_3Al$): This was made by the following method. A 60 mL aqueous solution containing 2.908 g $Ni(NO_3)_2 \cdot 6H_2O$ (0.010 mol), 10.256 g $Mg(NO_3)_2 \cdot 6H_2O$ (0.040 mol), and 6.252 g $Al(NO_3)_3 \cdot 9H_2O$ (0.017 mol) was added to a 60 ml aqueous solution containing 1.767 g $Na_2CO_3$ (0.017 mol) at room temperature with stirring. Use 4M NaOH solution to adjust pH to 10.0. Age solution at room temperature for 16 hours, then heat at 60° C. for 8 hours. Filtered and washed with abundant amount of water and acetone. Never let the material dry during filtration. Allow sample to dry in air at room temperature first, then at 100° C. for 4 hours. Yield 5.1947 g green powder. Sample was then calcined at 650° C. for 4 hrs.

Example 19: Synthesis of FeOx in $Mg_3Al$ HT

Synthesis detail to Example 19 (Sample 19 Fe in $Mg_3Al$): This was made by the following method. A 60 mL aqueous solution containing 4.040 g $Fe(NO_3)_3 \cdot 9H_2O$ (0.010 mol), 12.821 g $Mg(NO_3)_2 \cdot 6H_2O$ (0.050 mol), and 2.501 g $Al(NO_3)_3 \cdot 9H_2O$ (0.007 mol) was added to a 60 ml aqueous solution containing 1.767 g $Na_2CO_3$ (0.017 mol) at room temperature with stirring. Use 4M NaOH solution to adjust pH to 10.0. Age solution at room temperature for 16 hours, then heat at 60° C. for 8 hours. Filtered and washed with abundant amount of water and acetone. Never let the material dry during filtration. Allow sample to dry in air at room temperature first, then at 100° C. for 4 hours. Yield 5.184 g off-white powder. Sample is called Sample 19B. Sample was then calcined at 650° C. for 4 hrs, and it is named as Sample 19B-650.

Figure 30:
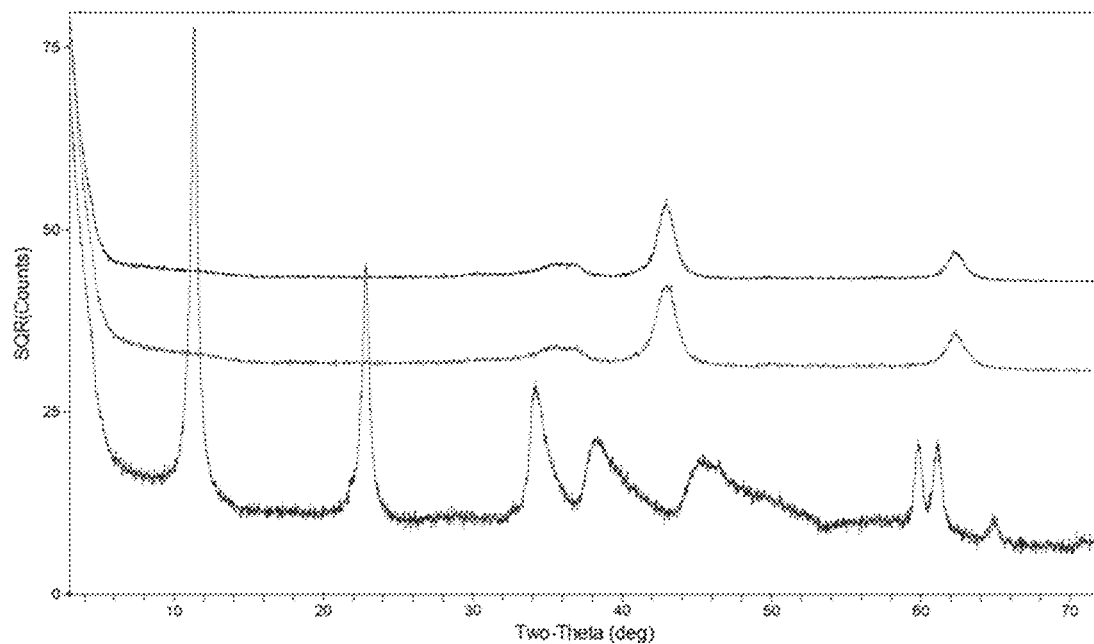
FIG. 30 is an X-Ray Diffractogram (XRD) of Example 19.

Sample 19B-1-650 is made by adding 0.08 g $Na_2CO_3$ in 2.1 mL deionized water onto 1.92 g Sample 19B, followed by calcination at 650° C. for 4 hrs, yielding 0.44 Na/Fe modified $Mg_3Al$ HT. direct XRD comparison is shown in FIG. 30 (bottom, Sample 19B as-synthesized; middle, Sample 19B-650; top, Sample 19B-1-650.

Figure 31:
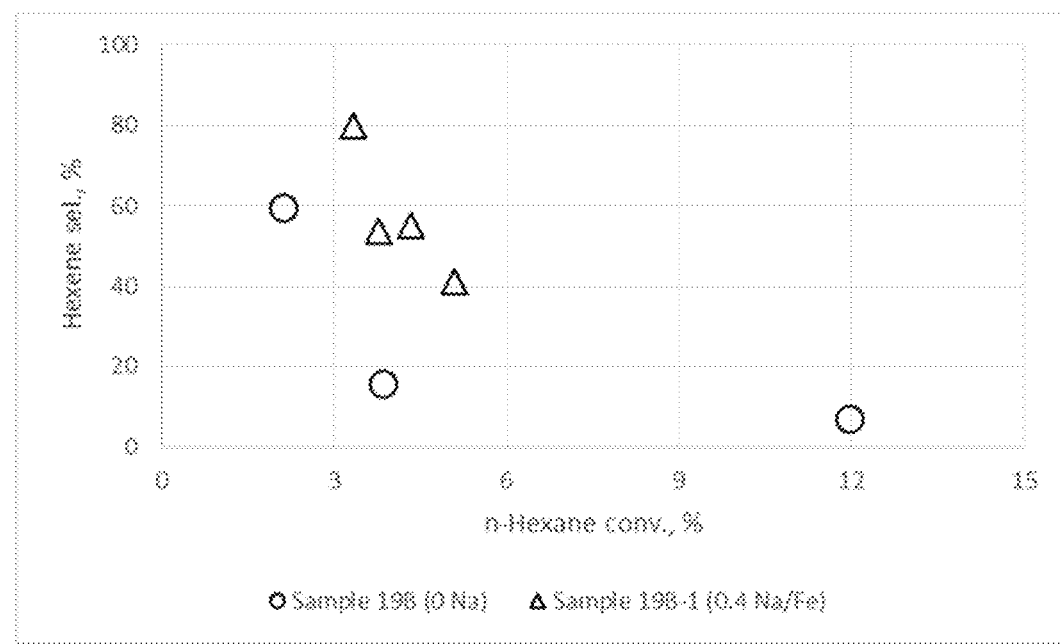
FIG. 31 is a graph depicting n-Hexane conversion and n-hexene selectivity profiles for the 27059-1B series of $FE_xMg_{3-x}AlO_{4.5}$ (Example 19)

This series of materials have been tested for n-hexane oxidative dehydrogenation to hexenes. The n-hexene selectivity vs. n-hexane conversion profile is shown in FIG. 31. It can be seen that presence of sodium has a beneficial effect on the selectivity to hexenes.

Example 20: Synthesis of CoOx in $Mg_3Al$ HT

Synthesis detail to Example 20 (Sample 20 Co in $Mg_3Al$): This was made by the following method. A 60 mL aqueous solution containing 2.910 g $Co(NO_3)_2 \cdot 6H_2O$ (0.010 mol), 10.256 g $Mg(NO_3)_2 \cdot 6H_2O$ (0.040 mol), and 6.252 g $Al(NO_3)_3 \cdot 9H_2O$ (0.017 mol) was added to a 60 ml aqueous solution containing 1.767 g $Na_2CO_3$ (0.017 mol) at room temperature with stirring. Use 4M NaOH solution to adjust pH to 10.0. Age solution at room temperature for 16 hours, then heat at 60° C. for 8 hours. Filtered and washed with abundant amount of water and acetone. Never let the material dry during filtration. Allow sample to dry in air at room temperature first then at 100° C. for 4 hours, yielding a pink powder. Sample 20B was obtained. Sample was then calcined at 650° C. for 4 hrs, named Sample 20B-650.

Figure 32:
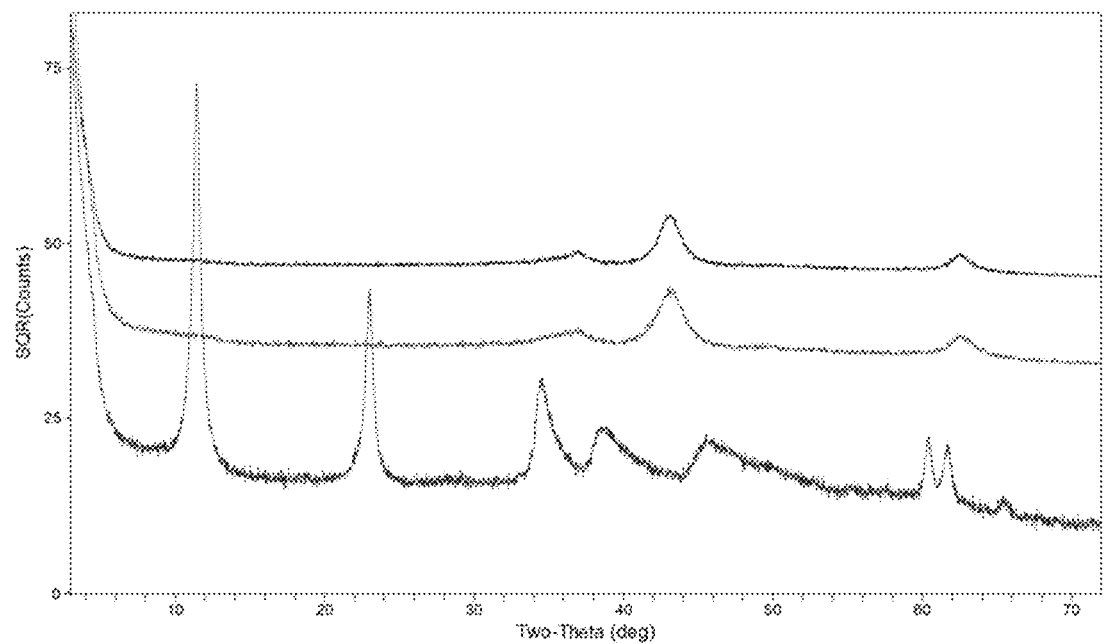
FIG. 32 is an X-Ray Diffractogram (XRD) of Example 20
Figure 34:
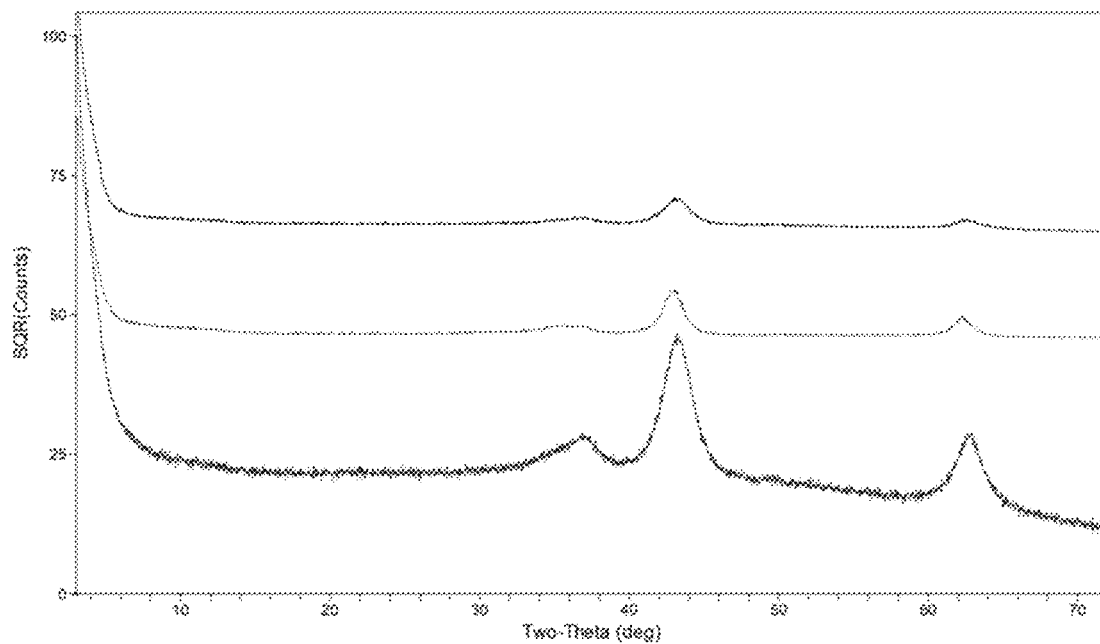
FIG. 34 is an X-Ray Diffractogram (XRD) of Example 20

Sample 20B-1-650 is made by adding 0.08 g $Na_2CO_3$ in 2.1 mL deionized water onto 1.92 g Sample 20B, followed by calcination at 650° C. for 4 hrs, yielding 0.44 Na/Co modified $Mg_3Al$ HT. direct XRD comparison is shown in FIGS. 32 and 34. FIG. 32: bottom, Sample 20B; middle, Sample 20B-650; top, Sample 20B-1-650. FIG. 34: bottom, Sample 18 as-synthesized; middle, Sample 19B-650; top, Sample 20B-650.

Figure 33:
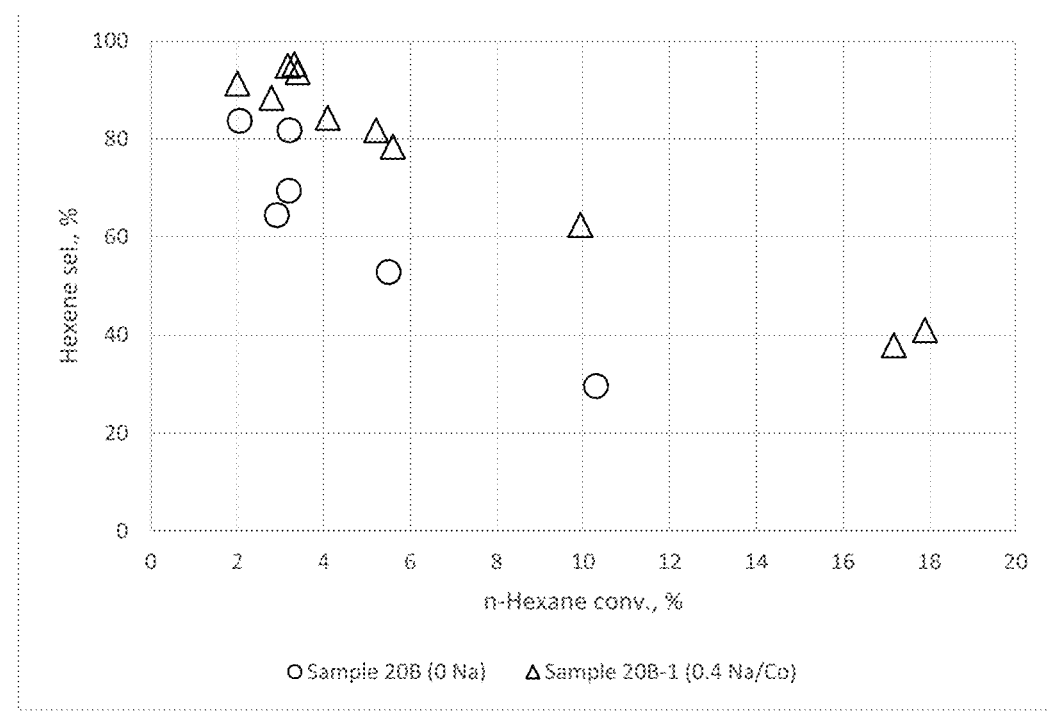
FIG. 33 is a graph depicting n-Hexane conversion and n-hexene selectivity profiles for the 192B series of $Co_xMg_{3-x}AlO_{4.5}$ (Example 20)

This series of materials have been tested for n-hexane oxidative dehydrogenation to hexenes. The n-hexene selectivity vs. n-hexane conversion profile is shown in FIG. 33. It can be seen that presence of sodium has a beneficial effect on the selectivity to hexenes.

Figure 35:
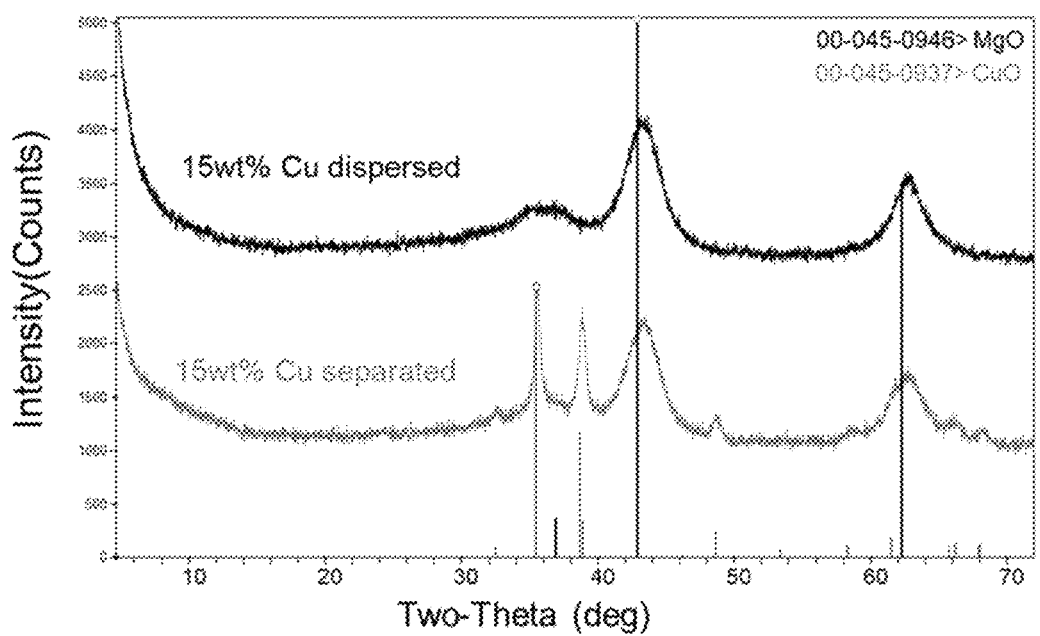
FIG. 35 is an X-Ray Diffractogram (XRD) demonstrating the importance to use Na2CO3 as a primary precipitation step (upper) instead of NaOH (lower)
FIG. 36 are HAADF STEM images confirming the atomically dispersion of Cu into $Mg_3Al$ HT system (26951-80E, Example 9).

Example 21 Differentiating Synthesis 1—Usage of $Na_2CO_3$ to Atomically Disperse CuO into $Mg_3Al$ Hydrotalcite (HT) Lattice XRD shown in FIG. 35 illustrates the importance to use $Na_2CO_3$ as a primary precipitation step (top) instead of NaOH (bottom) as the latter induces phase separation of CuO in the finishing products because $Cu(OH)_2$ has a lower solubility at high pH compared to the Cu—$Mg_3Al$ HT phase. Examples (6 to 10) are all using $Na_2CO_3$ as primary precipitation and only added NaOH to fine tune the pH before aging.

Figure 36:
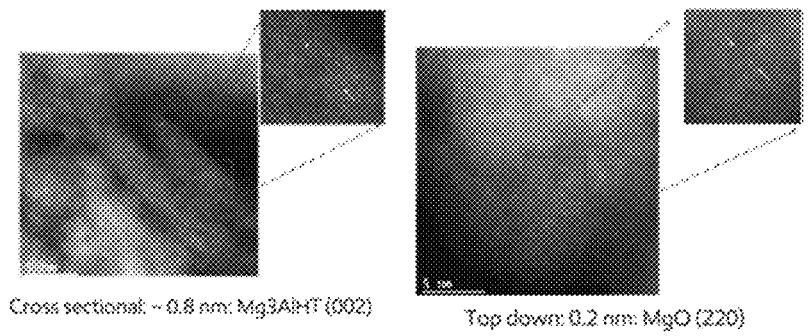
Figure 37:
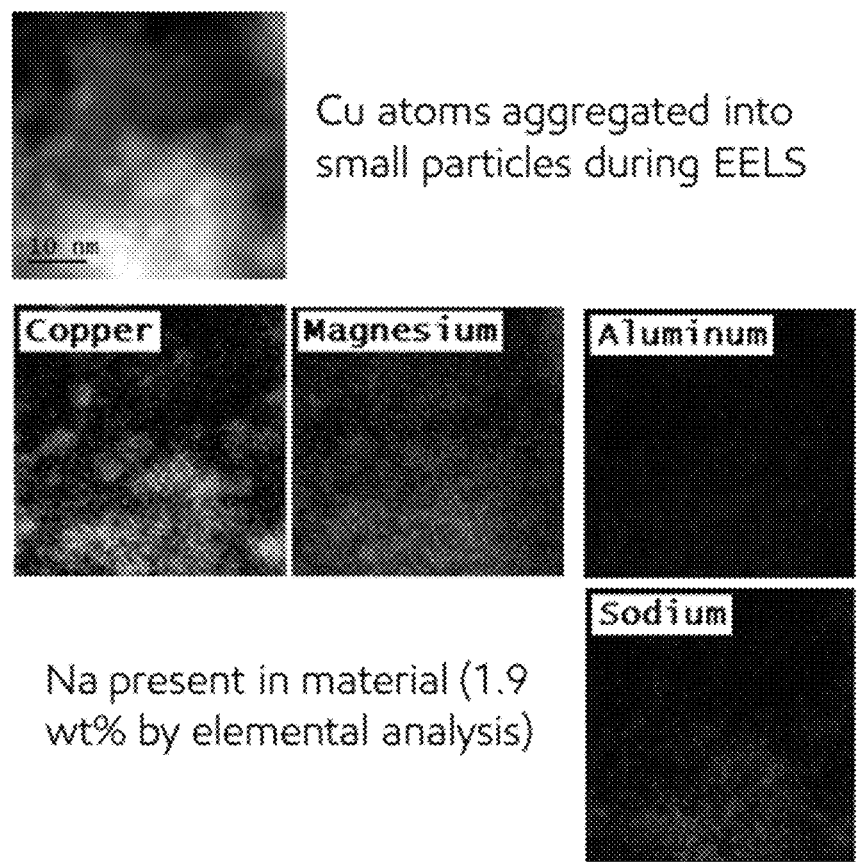
FIG. 37 are EELS analysis images demonstrating the aggregation of Cu atoms during long electron beam exposure.

Cu particle aggregation was observed to occur during long exposure EELS analyses, which was not present at the beginning of the scan. But the distribution of Na and presence of Na is confirmed below (Sample 9, Example 9). This same sample has 1.9 wt % Na content measured by XRF elemental analysis on the HT precursor prior to calcination. See, FIGS. 36 and 37.

Figure 38:
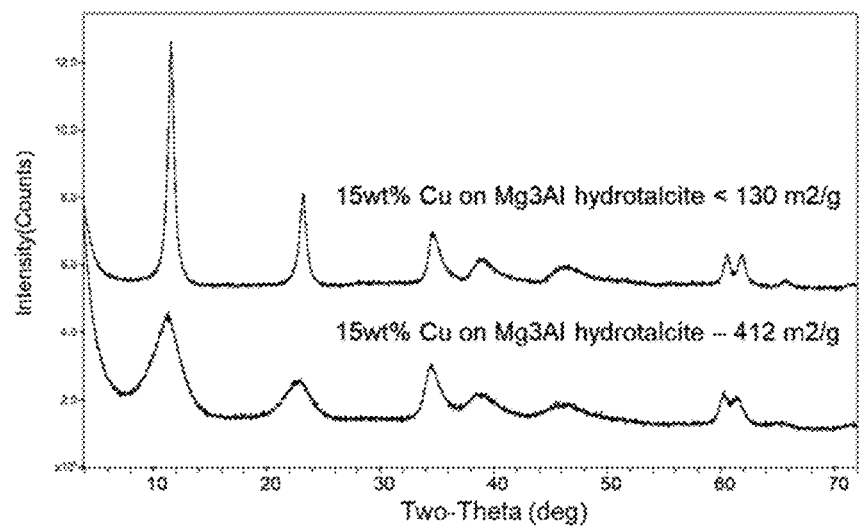
FIG. 38 is an X-Ray Diffractogram (XRD) demonstrating the peak broadening observed for the high surface area Cu on $Mg_3Al$ HT (HT stands for hydrotalcite) using the alcohol or acetone aging method prior to complete drying from water base synthesis.

Example 22 Differentiating Synthesis 2—Usage of Alcohol to Displace Water to Largely Increase HT Surface Area XRD diffraction peaks broadening is observed for the high surface area Cu on $Mg_3Al$ HT using the alcohol or acetone aging method prior to complete drying from water base synthesis. See, FIG. 38.

Figure 39:
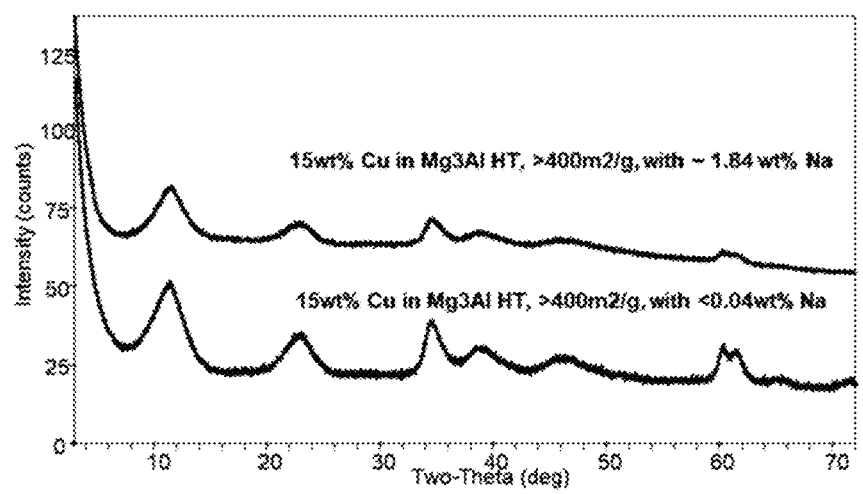
FIG. 39 is an X-Ray Diffractogram (XRD) demonstrating that the XRD will appear to be identical for samples with similar surface area and similar Cu composition but various Na loading.

Example 23 Differentiating Synthesis 3—Addition of Na from Synthesis or Post-Synthesis Modification without Forming $Na_2CO_3$ Peaks in XRD XRD will appear to be identical for samples with similar surface area and similar Cu composition but various Na loading, which can be confirmed by elemental analysis (XRF or ICP-MS). The Na content is critically important in this invention. See, FIG. 39.

TRANSITIONAL PHRASES

All documents described herein are incorporated by reference herein, including any priority documents and or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that it also contemplates the same composition or group of elements with transitional phrases "consisting essentially of," "consisting of," "selected from the group of consisting of," or "is" preceding the recitation of the composition, element, or elements and vice versa.

INCORPORATION BY REFERENCE

The entire contents of all patents, published patent applications and other references cited herein are hereby expressly incorporated herein in their entireties by reference.

EQUIVALENTS

While the present disclosure has been described with respect to a number of embodiments and examples, those skilled in the art, having benefit of this disclosure, will appreciate that other embodiments can be devised which do not depart from the scope and spirit of the present disclosure.

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired products, additional ingredients may be added, and/or similar ingredients may be substituted for one or more of the ingredients described.

Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. An active material, comprising:
   a mixed metal oxide of the formula:

$$A_a(M1)_x(M2)_{y-x}(M3)_zO_{y+3/2z} \quad (I)$$

wherein:
   A is an alkali metal;
   M1 is a divalent metal;
   M2 is a divalent metal;
   M3 is Al;
   a is 0.01≤a≤4;
   x is 0.01≤x≤4;
   y is an integer from 2≤y≤4;
   z is 0.25y≤z≤0.5y to satisfy charge neutralization; and
   the ratio a/x is from 0.1 to 1.0;
   and an optional support material.

2. The active material according to claim 1, wherein A is selected from the group consisting of Na, Li, K, Rb, and Cs.

3. The active material according to claim 2, wherein A is Na.

4. The active material according to claim 1, wherein M1 is selected from the group consisting of Mn, Fe, Co, Ni, and Cu.

5. The active material according to claim 4, wherein M1 is Fe, Co, Ni, or Cu.

6. The active material according to claim 4, wherein M1 is Cu.

7. The active material according to claim 1, wherein M2 is selected from the group consisting of Mg, Ca, Sr, Ba, Zn, Co, Cu, Ni, and Fe.

8. The active material according to claim 7, wherein M2 is Mg, Co, or Ni.

9. The active material according to claim 8, wherein M2 is Mg.

10. The active material according to claim 1, wherein the active material has a structure having X-Ray diffraction peaks at d-spacing corresponding to three characteristic features of an $M_2O$ rocksalt phase, d1, d2 and d3,
    wherein the three characteristic d-spacing are:

$$2.41 \text{ Å} < d1 < 2.49 \text{ Å},$$

$$2.09 \text{ Å} < d2 < 2.15 \text{ Å},$$

$$1.48 \text{ Å} < d3 < 1.52 \text{ Å};$$

and wherein the structure is substantially free of X-Ray diffraction peaks at d-spacing corresponding to an M1O phase.

11. The active material according to claim 1, having the formula:
    $Cu_xMg_{3-x}AlO_{4.5}$, comprising Na, Cs, K, Li, or mixtures thereof where x is 0.01≤x≤3.

12. The active material according to claim 1, wherein the support material is a non-acidic oxide, a non-acidic clay, a basic oxide, a zeolite, an organoclay, or a combination thereof.

13. The active material according to claim 1, wherein the support material is selected from zeolites, organoclays, $Al_2O_3$, $ZrO_2$, $SiO_2$, $SiO_2/Al_2O_3$, $SiO_2/TiO_2$, silica clay, silicon oxide/clay, or mixtures thereof.

14. A process for upgrading a hydrocarbon feed, comprising:
    introducing at a temperature of from about 50° C. to about 500° C. a hydrocarbon feed comprising paraffins and introducing an oxidizing agent to an active material according to claim 1;
    obtaining a product mixture comprising one or more $C_3$-$C_{50}$ cyclic olefin, one or more $C_2$-$C_{50}$ acyclic olefin, one or more $C_5$-$C_{200}$ hydrocarbon, or a mixture thereof, wherein the product mixture comprises less than 1000 ppm $H_2$,
    wherein the active material comprises a mixed metal oxide of the formula:

$$A_a(M1)_x(M2)_{y-x}(M3)_zO_{y+3/2z} \quad (I)$$

wherein:
    A is an alkali metal;
    M1 is a divalent metal;
    M2 is a divalent metal;
    M3 is Al;
    a is 0.01≤a≤4;
    x is 0.01≤x≤4;
    y is an integer from 2≤y≤4;
    z is 0.25y≤z≤0.5y to satisfy charge neutralization; and
    the ratio a/x is from 0.1 to 1.0;
    and an optional support material.

15. The process of claim 14, wherein the oxidizing agent is air.

16. The process of claim 14, wherein introducing the oxidizing agent is performed:
    at a temperature of from about 50° C. to about 1,000° C.;
    at a pressure of from about 15 psig to about 500 psig; and
    at a residence time of about 1 milli-second to about 48 hours.

17. The process of claim 14, wherein the hydrocarbon feed is a naphtha feed comprising one or more $C_3$-$C_{50}$ cyclic alkanes, one or more $C_2$-$C_{50}$ acyclic alkanes, or a mixture thereof.

18. The process of claim 14, wherein the feed comprises one or more $C_3$-$C_{50}$ cyclic alkane selected from cyclopropane, cyclobutane, cyclopentane, cyclohexane, cycloheptane, cyclooctane, or mixtures thereof.

19. The process of claim 14, wherein the feed comprises a $C_2$-$C_{50}$ acyclic alkane selected from propane, n-butane, iso-butane, n-pentane, iso-pentane, neo-pentane, n-hexane, iso-hexane, neo-hexane, n-heptane, iso-heptane, neo-heptane, n-octane, iso-octane, neo-octane, or mixtures thereof.

20. The process of claim 14, wherein the hydrocarbon feed consists of n-hexane, n-pentane, n-butane, propane, or mixtures thereof.

21. The process of claim 14, wherein the hydrocarbon feed comprises one or more $C_3$-$C_{50}$ cyclic alkane and one or more $C_2$-$C_{50}$ acyclic alkane, and a molar ratio of cyclic alkane to acyclic alkane is from about 1:250 to about 250:1.

22. The process of claim 14, wherein the mixed metal oxide of the active material has an oxygen capacity of from about 1 wt % to about 50 wt %, based on the weight of the mixed metal oxide.

23. The process of claim 14, wherein introducing the hydrocarbon feed to the active material is performed:
    at a mixed metal oxide/paraffin molar ratio of from 100:1 to 1:100;
    at a temperature of about 100° C. to about 350° C.;
    at a pressure of from about 15 psig to about 1,000 psig; and
    at a residence time of about 1 milli-second to about 48 hours.

24. A method of preparing an active material according to claim 1 comprising the steps of:
- preparing an aqueous solution of one or more metal oxides or metal nitrates or a mixture thereof;
- adjusting the pH to pH 10 with an alkali component to precipitate a mixed metal oxide; and
- aging the mixed metal oxide in to obtain the active material.

25. The method of preparing an active metal material according to claim 24, wherein the alkali component comprises Na, Li, K, Rb, Cs, or a combination thereof.

26. The method of preparing an active metal material according to claim 24, wherein the metal nitrates include one or more of $Al(NO_3)_3$, $Co(NO_3)_2$, $Mg(NO_3)_2$, $Cu(NO_3)_2$, or hydrates thereof.

27. The method of preparing an active metal material according to claim 24,
- further comprising a step of filtering the mixed metal oxide to provide a wet filtrate after the aging step, wherein the filtering of the mixed metal oxide is performed with an amount of water, optionally including acetone, sufficient to prevent the filtrate from becoming substantially dry.

28. The method of preparing an active metal material according to claim 27,
- further comprising a second step of aging the wet filtrate in a solution of water, optionally including acetone, an alcohol, or both after the step of filtering the mixed metal oxide to provide a wet filtrate after the aging step.

* * * * *